United States Patent
Andreou et al.

(10) Patent No.: US 8,859,749 B2
(45) Date of Patent: Oct. 14, 2014

(54) MODIFIED SHORT INTERFERING RNA

(75) Inventors: Ioanna Andreou, Cologne (DE); Stefan Pitsch, Zürich (CH); Evelyne Muller, Lausanne (CH); Luc Reymond, Chavannes (CH)

(73) Assignee: QIAGEN GmbH, Hilden (DE)

( * ) Notice: Subject to any disclaimer, the term of this patent is extended or adjusted under 35 U.S.C. 154(b) by 1035 days.

(21) Appl. No.: 11/885,782

(22) PCT Filed: Mar. 8, 2006

(86) PCT No.: PCT/EP2006/002131
§ 371 (c)(1),
(2), (4) Date: Jun. 2, 2008

(87) PCT Pub. No.: WO2006/102970
PCT Pub. Date: Oct. 5, 2006

(65) Prior Publication Data
US 2009/0197332 A1    Aug. 6, 2009

(30) Foreign Application Priority Data
Mar. 8, 2005 (EP) ..................................... 05005027

(51) Int. Cl.
*C07H 21/04* (2006.01)
*C12N 15/11* (2006.01)

(52) U.S. Cl.
USPC ....................................... 536/24.5; 514/44 A

(58) Field of Classification Search
None
See application file for complete search history.

(56) References Cited

U.S. PATENT DOCUMENTS

| 2003/0143732 A1* | 7/2003 | Fosnaugh et al. ............. 435/325 |
| 2004/0171032 A1* | 9/2004 | Baker et al. ....................... 435/6 |
| 2005/0032068 A1* | 2/2005 | Prakash et al. .................... 435/6 |
| 2007/0269889 A1* | 11/2007 | Leake et al. ................... 435/375 |

FOREIGN PATENT DOCUMENTS

| WO | WO 02/44321 A2 | 6/2002 |
| WO | WO 03/099840 A1 | 12/2003 |

OTHER PUBLICATIONS

Marshall et al., Recent advances in the high-speed solid phase synthesis of RNA, 2004, Current Opinion in Chemical Biology, vol. 8, pp. 222-229.*
Bobkov et al., Synthesis of oligoribonucleotides containing pyrimidine 2'-O[(hydroxyalkoxy0methyl] ribonucleosides, 2006, Collection of Czechoslovak Chemical Communications, vol. 71, pp. 804-819.*

* cited by examiner

*Primary Examiner* — Dana Shin
(74) *Attorney, Agent, or Firm* — McDermott Will & Emery LLP

(57) ABSTRACT

The present invention refers to a double-stranded siRNA molecule comprising a sense Strand and an antisense Strand which is essentially complementary to the sense Strand, each of the sense and the antisense Strands comprising at least 17 nucleotides (nt), the siRNA further comprising at least one overhang at the 5' and/or 3' end, wherein the overhang residue or overhang residues are chemically modified and selected independently from each other from the group consisting of: (a) 2'-deoxy modified nucleotides; (b) 2'-methoxy modified nucleotides; (c) two nucleosides linked by a 3' to 5' or 2' to 5' formacetal linkage; (d) nucleotides modified at the 2'-position by a —O—$CH_2$—O—$(CH_2)_2$—OH group; and (e) nucleotides comprising in the 3'-position a —$CH_2$—O—$(CH_2)_7$—$CH_3$ group.

12 Claims, 40 Drawing Sheets

Transfection of HeLaS3 cells with MAPK2 (ERK2) siRNAs and HiPerFect

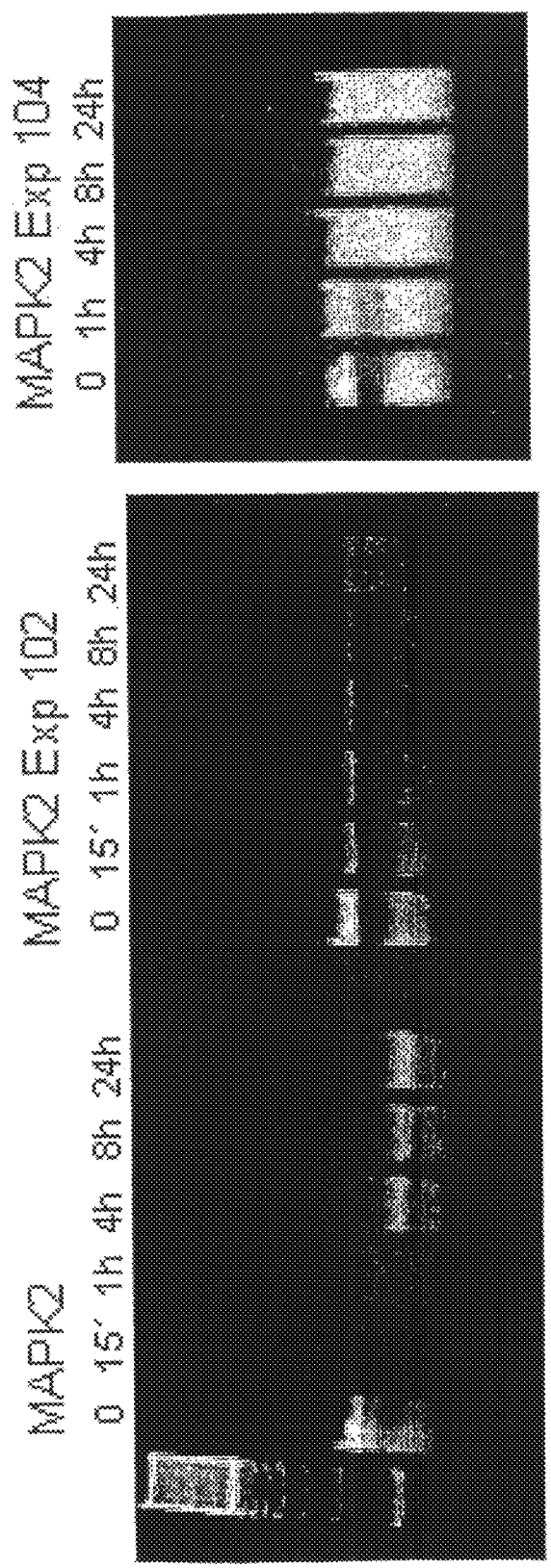

```
                        SEQUENCE LISTING

<160> NUMBER OF SEQ ID NOS: 194

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ugcugacucc aaagcucug                                                 19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
cuggacuucc agaagaaca                                                 19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gggucagcuc guuacucaa                                                 19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gggacaccuc guaacucaa                                                 19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 5
uggcacugaa ucauccaua                                          19

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggcgggtgga tgctgagaac a                                       21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tgtcaatctc caccagtcgg g                                       21

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ccttccaacc tgctgctcaa cac                                     23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gccacatatt ctgtcaggaa ccc                                     23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aataagccgg ggatctacca tac                                     23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 11
tttcatggct accacttgac ctg                                              23

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gaaggtgaag gtcggagt                                                    18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gaagatggtg atgggatttc                                                  20

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
atctacagtg aggagctgcg tgaga                                            25

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tggcccgtgt tgcagatcca gac                                              23

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
atggagttgt gtataagggt agac                                             24

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 17
caagcttccc gttctcagcc t                                              21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ugcugacucc aaagcucugu u                                              21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
cagagcuuug gagucagcau u                                              21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
cagagcuuug gagucagcau u                                              21

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ugcugacucc aaagcucugu u                                              21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
cagagcuuug gagucagcau u                                              21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
```
cagagcuuug gagucagcau u                                       21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ugcugacucc aaagcucugu u                                       21

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
cagagcuuug gagucagcau u                                       21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
cagagcuuug gagucagcau u                                       21

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
cagagcuuug gagucagcau u                                       21

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
ugcugacucc aaagcucugu u                                       21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29

-continued cagagcuuug gagucagcau u                                              21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
cagagcuuug gagucagcau u                                              21

<210> SEQ ID NO 31
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
aaugcugacu ccaaagcucu guu                                            23

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
cagagcuuug gagucagcau u                                              21

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
cagagcuuug gagucagcau u                                              21

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
cagagcuuug gagucagcau u                                              21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
cagagcuuug gagucagcau u                                              21

```
<210> SEQ ID NO 36
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
aaugcugacu ccaaagcucu guu                                              23

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
cagagcuuug gagucagcau u                                                21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
cagagcuuug gagucagcau u                                                21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
cagagcuuug gagucagcau u                                                21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
cagagcuuug gagucagcau u                                                21

<210> SEQ ID NO 41
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
aaugcugacu ccaaagcucu guu                                              23
```

```
<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
cagagcuuug gagucagcau u                                              21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
cagagcuuug gagucagcau u                                              21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
cagagcuuug gagucagcau u                                              21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
cagagcuuug gagucagcau u                                              21

<210> SEQ ID NO 46
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
aaugcugacu ccaaagcucu guu                                            23

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
cagagcuuug gagucagcau u                                              21
```

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
cagagcuuug gagucagcau u                                              21

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
cagagcuuug gagucagcau u                                              21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
cagagcuuug gagucagcau u                                              21

<210> SEQ ID NO 51
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
aaugcugacu ccaaagcucu guu                                            23

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
cagagcuuug gagucagcau u                                              21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
cagagcuuug gagucagcau u                                              21

<210> SEQ ID NO 54

-continued

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
cagagcuuug gagucagcau u                                            21

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
cagagcuuug gagucagcau u                                            21

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
cagagcuuug gagucagcau u                                            21

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
cagagcuuug gagucagcau u                                            21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
cagagcuuug gagucagcau u                                            21

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
cagagcuuug gagucagcau u                                            21

<210> SEQ ID NO 60
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
aaugcugacu ccaaagcucu guu                                              23

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
cagagcuuug gagucagcau u                                                21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
cagagcuuug gagucagcau u                                                21

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
cagagcuuug gagucagcau u                                                21

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
cagagcuuug gagucagcau u                                                21

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
cagagcuuug gagucagcau u                                                21

<210> SEQ ID NO 66
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 66
cagagcuuug gagucagcau u                                              21

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
cagagcuuug gagucagcau u                                              21

<210> SEQ ID NO 68
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
cagagcuuug gagucagcau u                                              21

<210> SEQ ID NO 69
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
aaugcugacu ccaaagcucu guu                                            23

<210> SEQ ID NO 70
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
cagagcuuug gagucagcau u                                              21

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
cagagcuuug gagucagcau u                                              21

<210> SEQ ID NO 72
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 72
cagagcuuug gagucagcau u                                              21

<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
cagagcuuug gagucagcau u                                              21

<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
cagagcuuug gagucagcau u                                              21

<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
cagagcuuug gagucagcau u                                              21

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
cagagcuuug gagucagcau u                                              21

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
cagagcuuug gagucagcau u                                              21

<210> SEQ ID NO 78
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 78
aaugcugacu ccaaagcucu guu                                              23

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
cagagcuuug gagucagcau u                                                21

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
cagagcuuug gagucagcau u                                                21

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
cagagcuuug gagucagcau u                                                21

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
cagagcuuug gagucagcau u                                                21

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
cagagcuuug gagucagcau u                                                21

<210> SEQ ID NO 84
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 84
cagagcuuug gagucagcau u                                              21

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
cagagcuuug gagucagcau u                                              21

<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
cagagcuuug gagucagcau u                                              21

<210> SEQ ID NO 87
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
aaugcugacu ccaaagcucu guu                                            23

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
cagagcuuug gagucagcau u                                              21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
cagagcuuug gagucagcau u                                              21

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 90
cagagcuuug gagucagcau u                                        21

<210> SEQ ID NO 91
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
cagagcuuug gagucagcau u                                        21

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
cagagcuuug gagucagcau u                                        21

<210> SEQ ID NO 93
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
cagagcuuug gagucagcau u                                        21

<210> SEQ ID NO 94
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
aaugcugacu ccaaagcucu guu                                      23

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
cagagcuuug gagucagcau u                                        21

<210> SEQ ID NO 96
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 96
cagagcuuug gagucagcau u                                              21

<210> SEQ ID NO 97
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
cagagcuuug gagucagcau u                                              21

<210> SEQ ID NO 98
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
aaugcugacu ccaaagcucu guu                                            23

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
cagagcuuug gagucagcau u                                              21

<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
cagagcuuug gagucagcau u                                              21

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
cagagcuuug gagucagcau u                                              21

<210> SEQ ID NO 102
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
```

```
aaugcugacu ccaaagcucu guu                                            23
```

<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103

```
cagagcuuug gagucagcau u                                              21
```

<210> SEQ ID NO 104
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104

```
cagagcuuug gagucagcau u                                              21
```

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105

```
cagagcuuug gagucagcau u                                              21
```

<210> SEQ ID NO 106
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106

```
aaugcugacu ccaaagcucu guu                                            23
```

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107

```
cagagcuuug gagucagcau u                                              21
```

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
cagagcuuug gagucagcau u                                              21

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
cagagcuuug gagucagcau u                                              21

<210> SEQ ID NO 110
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
aaugcugacu ccaaagcucu guu                                            23

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
cagagcuuug gagucagcau u                                              21

<210> SEQ ID NO 112
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
cagagcuuug gagucagcau u                                              21

<210> SEQ ID NO 113
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
cagagcuuug gagucagcau u                                              21

<210> SEQ ID NO 114
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
aaugcugacu ccaaagcucu guu                                            23

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
cagagcuuug gagucagcau u                                                21

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
cagagcuuug gagucagcau u                                                21

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
cagagcuuug gagucagcau u                                                21

<210> SEQ ID NO 118
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
aaugcugacu ccaaagcucu guu                                              23

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
cagagcuuug gagucagcau u                                                21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
cagagcuuug gagucagcau u                                                21

```
<210> SEQ ID NO 121
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
aacuggacuu ccagaagaac auu                                              23

<210> SEQ ID NO 122
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
uguucuucug gaaguccagu u                                                21

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
uguucuucug gaaguccagu u                                                21

<210> SEQ ID NO 124
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
uggggucagc ucguuacuca auu                                              23

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
uugaguaacg agcugacccc a                                                21

<210> SEQ ID NO 126
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
uggggacacc ucguaacuca auu                                              23
```

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
uugaguuacg aggugccccc a                                              21

<210> SEQ ID NO 128
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
aauggcacug aaucauccau auu                                            23

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
uauggaugau ucagugccau u                                              21

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
uauggaugau ucagugccau u                                              21

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131
aaugcugacu ccaaagcuct guu                                            23

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
cagagcuuug gagucagcau u                                              21

```
<210> SEQ ID NO 133
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
aaugcugacu ccaaagcucu guu                                               23

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
cagagcuuug gagucagcau u                                                 21

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
cagagcuuug gagucagcau u                                                 21

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
cagagcuuug gagucagcau u                                                 21

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
cagagcuuug gagucagcau u                                                 21

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
cagagcuuug gagucagcau u                                                 21
```

```
<210> SEQ ID NO 139
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
aaugcugacu ccaaagcucu guu                                              23

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
cagagcuuug gagucagcau u                                                21

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
cagagcuuug gagucagcau u                                                21

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
cagagcuuug gagucagcau u                                                21

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
cagagcuuug gagucagcau u                                                21

<210> SEQ ID NO 144
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
ddugcugacu ccaaagcucu guu                                              23
```

```
<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
cagagcuuug gagucagcau u                                              21

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
cagagcuuug gagucagcau u                                              21

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
cagagcuuug gagucagcau u                                              21

<210> SEQ ID NO 148
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
ddugcugacu ccaaagcucu guu                                            23

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
cagagcuuug gagucagcau u                                              21

<210> SEQ ID NO 150
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
cagagcuuug gagucagcau u                                              21

<210> SEQ ID NO 151
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
cagagcuuug gagucagcau u                                              21

<210> SEQ ID NO 152
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
cagagcuuug gagucagcau u                                              21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 153
tgcugacucc aaagcucugu u                                              21

<210> SEQ ID NO 154
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
aacagagcuu uggagucagc auu                                            23

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 155
tgcugacucc aaagcucugu u                                              21

<210> SEQ ID NO 156
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
```

```
ddcagagcuu uggagucagc auu                                              23

<210> SEQ ID NO 157
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
aaugcugacu ccaaagcucu guu                                              23

<210> SEQ ID NO 158
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
cagagcuuug gagucagcau u                                                21

<210> SEQ ID NO 159
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
aaugcugacu ccaaagcucu guu                                              23

<210> SEQ ID NO 160
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
cagagcuuug gagucagcau u                                                21

<210> SEQ ID NO 161
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
aaugcugacu ccaaagcucu guu                                              23

<210> SEQ ID NO 162
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
```

```
cagagcuuug gagucagcau u                                           21
```

<210> SEQ ID NO 163
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163

```
aaugcugacu ccaaagcucu guu                                         23
```

<210> SEQ ID NO 164
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164

```
cagagcuuug gagucagcau u                                           21
```

<210> SEQ ID NO 165
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165

```
aaugcugacu ccaaagcucu guu                                         23
```

<210> SEQ ID NO 166
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166

```
cagagcuuug gagucagcau u                                           21
```

<210> SEQ ID NO 167
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167

```
aaugcugacu ccaaagcucu guu                                         23
```

<210> SEQ ID NO 168
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168

```
cagagcuuug gagucagcau u                                           21
```

<210> SEQ ID NO 169
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
aaugcugacu ccaaagcucu guu                                         23

<210> SEQ ID NO 170
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
cagagcuuug gagucagcau u                                           21

<210> SEQ ID NO 171
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
aacuggacuu ccagaagaac auu                                         23

<210> SEQ ID NO 172
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
uguucuucug gaaguccagu u                                           21

<210> SEQ ID NO 173
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
aacuggacuu ccagaagaac auu                                         23

<210> SEQ ID NO 174
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
uguucuucug gaaguccagu u                                           21

```
<210> SEQ ID NO 175
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
ddcuggacuu ccagaagaac auu                                          23

<210> SEQ ID NO 176
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
uguucuucug gaaguccagu u                                            21

<210> SEQ ID NO 177
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
ddcuggacuu ccagaagaac auu                                          23

<210> SEQ ID NO 178
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
uguucuucug gaaguccagu u                                            21

<210> SEQ ID NO 179
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
aacuggacuu ccagaagaac auu                                          23

<210> SEQ ID NO 180
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
uguucuucug gaaguccagu u                                            21
```

```
<210> SEQ ID NO 181
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
aacuggacuu ccagaagaac auu                                             23

<210> SEQ ID NO 182
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
uguucuucug gaaguccagu u                                               21

<210> SEQ ID NO 183
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
aauggcacug aaucauccau auu                                             23

<210> SEQ ID NO 184
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
uauggaugau ucagugccau u                                               21

<210> SEQ ID NO 185
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
aauggcacug aaucauccau auu                                             23

<210> SEQ ID NO 186
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
uauggaugau ucagugccau u                                               21

<210> SEQ ID NO 187
```

<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
dduggcacug aaucauccau auu                                           23

<210> SEQ ID NO 188
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
uauggaugau ucagugccau u                                             21

<210> SEQ ID NO 189
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
dduggcacug aaucauccau auu                                           23

<210> SEQ ID NO 190
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
uauggaugau ucagugccau u                                             21

<210> SEQ ID NO 191
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
uggggucagc ucguuacuca auu                                           23

<210> SEQ ID NO 192
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
uugaguaacg agcugacccc a                                             21

<210> SEQ ID NO 193
<211> LENGTH: 23

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193 ugggqucagc ucguuacuca auu                                              23

<210> SEQ ID NO 194
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
uugaguaacg agcugacccc a                                                21
```

MODIFIED SHORT INTERFERING RNA

RELATED APPLICATIONS

This application is the U.S. National Phase under 35 U.S.C. §371 of International Application No. PCT/EP2006/002131, filed on Mar. 8, 2006, which in turn claims the benefit of European Application No. EP 05005027.7, filed on Mar. 8, 2005, the disclosures of which Applications are incorporated by reference herein.

SEQUENCE LISTING

The instant application contains a Sequence Listing which has been submitted in ASCII format via EFS-Web and is hereby incorporated by reference in its entirety. Said ASCII copy, created on Dec. 13, 2010, is named 07544231.txt and is 46,409 bytes in size.

The present invention relates to double-stranded, short interfering RNA (siRNA) molecules that down-regulate the expression of target genes, whereby the siRNA molecules are chemically modified. Furthermore, the present invention relates to a support material as well as phosphoramidites suitable for producing respective siRNA molecules.

It is known that siRNA molecules (double-stranded (i.e. duplex) short interfering RNA having a length of 21-23 nucleotides (nt) with terminal 3'-overhangs of 2 nucleotides) can be used to post-transcriptionally silence gene expression in mammalian cells (Elbashir et at, Nature 2001, 411:494-498). Complexing of siRNAs with suitable transfection reagents and application of these complexes onto the cells results in endocytotic uptake of the siRNA-complexes. SiRNA is finally released into the cytoplasm and the siRNA molecules are recognized and incorporated into a complex called RISC (RNA induced silencing complex). A RISC associated ATP-depended helicase activity unwinds the duplex and enables either of the two strands to independently guide target mRNA recognition (Tuschï; Mol. Interv. 2002, 2:158-167).

The RISC complex then recognizes a region within the mRNA to which the siRNA sequence is complementary and binds to this region in the mRNA. The mRNA is then endonucleolitically cleaved at that position, where the RISC complex is bound, hi a final step, the endonucleolitically cleaved mRNA is degraded by exonucleases. This mechanism of siRNA mediated gene silencing (RNA interference, RNAi) is widely used to perform knockdown experiments in eukaryotic cell cultures.

It is also known that not every siRNA duplex is able to knockdown the mRNA level to the same degree. Some siRNAs are able to knockdown the initial level to approx. 10-20%, some others to intermediate levels (20-70%), and still others are not able to knockdown the mRNA level to a measurable level at all. There are certain design rales (so called "Tuschl-rules") for the design of siRNAs, but even siRNAs designed according to these rules show the above described variability. The reason for this observation is not known. It is believed that also the thermodynamic stability of the duplex may play a role in the efficiency of the siRNA to induce silencing. This variability as well as the fact that even "good" siRNAs are not able to completely knockout all mRNAs is a severe disadvantage of the siRNA technology {Gong D., Trensd. Biotechnol. 2004, 22:451-454; Khvorova A, Cell 2003, 115:209-216; Schwarz D. S., Cell 2003, 115: 199-208; Reynolds A., Nat. Biotechnol. 2004, 22:326-330). The search for more potent gene silencing either by enhancement of uptake into the cells or by more potent intracellular siRNA duplexes is therefore central to the field of siRNA research.

Moreover, it is known that several chemical modifications have been tested in order to increase the ability of siRNA molecules to induce silencing and also to increase their stability. Chemical modifications of siRNA molecules or oligonucleotides (ODN) are affecting the nuclease stability of these molecules or their affinity to target mRNAs (Manoharan M, Curr. Opin. in Chem. Biol. 2004, 8:570-579). Different types of modifications have been described to improve the stability against serum nucleases and/or to improve the affinity to targets. Described are:

a. 2'-OH modifications with halogen, amine, —O-alkyl, —O-allyl, alkyl-groups;
b. internucleotid linkages, such as orthoester, phosphate ester, phosphodiester, -triester, phosphorothioate, phosphorodithioate, phosphonate, phosphonothioate, phosphorothiotriester, phosphoramidate, phosphorothioamidate, phosphinate, and boronate linkage, ether-, allyl ether-, allyl sulfide-, formacetal/ketal-sulfide-, sulfoxide-, sulfone-, sulfamate-, sulfonamide-, siloxane-, amide-, cationic alkylpolyamine-, guanidyl-, morpholino-, hexose sugar or amide-containing linkage, or a two to four atom linkage;
c. conjugates, such as aminoacids, peptides, polypeptides, protein, sugars, carbonhydrates, lipids, polymers, nucleotides, polynucleotides, as well as combinations thereof, passive delivery with cholesterol conjugates.

Normal (unprotected) siRNAs show a low stability in cell culture media and in body fluids, such as serum. This results in degradation of siRNA during the transfection or the systemic delivery. Accordingly, due to the degradation, less siRNA remains in the cells for efficient silencing, and the degraded (shortened) siRNA may lead to off target effects in cells due to unspecific base pairing.

Transfection of siRNA to cells is shown to lead to off target effects. Specifically, high amounts of siRNA may lead to PKR activation (PKR: Protein Kinase R; double stranded RNA-activated protein kinase). Also, the recognition and incorporation of the sense strand in the RISC instead of the antisense strand might lead also to off target effects.

It is therefore the object of the present invention to provide novel and improved siRNA molecules that are protected against degradation so that the gene silencing activity of the siRNA molecules is improved and the amount of siRNA molecules needed for efficient gene silencing is decreased.

The object is solved by the siRNA molecules according to the independent claims. Further advantageous aspects, details and features of the invention are evident from the dependent claims, the description, the examples and the figures.

The chemically modified siRNA molecules according to the present invention enhance the stability of these molecules in culture media and body fluids, e.g. serum. The degradation of siRNA is effectively suppressed, and the full length siRNA will be more active and lead to no off target effects. Moreover, the sensitivity of the siRNA according to the present invention is enhanced. Lower amount of siRNA will be needed to achieve a high level of gene silencing. The siRNA may be incorporated into the RISC in the right orientation, so that only the antisense strand will be able to induce silencing, which leads to higher specificity. In addition, the sense strand is inactivated due to modifications, resulting in the elimination of off target effects. The siRNA according to the present invention enables a more efficient unwinding of the siRNA duplex and hybridization with the target mRNA, leading to an improved target binding affinity. Furthermore, the transfection efficiency of the siRNAs is enhanced and the biodistribution and pharmacokinetic properties are improved.

Chemically modified siRNA molecules with the combination of the following groups and linkages at the well defined positions of both the sense and antisense strands of the siRNA have not been described previously to simultaneously improve stability, sensitivity and specificity of the siRNA:

(a) 2'-deoxy modified nucleotides;
(b) 2'-methoxy modified nucleotides;
(c) two nucleosides linked by a 3' to 5' or 2' to 5' formacetal linkage;
(d) nucleotides modified at the 2'-position by a —O—$CH_2$—O—$(CEb)_2$-OH group; and
(e) nucleotides comprising in the 3'-position a —O—$CH_2$—O—$(CH_2)_7$—$CH_3$ group.

It is believed that the modified siRNA molecules according to the present invention outperform respective non-modified siRNA molecules with respect to the down-regulation of the expression of a target gene because the modification(s) positively influence the thermostability of the double-stranded (i.e. duplex) RNA. Furthermore, it is assumed that the modification(s) allow for a more efficient opening of the duplex within the RNA-induced silencing complex (RISC), so that the further steps (recognizing of an mRNA sequence, binding to that sequence, and finally cutting same) can be carried out more quickly and with higher efficiency compared to non-modified siRNA.

According to one aspect, the present invention refers to a double-stranded siRNA molecule comprising a sense strand and an antisense strand, whereby the antisense strand is essentially complementary to the sense strand. Each of the sense and the antisense strands comprises at least 17 nucleotides (nt). The siRNA further comprises at least one overhang at the 5' and/or 3' end, wherein the overhang residue or the overhang residues are chemically modified and selected independently from each other from the group consisting of:

(a) 2'-deoxy modified nucleotides;
(b) 2'-methoxy modified nucleotides;
(c) two nucleosides linked by a 3' to 5' or 2' to 5' formacetal linkage;
(d) nucleotides modified at the 2'-position by a —O—$CH_2$—O—$(CH_2)_2$—OH group; and
(e) nucleotides comprising in the 3'-position a —O—$CH_2$—$(CH_2)_7$—$CH_3$ group.

"Independently of each other" means that the overhang can be modified by (a), (b), (c), (d) or (e) alone or by any combination of modifications (a) to (e). Modifications comprising two of the above-mentioned alternatives are e.g. (a) and (b), (a) and (c), (a) and (d), (a) and (e); (b) and (c), (b) and (d), (b) and (e); (c) and (d), (c) and (e); (d) and (e). Modifications comprising three of the above-mentioned alternatives are e.g. (a), (b) and (c), (a), (b) and (d), (a), (b) and (e), (a), (c) and (d), (a), (c) and (e), (a), (d) and (e); (b), (c) and (d), (b), (c) and (e); (c), (d) and (e). Modifications comprising four of the above-mentioned alternatives are e.g. (a), (b), (c) and (d), (a), (b), (c), and (e), (a), (c), (d) and (e); and (b), (c), (d) and (e). The modification comprising five of the above-mentioned alternatives is (a), (b), (c), (d) and (e).

"Independently of each other" further means that the 5' end and/or the 3' end of the sense strand and/or the antisense strand of the siRNA molecule can be modified by any of the aforementioned combinations.

If above and in the following the term "siRNA" is used, this does not mean that the siRNA molecules do contain RNA components exclusively. The siRNA according to the present invention may also contain other components, e.g. modified and/or unmodified DNA moieties as well as modified RNA moieties. More generally, "siRNA" as used herein refers to small interfering nucleic acids (siNA).

The sense and the antisense strands of the siRNA molecules according to the present invention preferably comprise between 15 and 29 nt, more preferably between 17 and 23 nt, and particularly 19 to 21 nt. These figures refer to the double-stranded part of the siRNA molecule. To this double stranded part there is added a so-called "overhang", which means one or more unpaired bases at the 3' and/or 5' end of the sense and/or antisense strands of the siRNA molecule of the present invention. The double-stranded part of the siRNA is also referred to as the "core" region of the siRNA.

According to one specific embodiment, the siRNA molecule of the present invention comprises in the sense strand, particularly at the 5' end of the sense strand, at least one modification (a), (b), or (c).

According to a further specific embodiment, the siRNA molecule according to the present invention comprises in the antisense strand, particularly at the 5' end of the antisense strand, at least one modification (a), (b), or (c).

According to a further preferred embodiment, the siRNA according to the present invention has no overhang at the 5' end of the antisense strand and/or the 5' end of the sense strand.

According to a still further embodiment, the siRNA according to the present invention has an overhang at the 3' end of the antisense strand and/or the 3' end of the sense strand. If the siRNA according to the present invention does comprise an overhang at the 3' end of the antisense strand, then the overhang residue or overhang residues comprise preferably at least one modification selected from (a) to (e).

Moreover, the siRNA according to the present invention preferably comprises at the 3' end of the sense strand an overhang, the overhang comprising at least one modification (c).

A further preferred embodiment of the siRNA molecule according to the present invention comprises in at least one of the core nucleotides of the sense strand and/or the antisense strand a modification (a), (b) or (d).

Preferably, the overhang of the sense strand and/or the antisense strand of the siRNA molecule according to the present invention comprises two modified nucleosides.

According to a still further preferred embodiment, the sense strand of the siRNA molecule according to the present invention has an overhang of two modified nucleotides at the 3' end, said modifications being (c), and the 3' end of the core of the sense strand has at least one modification (a) or (b), and the modification of the overhang at the 5' end of the sense strand is selected from (a) or (b), and the 5' core end of the sense strand has no modification, and the antisense strand has an overhang of two modified nucleotides at the 3' end, the modification being selected from (b), (c), or a combination of (b) and (e), and the antisense strand has no overhang at the 5' end, and the antisense strand has no modification at the 3' end of the core, and the core of the 5' end of the antisense strand comprises a modification (a) and/or (b), preferably (a).

If the siRNA molecule according to the present invention comprises the modification (c), then the nucleobase is preferably selected from the group consisting of adenine, cytosine, guanine, thymine, and uracil, preferably uracil.

If the siRNA molecule according to the present invention comprises the modification (d), then the nucleobase is preferably selected from the group consisting of adenine, cytosine, guanine, and uracil.

In a further preferred embodiment of the siRNA molecule according to the present invention the overhang residue according to modification (c) is one according to formula Va or Vb FORMULA Va

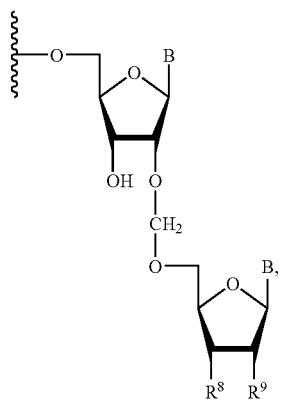

FORMULA Vb

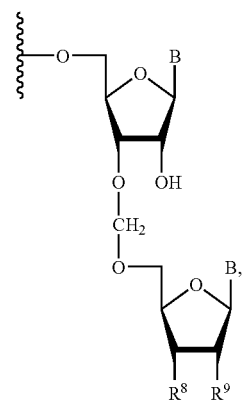

wherein B is a nucleobase preferably selected from the group consisting of adenine, cytosine, guanine, thymine or uracil and derivatives thereof, and preferably is uracil or a derivative thereof. $R^8$ is selected from the group consisting of H, OH, OCH$_3$, or an alkyloxy group, wherein the alkyl chain in the alkyloxy group may contain one or more heteroatoms or heteroatom groups, said heteroatoms or heteroatom group preferably being selected from the group consisting of O, S, or NH, and preferably is O. $R^9$ is selected from the group consisting of H, OH, OCH$_3$, or an alkyloxy group, wherein the alkyl chain in the alkyloxy group may contain one or more heteroatoms or heteroatom groups, said heteroatoms or heteroatom groups preferably being selected from the group consisting of O, S, or NH, and preferably is O. If in the compounds according to formulas Va and Vb $R^8$ and $R^9$ is H, only one of the groups $R^8$ and $R^9$ is H, thereby forming a T- or 3'-deoxy-modified nucleoside. In a further embodiment either $R^8$ or $R^9$ is OCH$_3$ and $R^9$ or $R^8$, respectively, is OH, thereby forming a T- or 3'-methoxy modified nucleoside. If $R^8$ and/or $R^9$ is an alkoxy group, the alkoxy group can be one having the following chemical structure: O—(CH$_2$)$_r$—(Y—CH$_2$)$_S$—CH$_3$ wherein Y is a heteroatom or heteroatom groups selected from O, S, and NH. Preferably, Y is O. r is an integer in the range from 1 to 12, preferably 1 to 5, most preferably 1 or 2, s is an integer in the range from O to 10, preferably 0 to 5 and most preferably is 0.

In a preferred embodiment of the siRNA molecule according to the present invention, $R^8$ is selected from H, OH, and OCH$_3$, and preferably is OH, and $R^9$ is selected from H, OH and OCH$_3$, and preferably is OH.

In yet a further preferred embodiment of the siRNA molecule according to the invention the core nucleotide comprising the modification (d) is a nucleotide having a chemical structure according to formula VI

FORMULA VI

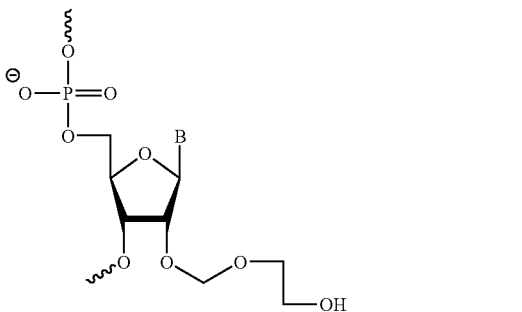

wherein B is a nucleobase or derivative thereof, preferably selected from the group consisting of adenine, cytosine, thymine, guanine, and uracil.

In yet another embodiment of the siRNA molecule according to the present invention, the overhang residue according to modification (e) is one according to formula VIIIa or VIIb FORMULA VIIa

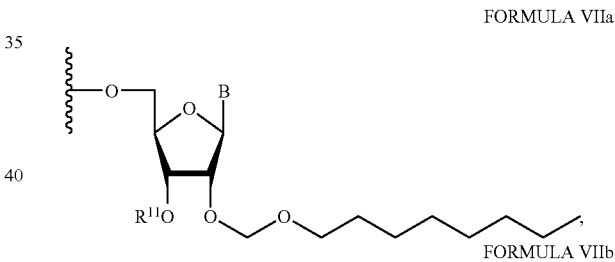

FORMULA VIIb

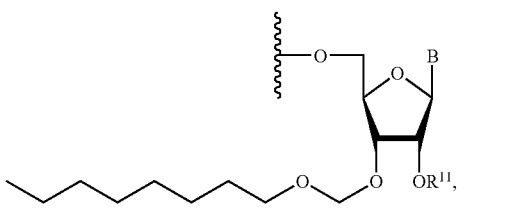

wherein B is a nucleobase preferably selected from the group consisting of adenine, cytosine, guanine, thymine or uracil and derivatives thereof, and preferably is uracil or a derivative thereof, $R^{11}$ is selected from the group consisting of H, CH$_3$ or OR$^{11}$ forms an alkyloxy group, wherein the alkyl chain in the alkyloxy group may contain one or more heteroatoms or heteroatom groups, said heteroatoms or heteroatom groups preferably being selected from the group consisting of O, S, or NH, and preferably is O, and $R^{11}$ preferably is H. The alkyloxy group can be of the same nature as outlined above with reference to Formulas Va and Vb.

If the siRNA molecule according to the present invention comprises one the modification (e), then the nucleobase is preferably uracil.

The modified siRNAs according to the present invention are stabilized by means of end-modifications of backbone phosphates or sugars. This requires one minimum changes in the core sequence of the sense strand of the siRNA molecule, and as a consequence, there are even less changes in the core of the antisense strand, which avoids inactivation of the antisense strand and avoids interference with the RNAi mechanism, and additional off target effects. The modification on the sense strand inactivates this strand, and therefore there are less off target effects, which are normally caused by the sense strand's "false" activity.

According to the present invention, siRNA was chemically modified using different types of modifications. Particularly, the ends (overhang(s) and/or core end(s)) of the siRNA of the present invention were modified. The sense strand of the siRNA carries modifications that stabilize the siRNA against nuclease cleavage and simultaneously inactivate it, in order to minimize off target effects. The antisense strand is also modified for enhanced serum stability, but to a degree, which does not affect the siRNA activity, hi addition, the combination of these modifications on sense and antisense strands enhance the activity of the siRNA in the tested cases, probably by partially changing the thermodynamic stability of duplex.

With the modifications according to the present invention, siRNAs were obtained which are more stable against serum nucleases and more efficient in inducing gene silencing at the same time. The longevity of these siRNA is also enhanced by these modifications. Moreover, the modifications on the sense strand lead to inactivation of this strand, following minimization of the induced off target effects. Due to higher effectiveness of these new modified siRNA, less siRNA is necessary for efficient gene silencing, and this minimizes also off target and toxic effects in the cells.

In a further aspect the present invention provides a solid support material suitable for the automated synthesis of nucleic acids, preferably oligoribonucleotides, comprising:

a) a solid phase material, b) a chemical group selected from the groups according to Formulas Ia, Ib, VIIIa or VIIIb which is bonded to the solid phase material via a linker group L:

FORMULA Ia

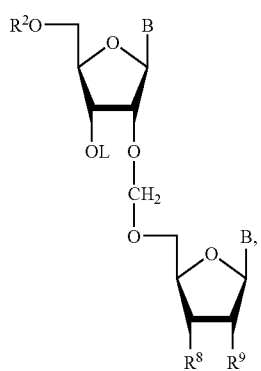

FORMULA Ib

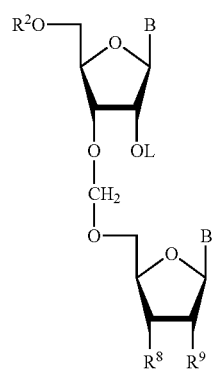

FORMULA VIIIa

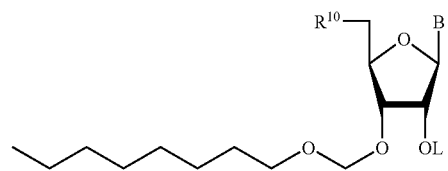

FORMULA VIIIb

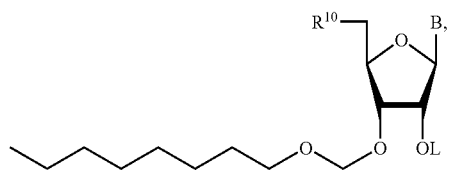

and wherein B is a nucleobase group preferably independently selected from the group consisting of adenine, cytosine, thymine, guanine and uracil or derivatives thereof. Nucleobase derivatives are here understood to include especially derivatives in which the nucleophilic $NH_2$ groups of adenine, guanine, thymine and cytosine are masked, typically by acylation. For the synthesis of oligoribonucleotides adenine, cytosine, guanine and uracil or derivatives thereof are of course preferred. In formulas Ia, Ib, VIIIa and VIIb $R^2$ and $R^{10}$, respectively, are a protective group selected from the group consisting of 4,4'-dimethoxytrityl, 4-methoxytrityl or silyl. $R^8$ is a group selected from H, OH, $OCH_3$, or an alkyloxy group, wherein the alkyl chain in the alkyloxy group may contain one or more heteroatoms or heteroatom groups, said heteroatoms or heteroatom groups preferably being selected from the group consisting of O, S, or NH, and preferably is O. Regarding the nature of the alkyloxy group, the same applies as outlined above with reference to the alkyloxy group in formulas Va and Vb. Alternatively $R^8$ is $OR^3$, wherein $R^3$ is a protective group selected from the group consisting of acyl groups, silyl groups or trialkylsilyloxymethyl groups. $R^9$ is a group selected from H, OH, $OCH_3$, or an alkyloxy group, wherein the alkyl chain in the alkyloxy group may contain one or more heteroatoms or heteroatom groups, said heteroatoms or heteroatom groups preferably being selected from the group consisting of O, S, or NH, and preferably is O. Again, regarding the nature of the alkyloxy group, the same applies as outlined above with reference to the alkoxy group in formulas Va or Vb. Alternatively, $R^9$ is $OR^1$, wherein $R^1$ is a protective group selected from the group consisting of acyl groups, silyl groups or trialkylsilyloxymethyl groups. In formulas Ia and Ib, if $R^8$ or $R^9$ is H, only one of $R^8$ and $R^9$ is H. The use of the protective groups $R^1$ and $R^3$ is of course preferred when the nucleosides incorporated into an oligonucleotide are intended to be T- or 3-hydroxyl substituted nucleosides. Accordingly, in a preferred embodiment of the support material of the present invention $R^8$ and $R^9$ are $OR^1$ and $OR^3$, wherein $R^1$ and $R^3$ are protective groups selected from the group consisting of acyl groups, silyl groups or trialkylsilyloxymethyl groups. Suitable acyl groups for use as $R^1$ and/or $R^3$ are for instance acetyl groups, benzoyl groups etc. Suitable silyl groups for use as $R^1$ and $R^3$ include triethylsilyl or dimethyltertbutylsilyl groups, etc. In principle, all protective groups can be used, which are cleaved off during deprotection of the oligonucleotides with $MeNH_2$ $OrNH_3$. The nature of the protective groups selected as $R^2$, $R^1$ and $R^3$ may to some extend depend of the reactivity of each of the respective protective groups. If, for instance, $R^2$ is selected to be a silyl group, then $R^1$ and $R^3$ are preferably not a silyl group.

In a preferred embodiment of this aspect of the invention, the chemical group in the support material is one according to formulas Ia or Ib, $R^9$ is $OR^1$ wherein $R^1$ is benzoyl (Bz), $R^2$ is 4,4'-(dimethoxy)trityl (DMT), and $R^8$ is $OR^3$ wherein $R^3$ is (triisopropysilyl)oxymethyl (TOM). This combination of protective groups on the respective hydroxy groups is especially suitable for carrying out automated nucleic acid synthesis using standard equipment and procedures known in the art, for instance those described by S. Pitsch, P. A. Weiss, L. Jenny, A. Stutz and X. Wu in *Helv. CUm. Acta* 2001, 84, 3113-3795.

In a further embodiment of this aspect of the invention, the chemical group in the support material is one according to formulas VIIIa or VIIIb, and $R^{10}$ is 4,4'(dimethoxy)trityl.

In a preferred embodiment of this aspect of the present invention, the nucleobase group B in any one of the chemical groups according to formulas Ia, Ib, VIIIa or VIIIb is uracil. The selection of the respective nucleobase group will of course depend on the nucleotide which is to be introduced into the nucleic acid, especially the oligoribonucleotide.

In a further preferred embodiment the solid phase material in the support material according to the invention is controlled pore glass (CPG), preferably having a pore size in the range between 100 to 1500 A, most preferably from 500 to 1000 A. Preferably, the CPG-based support material is functionalized with aminoalkyl groups, which can form a chemical bond, for instance an amide bond, with the linker group L in the chemical groups contained in Formulas Ia and Ib. Other suitable solid phase materials are polystyrene and surfaces. In yet a further embodiment of the support material according to the present invention, the linker group L is a —C(O) $(CH_2)_n$—C(O)O— group, wherein n is an integer from 1 to 10, preferably from 2 to 5, and most preferably is 2 or 5. The OL-moiety bonded to the polysaccharide moiety therefore preferably forms a dicarboxylate group, preferably a succinate group, (—O(O)CCH2CH2C(O)O—) or diheptandioate group, (—O(O)C(CH$_2$)$_5$C(O)O—), and most preferably a diheptandioate group (—O(O)C(CH$_2$)$_5$C(O)O—). A preferred loading of the support material with compounds according to Formulas Ia Ib, VIIIa or VIIIb on the material is in the range of 10 to 50 μmol/g, preferably in the range of 30 to 40 μmol/g.

The support materials according to the present invention provide a means for introducing specific modifications at the 3'- or 5'-ends of a respective nucleic acid. In the synthesis of the nucleic acid, which is preferably automated, appropriately activated and protected nucleotide building blocks are added stepwise to the chemical groups attached to the solid phase until the desired sequence has been obtained. By using the solid support of the present invention, it is possible to prepare nucleic acids, especially oligoribonucleotides, having modified end groups derived from the chemical groups according to Formulas Ia Ib, VIIIa or VIIIb comprised in the solid support material, i.e. either 2'-5'-formacetal linked nucleosides, 3'-5'-formacetal linked nucleosides or nucleosides having a 2'O- or 3'0-octyloxymethyl modified nucleosides. Preferably, the nucleobase in these nucleosides is uracil.

In a further aspect, the present invention provides compounds according to Formulas Ha, lib, IXa or UXb as shown below. These compounds can be used for the synthesis of the solid support materials discussed above. In the compounds according to Formulas Ha, lib, IXa or IXb

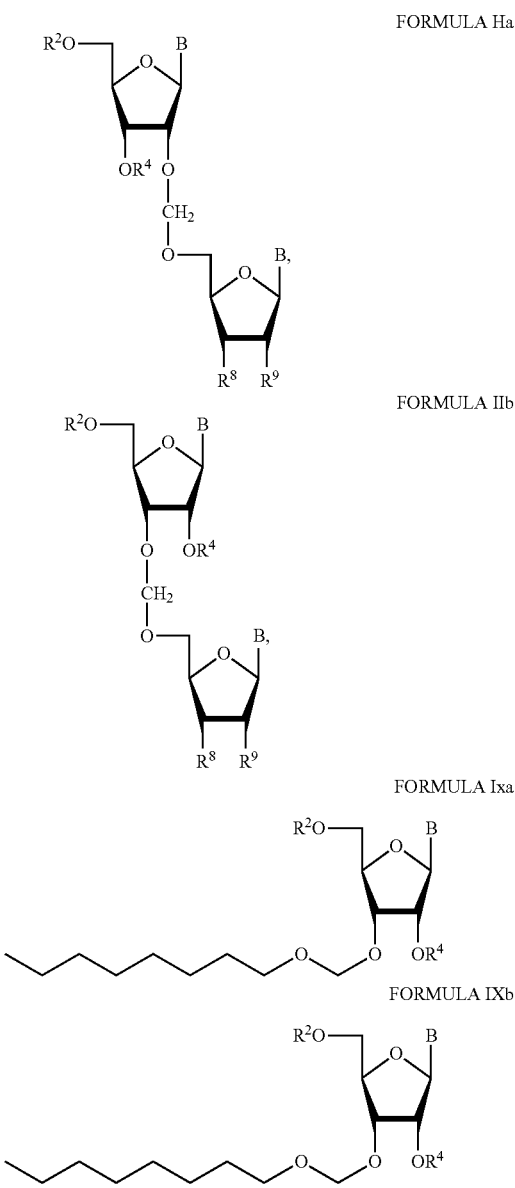

FORMULA Ha

FORMULA IIb

FORMULA Ixa

FORMULA IXb

In formulas IIa, IIb, IXa and IXb, B is a nucleobase group or derivative thereof, preferably independently selected from the group consisting of adenine, cytosine, thymine, guanine and uracil or derivatives thereof, wherein for the synthesis of oligoribonucleotides adenine, cytosine, guanine and uracil or derivatives thereof are preferred. Uracil or derivatives thereof are especially preferred.

$R^2$ is a protective group selected from the group consisting of 4,4'-(dimethoxy)trityl, 4-(methoxy)trityl or silyl. $R^8$ is a group selected from H, OH, $OCH_3$, or an alkyloxy group, wherein the alkyl chain in the alkyloxy group may contain one or more heteroatoms or heteroatom groups, said heteroatoms or heteroatom groups preferably being selected from the group consisting of O, S, or NH, and preferably is O. Regarding the nature of the alkyloxy group, the same applies as outlined with reference to the alkyloxy group in formulas Va and Vb. Alternatively, $R^8$ is $OR^3$, wherein $R^3$ is a protective group selected from the group consisting of acyl groups, silyl groups or trialkylsilyloxymethyl groups. $R^9$ is a group selected from H, OH, $OCH_3$, or an alkyloxy group, wherein the alkyl chain in the alkyloxy group may contain one or more heteroatoms or heteroatom groups, said heteroatoms or heteroatom groups preferably being selected from the group consisting of O, S, or NH, and preferably is O. Again, regarding the nature of the alkyloxy group, the same applies as outlined above with reference to the alkyloxy group in formulas Va and Vb. Alternatively, $R^9$ is $OR^1$, wherein $R^1$ is a protective group selected from the group consisting of acyl groups, silyl groups or trialkylsilyloxymethyl groups. The provisio applies that if $R^8$ or $R^9$ is H, only one of $R^8$ and $R^9$ is H Regarding the selection and nature of the groups $R^2$, $R^8$, $R^9$, $R^1$ and $R^3$, the same applies as outlined with reference to the support materials according to formulas Ia and Ib.

$R^4$ is selected from the group consisting of H and —C(O)$(CH_2)_n C(O)O$—$R^5$, wherein $R^5$ is a group selected nitrophenyl, tetrafluorophenyl, pentafluorophenyl and H, and n is an integer in the range from 1 to 10. n is preferably an integer in the range form 2 to 5 and preferably is 2 or 5. To attach these compounds to the solid phase material, a chemical bond must be provided between the solid phase material and the chemical compounds according to Formulas IIa, IIb, IXa or IXb. This bond is achieved either by first attaching a linker group at the 2'-0 or 3'-0 position on the nucleoside carrying the $OR^4$ group, if $R^4$ is —H, and then bonding the linker to the solid phase material which preferable comprises functional groups capable of reacting with the linker group.

In a preferred embodiment of these compounds according to the invention, the compound is one according to formula IIa or IIb, B is uracil, $R^9$ is $OR^1$ wherein $R^1$ is benzoyl (Bz), $R^2$ is 4,4'-(dimethoxy)trityl (DMT), $R^8$ is $OR^3$ wherein $R^3$ is (triisopropysilyl)oxymethyl (TOM), $R^4$ is —C(O)$(CH_2)_n C$(O)O—$R^5$ and n is an integer in the range from 2 to 5 and preferably is 2 or 5, wherein $R^5$ is 4-nitrophenyl. In this case, the compounds already comprise the linker group. In an other preferred embodiment, the compound is one according to formula IIa or IIb, B is uracil, $R^9$ is $OR^1$ wherein $R^1$ is benzoyl (Bz), $R^2$ is 4,4'-(dimethoxy)trityl (DMT), $R^8$ is $OR^3$, wherein $R^3$ is (triisopropysilyl)oxymethyl (TOM), and $R^4$ is H. In this case, a linker group is preferably attached to the compound, prior to attaching it to the solid phase material.

In a further preferred embodiment of the compounds according to the present invention, the compound is one according to formula IXa or Ixb and B is preferably selected from the group consisting of adenine, cytosine thymine, guanine and uracil, preferably from adenine, cytosine, guanine and uracil, and most preferably B is uracil. In this embodiment, $R^2$ preferably is 4,4'-(Dimethoxy)trityl (DMT), and $R^4$ is preferably selected from H or —C(O)$(CH_2)_n C(O)O$—$R^5$, wherein n is an integer in the range from 2 to 5 and preferably is 2 or 5, and wherein $R^5$ is 4-nitrophenyl.

In a further aspect the present invention provides specially modified phosphoramidites which can be used for the syntheses of nucleic acids. These phosphoramidites enable the introduction of specially modified nucleosides into nucleic acids, especially into oligoribonucleotides. These phosphoramidites are represented by the general formula III below.

FORMULA III

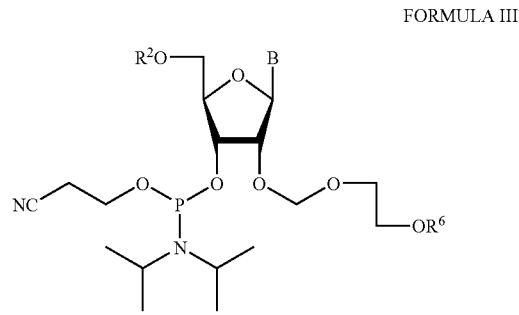

In formula III, B is a nucleobase or derivative thereof, which is preferably selected from the group consisting of adenine, cytosine, thymine, guanine and uracil, wherein adenine, cytosine, guanine and uracil or derivatives thereof are preferred. $R^2$ is a protective group, preferably $R^2$ is a 4,4'-(dimethoxy)trityl group, 4-(methoxy)trityl group or a silyl group. This protective group is selected in such a manner that it can be activated in respective nucleic acid syntheses to enable formation of a 5'-3'-linkage to a further nucleotide. $R^6$ is an acyl group, silyl group or trialkylsilyloxymethyl group. As discussed before, suitable acyl groups include acetyl and benzoyl groups, etc. Suitable silyl groups include triethylsilyl or dimethyltertbutylsilyl groups, etc. In preferred embodiments of the phosphoramidites according to the invention, B is selected from the group consisting of $N^6$-Acetlyadenine, $N^4$-acetylcytosine, $N^2$-acetylguanine and uracil. $R^2$ preferably is 4,4'-(dimethoxy)trityl. Preferably, $R^5$ is a benzoyl group.

The phosphoramidites according to the present invention can be used in the synthesis of nucleic acids, such as oligoribonucleotides, preferably in automated synthesis using standard procedures and equipment. The phosphoramidites can either be used with conventional solid support materials or with the specially modified solid support material according to the present invention. The phosphoramidites can for instance be used in combination with 2'-O-tom-protected ribonucleoside phosphoramidites as described by S. Pitsch, P. A. Weiss, L. Jenny, A. Stutz and X. Wu in *Helv. CHm. Acta* 2001, 84, 3773-3795. They allow the introduction of 2'-acetal modified ribonucleotides into oligoribonucleotides.

General

Reagents and solvents (highest purity) were from various suppliers and used without further purification, unless otherwise stated. 2'-O-tom-protected ribonucleoside phosphoramidites were prepared according to S. Pitsch, P. A. Weiss, L. Jenny, A. Stutz, X. Wu, *Helv. CMm. Acta* 2001, 84, 3112>. Work-up implies partitioning of the reaction mixture between $CH_2Cl_2$ and saturated aqueous $NaHCO_3$ solution, drying of the organic layer ($MgSO_4$), and evaporation. TLC: pre-coated silica-gel plates from Merck, stained by dipping into a solution of anisaldehyde (10 ml), $H_2SO_4$ (10 ml), and AcOH (20 ml) in EtOH (180 ml). and subsequent heating with a heat gun. CC (column chromatography): silica gel 60 (230-400 mesh) from Fluka. Anion-exchange (AE) HPLC: DNAPAC PA-100 (9.0×250 mm; Dionex), flow 2.5 ml/min; eluant A: 12 mM Tris. HCl (pH 7.4), 6 M urea; eluant B: 12 mM Tris. HCl (pH 7.4), 0.5 M $NaClO_4$, 6 M urea; detection at 260 nm, elution at 85° C. NMR (Bruker instrument): chemical shift δ in ppm relative to external standards ($^1$H and $^{13}$C: $Me_4Si$);

coupling constants J in Hz. MALDI-MS (linear negative mode): Axima CFR Plus (Kratos/Shimadzu); matrix: 2,4,6-trihydroxyacetophenone, diammonium citrate; m/z (rel. intensity in %). Acrylamide solution (30%): 300 g acrylamide, 8 g NJST-methylendiacrylamide; final volume: 1 1 H$_2$O. 10×TBE (Tris acid Boric EDTA): 54 g Tris base, 27.5 g Boric acid, 20 ml 0.5 M EDTA pH 8, final volume 500 ml (complete with water). Native 1×TBE 12% polyacrylamide gel: 6 ml Acrylamid solution (30%), 3 ml 5×TBE, 5 ml H$_2$O, 150 µl APS and 20 µl TEMED.

Multistep-Preparation of Support Materials

Preferred embodiments of the support material according to the present invention can be prepared according to the synthetic route outlined below in reaction scheme 1.

Synthesis of 2

To a solution of 1 (5.2 g, 7.11 mmol, prepared according to S. Pitsch, P. A. Weiss, L. Jenny, A. Stutz, X. Wu, *Helv. CMm. Acta*, 2001, 84, 3773) in pyridine (45 ml) was added benzoyl chloride (989 µl, 8.53 mmol). The resulting reaction mixture was stirred at room temperature overnight. After work-up, the crude product was dissolved in CH$_2$Cl$_2$ (50 ml) and dichloroacetic acid (5 ml) was added. 5 min later the reaction was complete; 3 ml methanol were then added. After work-up and recristallisation in hexane/CH$_2$Cl$_2$ 1:1, a colorless solid 2 (2.95 g 78%) was obtained. TLC (AcOEt/hexane 1:1): Rf 0.35. $^1$H-NMR (400 MHz, CDCl$_3$): 1.02-1.04 (m, $^i$Pr$_3$Si); 3.94 (dd, J=2.3, 11.3, H—C(5')); 4.05 (dd, J=2.3, 11.3, H—C(S$^i$)); 4.37 (m, H—C(4')); 4.72 (t, J=5.4, H—C(2')); 4.91, Reaction scheme 1: Multi-step preparation of support materials

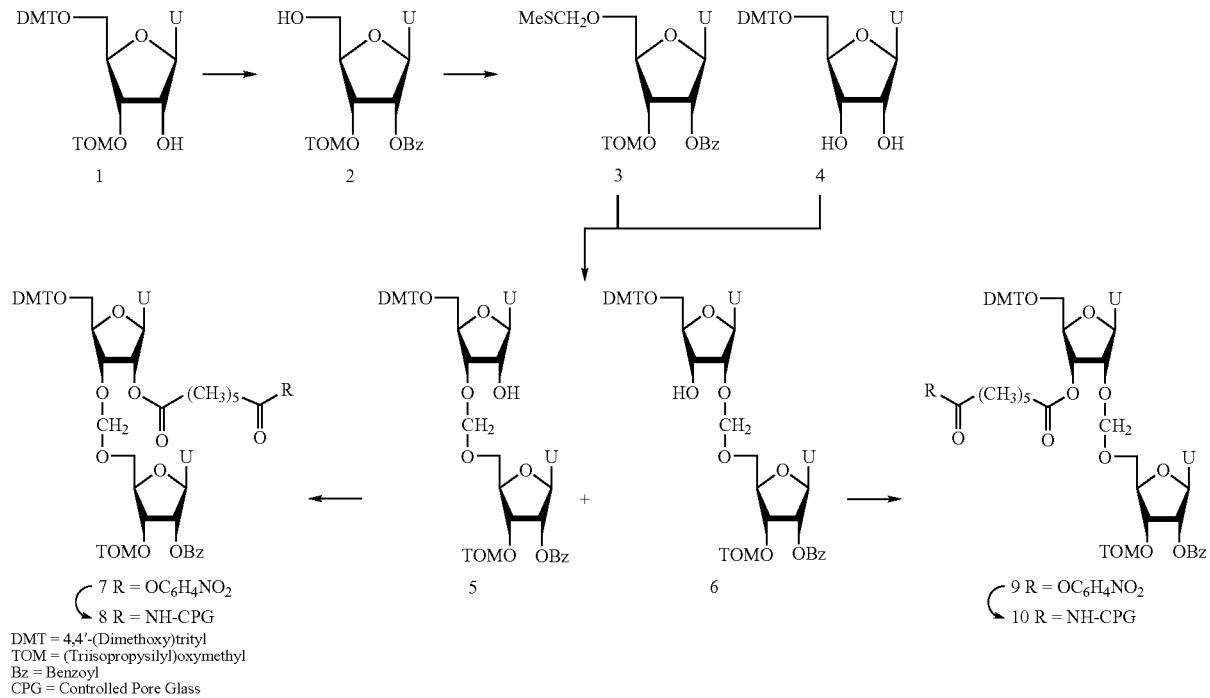

DMT = 4,4'-(Dimethoxy)trityl
TOM = (Triisopropysilyl)oxymethyl
Bz = Benzoyl
CPG = Controlled Pore Glass According to this reaction scheme in a first synthetic step (1→2) the 5'-O—, and 3'-O-protected uridine is deprotected in 5'-O-position and the previously non-protected 2'-O-position is protected with a suitable protecting group, which can withstand the reaction conditions required for the subsequent reaction steps. In the second synthetic step (2→3) a suitable reactive group for forming an formacetal linkage is introduced at the 5'-O-position of compound 2. This group is preferably a MeSCH$_2$— group. Functionalized compound 3 is subsequently reacted with the 5'-O-protected uridine 4 in step 3 (3+4→5 and 6), forming the 3'-5'- or 2'-5' formacetal linked compounds 5 and 6. In subsequent synthetic steps, 4a (5→7) and 4b(6→9), preferably carried out after separation of the regioisomers 5 and 6 a linker group is bonded to the non-protected 2'-OH or 3'-OH group of compounds 7 or 9, respectively. Finally, in synthetic steps 5a (7→8) or Sb (9→10), the compounds are bonded to the solid phase material via the linker group.

A preferred embodiment of this general reaction sequence in outlined in the following specific preparation steps.

5.08 (2d, J=5.0. OCH$_2$O); 5.57 (t, J=5.2, H—C(3')); 5.78 (d, J=8.1, H—C(5)); 6.07 (d, J=5.1, H—C(I')); 7.45-7.70 (m, 5 arom. H); 8.08 (d, J=8.3, H—C(O)); 8.26 (br. s, H—N(3)).

Synthesis of 3

2 (2.95 g, 5.52 mmol) was dissolved in a 1:1:1 solution of DMSO (7 ml)/Ac$_2$O (7 ml)/AcOH (7 ml) and the reaction mixture was stirred 3 days at room temperature. After work-up with hexane/AcOEt 1:1 as organic layer and CC (50 g of SiO$_2$, AcOEt/hexane 1:9→AcOEt/hexane 6:4), a colorless solid 3 (1.85 g, 56%) was obtained. TLC (AcOEt/hexane 1:1): Rf 0.55. $^1$H-NMR (400 MHz, CDCl$_3$): 1.02-1.04 (m, $^i$Pr$_3$Si); 2.24 (s, SCH); 3.82 (dd, J=2.5, 10.7, H—C(5')); 3.91 (dd, J=2.2, 10.7, H—C(5')); 4.50 (m, H—C(4')); 4.60 (dd, J=3.7, 5.2, H—C(2')); 4.76 (d, J=5.5, 2H, OCH$_2$S); 4.87, 5.01 (2d, J=5.0, OCH$_2$O); 5.38 (t, J=5.6 H—C(3')); 5.85 (d, J=8.2, H—C(5)); 6.39 (d, J=6.0, H—C(I')); 7.44-7.57 (m, 2 arom. H); 7.60 (m, 1 arom. H); 7.81 (d, J=8.2, H—C(6)); 8.06 (m, 2 arom. H); 8.48 (br. s, H—N(3)).

Synthesis of 5 and 6

Step 1: To a solution of 3 (1.62 g, 2.72 mmol) and cyclohexene (5.44 mmol, 551 µl) in CH$_2$Cl$_2$ (11 ml) was added at −80° C. SO$_2$Cl$_2$ (2.99 mmol, 242 µl). After stirring 35 min at −80° C. and then 40 min at room temperature, the reaction mixture was evaporated under reduced pressure and dried 10 min at high vacuum.

Step 2: To a solution of 4 (1.76 g, 3.264 mmol) in acetonitrile (13 ml) was added di-tert-butyltin dichloride (1.09 g, 3.59 mmol) and diisopropylethylamine (2.23 ml, 13 mmol). After stirring 15 min at room temperature, the crude product from step 1, dissolved in acetonitrile (5 ml), was added to this mixture and stirred 8 h at room temperature. After workup, using AcOEt as organic layer, the two diastereoisomers were separated by 3 CC (50 g of $SiO_2$, AcOEt/hexane 5:5→AcOEt 100%, two time to column volume per gradient). Combined yield: 41%. (6/5:7/3)

Data of 5: TLC (AcOEt/hexane 95/5): j?/0.80. $^1$H-NMR (400 MHz, $CDCl_3$): 0.95-1.10 (m, $^iPr_3Si$); 3.57 (dd, J=2.3, 11.3, H—C($S^j$); 3.63 (dd, J=2.2, 11.2, H—C(S')); 3.80 (s, 2 MeO); 3.93-3.99 (m, 2H—C(S)); 4.10 (m, H—C(2')); 4.50 (m, H—C(2')); 4.49-4.65 (m, H—C(4'), H—C(3')); 4.85, 4.98 (2d, J=5.1, $OCH_2O$); 4.88, 5.37 (2d, J=6.8, $OCH_2O$); 5.35 (d, J=6.5, H—C(S)); 5.54 (d, J=6.9, H—C(5)); 5.94 (d, J=7.2, H—C(I')); 6.52 (d, J=7.0, H—C(I')); 6.84-6.90 (m, 4 arom. H); 7.26-7.40 (m, 12 arom. H); 7.87 (d, J=8.2, H—C(6)); 7.96-7.99 (m, 2 arom. H); 8.14 (d, J=8.2, H—C(6)); 10.21 (br. s, H—N(3)); 10.75 (br. s, H—N(3)). MS: fehlt Data of 6: TLC (AcOEt/hexane 95/5): i?/0.85 (2' isomer). $^1$H-NMR (400 MHz, $CDCl_3$): 0.95-1.10 (m, $^iPr_3Si$); 3.45 (dd, J=2.3, 11.3, H—C(5')); 3.58-3.67 (m, 2H—C(5')); 3.80 (s, 2 MeO); 3.87 (dd, J=3.1, 11.0, H—C(5')); 4.14-4.19 (m, 2H—C(4')); 4.20-4.26 (m, 2H—C(2')); 4.38 (m, H—C(3')); 4.83 (m, H—C(3')); 4.85, 4.89 (2d, J=6.8, $OCH_2O$); 4.91, 4.95 (2d, J=5.1, $OCH_2O$); 5.35 (d, J=8.0, H—C(5)); 5.58 (d, J=2.5, H—C(I')); 5.73 (d, J=7.9, H—C(5)); 5.83 (d, J=2.4, H—C(F)); 6.84-6.90 (m, 4 arom. H); 7.26-7.40 (m, 12 arom. H); −8.08, 7.62 (2m, 2 arom. H); 8.02 (d, J=8.2, H—C(6)); 8.06 (d, J=8.3, H—C(6)); 9.35 (br. s, H—N(3)); 9.55 (br. s, H—N(3)).

Synthesis of 7 and 9

Pimelic acid-dinitrophenylester (893 mg, 2.22 mmol) was dissolved in pyridine (3.7 ml). DMAP (22.6 mg, 0.18 mmol) and 5 or 6 (400 mg each, 0.37 mmol) were added. After stirring over night at room temperature, the mixture was evaporated and co-evaporated twice with toluene (20 ml). CC (10 g of $SiO_2$, AcOEt/hexane 3:7→AcOEt/hexane 6:4) gave 7 (243 mg, 46%) and 9 (250 mg, 48%), respectively. Colorless foams.

Data of 7: TLC (AcOEt/hexane 7:3): Rf 0.72. $^1$H-NMR (400 MHz, $CDCl_3$): 0.95-1.05 (m, $^iPr_3Si$); 1.47 (m, $CH_2$); 1.72 (m, $CH_2$); 1.79 (m. $CH_2$); 2.42 (t, J=7.4, $CH_2$); 2.62 (/, J=7.3, $CH_2$); 3.50 (dd, J=2.3, 10.7, H—C(5')); 3.58 (dd, J=2.2, 10.6, H—C(5')); 3.76 (dd, J=33, 11.2, H—C(5')); 3.80 (s, 2 MeO); 3.85 (dd, J=2.4, 11.1, H—C(S)); 4.27 (m, H—C(4')); 4.32 (m, H—C(4')); 4.49 (t, J=5.4, H—C(3')); 4.53 (t, J=4.7, H—C(3')); 4.76, 4.78 (2d, J=6.9, $OCH_2O$); 4.80, 4.92 (2d, J=5.0, $OCH_2O$); 5.31, 5.36 (2d, J=7.4, 2H—C(S)); 5.46 (t, J=5.1, H—C(2')); 5.67 (dd, J=2.1, 8.0, H—C(2'); 6.06 (d, J=5.1, H—C(I')); 6.14 (d, J=5.1, H—C(I')); 6.83-6.89 (m, 4 arom. H); 7.26-7.45 (m, 16 arom. H); 7.75 (d, J=8.1, H—C(6)); 8.05-8.07 (m, 2 arom. H); 8.26 (d, J=8.3, H—C(6)).

Data of 9: TLC (AcOEt/hexane 7:3): £/0.72. $^1$H-NMR (400 MHz, $CDCl_3$): 0.95-1.05 (m, $^iPr_3Si$); 1.46 (m, $CH_2$); 1.70 (m, $CH_2$); 1.77 (m. $CH_2$); 2.42 (t, J=7.6, $CH_2$); 2.62 (t, J=7.5, $CH_2$); 3.45 (dd, J=2.3, 11.1, H—C(5')); 3.64 (dd, J=2.3, 11.2, H—C($S^j$); 3.73 (dd, J=3.5, 10.8, H—C(5')); 3.80 (s, 2 MeO); 3.95 (dd, J=2.9, 10.8, H—C($S^j$); 4.30 (m, H—C(4')); 4.40 (m, H—C(4')); 4.63 (t, J=4.8, H—C(3')); 4.57 (dd, J=5.1, 5.3, H—C(3')); 4.83, 5.02 (2d, J=6.8, $OCH_2O$); 4.90, 4.97 (2d, J=5.0, $OCH_2O$); 5.32, 5.35 (2d, J=7.42H—C(5)); 5.48 (t, J=5.4, H—C(2')); 5.72 (dd, J=2.3, 8.2, H—C(2')); 6.10 (d, J=5.3, H—C(F)); 6.24 (d, J=4.3, H—C($I^j$); 6.84-6.90 (m, 4 arom. H); 7.26-7.40 (m, 16 arom. H); 7.90 (d, J=8.20, H—C(6)); 8.05-8.07 (m, 2 arom. H); 8.26 (d, J=8.3, H—C(6)).

Synthesis of Solid Supports 8 and 10

To a solution of the active ester 7 or 9 (0.13 mmol each) in DMF (4.16 ml) was added long-chain-alkylamino CPG (1.04 g) and then $^iPr_2NEt$ (0.4 ml). The mixture was shaken for 20 h at room temperature. After filtration, the solid support was washed with DMF and $CH_2Cl_2$, dried, suspended in pyridine (2.6 ml) and $Ac_2O$ (1.56 ml) and shaken for 2 h at room temperature. After filtration, the solid was washed with DMF and $CH_2Cl_2$, and dried under high vacuum. Typical loadings of the solid support were 30 μmol/g with 500-A CPG.

Reaction scheme 1.1: General synthesis of the 2'-5' coupled dimers

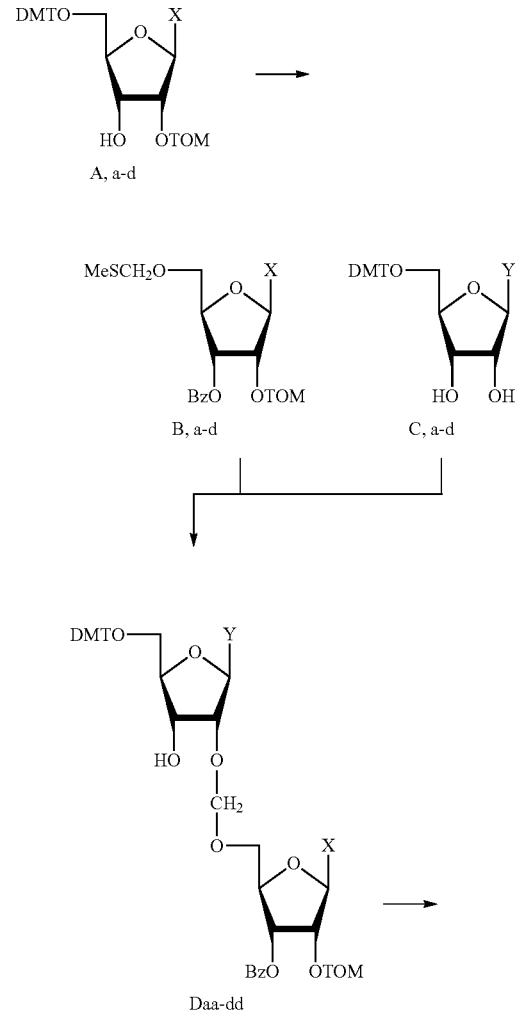

-continued

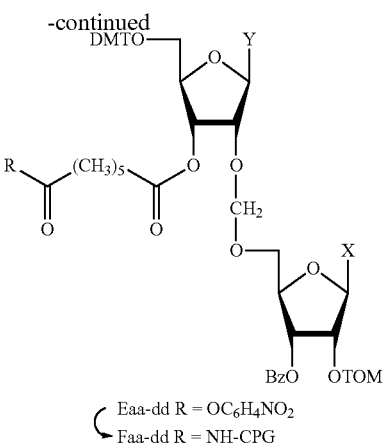

Eaa-dd R = OC₆H₄NO₂
Faa-dd R = NH-CPG

DMT = 4,4'-(Dimethoxy)trityl
TOM = (Triisopropysilyl)oxymethyl
Bz = Benzoyl
CPG = Controlled Pore Glass
X, Y =
a: Uracil
b: $N^4$-Acetylcytidine
c: $N^6$-Acetyladenine
d: $N^2$-Acetylguanine According to this reaction scheme in a first synthetic step (A,a-d→B,a-d; a-d stands for the four compounds containing the nucleobase derivatives uracil (a). $N^4$-acetylcytidine (b), $N^6$-acetyladenine (c) and $N^2$-acetylguanine (d)) the 5"-O—. and 2'-O-protected uridine is deprotected in 5'-O-position and the previously non-protected 2"-O-position is protected with a suitable protecting group. which can withstand the reaction conditions required for the subsequent reaction steps. followed by the introduction of a suitable reactive group for forming an formacetal linkage at the 5'-O·position. This group is preferably a MeSCH₂-groirp. Functionalized compound B,a-d is subsequently reacted with the 5'-O-protected nucleosides C,a-d in step 2 (B,a-d+C,a-(1→D,a-d), forming preferentially the 2"-5' formacetal linked compounds D,aa-dd (D,aa-dd stands for the 16 possible combinations of dinucleotides, each containing two of the nucleobase derivatives uracil (a), JVA-acetylcytidine (b), $N^6$-acetyladenine (c) and $N^2$-acetylguanine (d); the first descriptor refers to the nucleotide Y at the 5'-end (containing a 5'-0-DMT group) and the second to the nucleotide X at the 3'-end (containing a 3'-O-benzoyl group)). In the subsequent synthetic step 4 (D,aa-dd→E,aa-dd). carried out after isolation of the compound D,aa-dd. a linker group is bonded to the non-protected 3'-OH group of compounds E,aa-dd. Finally, in synthetic step 5 (E,aa-dd→F,aa-dd), the compounds are bonded to the solid phase material via the linker group.

The reaction conditions for this general reaction sequence in outlined in the following specific preparation steps.

Synthesis of Four Compounds B,a-d

To a solution of A,a-d (20 mmol. prepared according to S. Pitsch, P. A. Weiss. L. Jenny. A. Stutz, X. Wu, Helv CMm. Acta. 2001. 84. 3773) in pyridine (130 ml) was added benzoyl chloride (3 ml, 25 mmol). The resulting reaction mixture was stirred at room temperature overnight. After work-up, the crude product was dissolved in CH₂Cl₂ (150 ml) and dichloroacetic acid (15 ml) was added. 5 min later the reaction was complete; 15 ml methanol were then added. After work-up, the crude products were were dissolved in a 1:1:1 solution of DMSO (30 ml)/Ac2O (30 ml)/AcOH (30 ml) and the reaction mixture was stirred 3 days at room temperature. After work-up with hexane/AcOEt 1:1 as organic layer and CC (150 g of SiO₂), compounds B,a-d were obtained as colorless solids Data of B,a (uracil): Yield 75%. TLC (AcOEt/hexane VA): Rf 0.59. ¹H-NMR (400 MHz, CDCl₃): 1.02-1.04 (m, $^iPr_3Si$); 2.22 (s, SCH₃) 3.88-3.90 (m. H—C(S'), H—C(S")); 4.48 (m, H—C(4")); 4.69 (dd. J=5.2, 7.1, H—C(2'); 4.76 (dd. J=117, 18.1. OCH₂S); 4.92 (m. OCH₂O); 5.56 (dd, J=2.1, 5.2, H—C(3')); 5.79 (dd, J=2.1, 8.2, H—C(5)); 6.34 (d, J=7.2, H—C(1') 7.50 (m, 2 arom. H); 7.63 (m, 1 arom. H); 7.83 (d, J=8.3. H—C(6)); 8.12 (m, 2 arom. H); 8.45 (br, s, H—N(3)).

Data of B,b ($N^4$-acetylcytosine): Yield 60%. TLC (CH₂Cl₂/MeOH 19:1): Rf 0.62. ¹H-NMR (400 MHz, CDCl₃): ¹H-RMN (400 MHz, CDCl₃): 1.02-1.04 (m, $^iPr_3Si$); 2.23 (s, SCH₃); 2.35 (s, N—CH₃); 3.96 (m, H—(C-5')) 3.01 (m, H—C(5)); 4.57 (m, H—C(4')); 4.66 (1, J=5.0, H—C(2')); 4.76 (dd, J=7.5, 17.2, OCH₂S); 5.05 (dd, J=4.8, 8.7, OCH₂O); 5.48 (t, J=5.2, H—C(3')); 6.33 (d, J=5.2, H—C(1')); 7.45 (m, 3 arom. H); 7.62 (m, H—C(5)); 8.12 (m, 2 arom. H) 8.32 (d, J=7.5, H—C(6)).

Data of B,c ($N^6$-acetyladenine): Yield 55%. TLC(CH₂Cl₂/MeOH 19:1): Rf 0.67. ¹H-NMR (400 MHz, CDCl₃): [WIRD NACHGELIEFERT]

Data of B,d ($N^2$-acetylguanine): Yield 25%. TLC (CH₂Cl₂/MeOH 19:1): Rf 0.59. ¹H-NMR (400 MHz, CDCl₃): 1.03-1.05 (m, $^iPr_3Si$); 2.23 (s, SCH₃); 2.32 (s, N—CH₃); 3.85 (dd, J=3.3, 10.7, H—(C-5')); 3.96 (dd. J=3.6, 10.7, H—C(5')); 4.57 (m, H—C(4')); 4.76 (d, J=4.5. OCH₂S); 4.85, 4.90 (2d, J=5.1. OCH₂O); 5.17 (dd, J=5.1, 6.9. H—C(2')); 5.74 (dd, J=2.1, 5.1, H—C(3')); 6.10 (d, J=6.9. H—C(1')); 7.51 (m. 2 arom. H); 7.65 (m, 1 arom. H); 8.02 (s, H—C(8)); 8.13 (m. 2 arom. H).

Synthesis of Sixteen Compounds D,aa-dd

Step 1: To a solution of B,a-d (8 mmol) and cyclohexene (16 mmol, 1.65 ml) in CH₂Cl₂ (33 ml) was added at −80° C. SO₂Cl₂ (8 mmol, 0.6 ml). After stirring 35 min at −80° C. and then 40 min at room temperature, the reaction mixture was evaporated under reduced pressure and dried 10 min at high vacuum.

Step 2: To a solution of C,a-d (10 mmol) in 1,2-dichloroethane (39 ml) was added di-n-butyltin dichloride (3.2 g, 10.8 mmol) and diisopropylethylamine (3.7 ml, 39 mmol). After stirring 15 min at room temperature, the crude product from step 1, dissolved in 1,2-dichlorethane (15 ml), was added to this mixture and stirred 8 h at room temperature. After workup, using AcOEt as organic layer, the products were isolated by CC (150 g of SiO₂, AcOEt/hexane or CH₂Cl₂/MeOH gradients).

| Data of compounds D,aa-D,dd | | | | | | |
|---|---|---|---|---|---|---|
| Compound | Nucleoside on 5'-end | Nucleoside on 3'-end | Yield | $R_f$ value | m/z meas | m/z calc |
| D,aa | uracil | uracil | 35% | 0.85[1] | | 1093 |
| D,ab | uracil | $N^4$-acetylcytidine | 30% | 0.34[2] | | 1133 |
| D,ac | uracil | $N^6$-acetyladenine | 30% | 0.42[2] | | 1157 |

Data of compounds D,aa-D,dd

| Compound | Nucleoside on 5'-end | Nucleoside on 3'-end | Yield | $R_f$ value | m/z meas | m/z calc |
|---|---|---|---|---|---|---|
| D,ad | uracil | $N^2$-acetylguanine | 35% | 0.41[2] | | 1173 |
| D,ba | $N^4$-acetylcytidine | uracil | 20% | 0.56[1] | | 1133 |
| D,bb | $N^4$-acetylcytidine | $N^4$-acetylcytidine | 10% | 0.34[2] | | 1174 |
| D,bc | $N^4$-acetylcytidine | $N^6$-acetyladenine | 15% | 0.60[2] | | 1198 |
| D,bd | $N^4$-acetylcytidine | $N^2$-acetylguanine | 10% | 0.33[2] | | 1215 |
| D,ca | $N^6$-acetyladenine | uracil | 25% | 0.53[1] | | 1157 |
| D,cb | $N^6$-acetyladenine | $N^4$-acetylcytidine | 25% | 0.45[2] | | 1198 |
| D,cc | $N^6$-acetyladenine | $N^6$-acetyladenine | 25% | 0.57[2] | | 1223 |
| D,cd | $N^6$-acetyladenine | $N^2$-acetylguanine | 10% | 0.42[2] | | 1239 |
| D,da | $N^2$-acetylguanine | uracil | 25% | 0.27[1] | | 1173 |
| D,db | $N^2$-acetylguanine | $N^4$-acetylcytidme | 30% | 0.40[2] | | 1215 |
| D,dc | $N^2$-acetylguanine | $N^6$-acetyladenine | 35% | 0.46[2] | | 1239 |
| D,dd | $N^2$-acetylguanine | $N^2$-acetylguanine | 40% | 0.29[2] | | 1254 |

[1] AcOEt/hexane 19:1;
[2] $CH_2Cl_2$/MeOH 9:1

Synthesis of Sixteen Compounds E,aa-E,dd

Pimelic acid-dinitrophenylester (2.7 g, 6.5 mmol) was dissolved in pyridine (10 ml). DMAP (70 mg, 0.55 mmol) and compounds D,aa-D,dd (1 mmol each) were added. After stirring over night at room temperature, the mixture was evaporated and co-evaporated twice with toluene (50 ml). CC (30 g of SiO?. AcOEt/hexane gradients) gave compounds E,aa-E,dd in yields between 65% and 75%. Colorless foams.

Synthesis of Sixteen Solid Supports F,aa-F,dd

To a solution of the active esters E,aa-E,dd (0.4 mmol each) in DMF (12 ml) was added long-chain-alkylamino CPG (3 g, 500-A) and then $^iPr_2NEt$ (1.2 ml). The mixture was shaken for 20 h at room temperature. After filtration, the solid support was washed with DMF and $CH_2Cl_2$, dried, suspended in pyridine (8 ml) and $Ac_2O$ (4.5 ml) and shaken for 2 h at room temperature. After filtration, the solid was washed with DMF and $CH_2Cl_2$, and dried under high vacuum. Loadings of the sixteen solid supports F,aa-F,dd were between 30 and 50 μmol/g.

Multistep-Preparation of Phosphoramidites

Preferred embodiments of the phosphoramidites according to the present invention can be prepared according to the synthetic route outlined below in reaction scheme 2.

Reaction scheme 2: Preparation of phosphoramidites

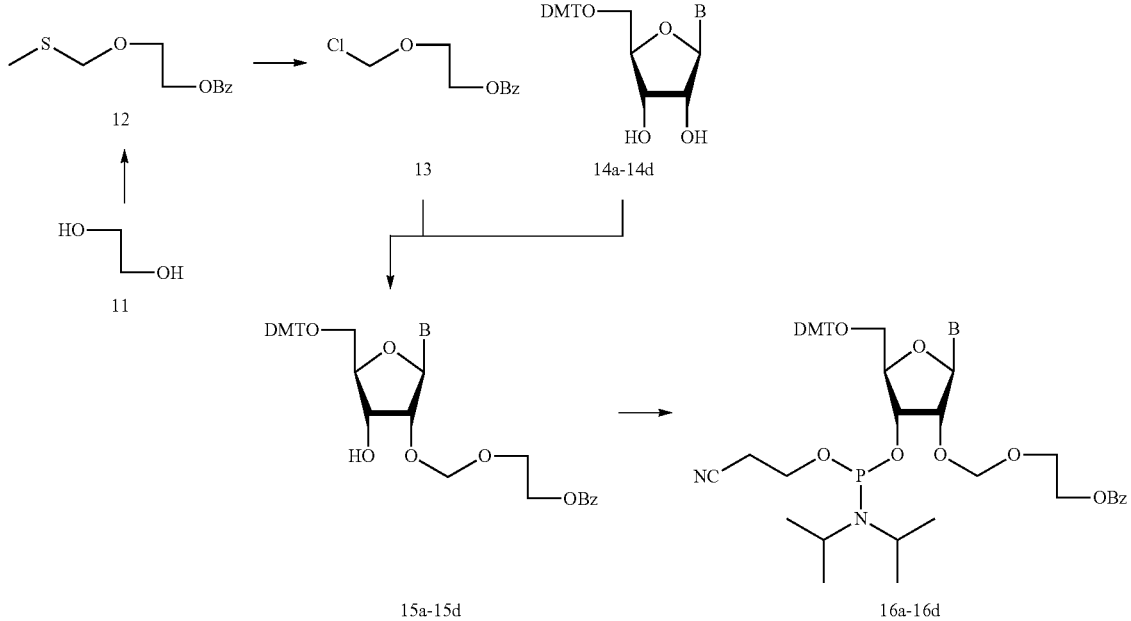

DMT = 4,4'-(Dimethoxy)trityl
Bz = Benzoyl
B =
a: $N^6$-Acetyladenine
b: $N^4$-Acetylcytosine
c: $N^2$-Acetylguanine
d: Uracile In synthetic step 1 (H→12) one of the two hydroxyl groups of ethylene glycol 11 is protected by a suitable protective group while the second hydroxyl group is reacted to give a functional thioacetal group. In subsequent step 2 (12→13), the thioacetal group reacted to yield chloromethylether 13. Subsequently, in step 3 (13+14→15a-15d), 5'-O-protected nucleosides 14a-14d (prepared according to S. Pitsch, P. A. Weiss, L. Jenny, A. Stutz, X. Wu, Helv. CMm. Acta, 2001, 84, 3773) are alkylated in the 2'-O-position to yield 2'-O-formacetal substituted nucleosides 15a-15d. Finally, in step 4 (15a-15d→16a-16d), nucleosides 15a-15d are reacted with diisopropylphosphoramidochlorodite in the 3'-0 position to yield phosphoramidites 16a-16d.

Synthesis of 12

Benzoyl chloride (2.3 ml, 20 mmol) was added dropwise to a solution of ethylene glycol (2.2 ml, 40 mmol) in pyridine (80 ml). After 1h of stirring the major part of the pyridine was evaporated. After usual work up, the residue was co-evaporated with 3×10 ml of toluene. The residue was dissolved in DMSO (20 ml), treated with AcOH (20 ml) and $Ac_2O$ (20 ml). After 1 day of stirring, the reaction mixture was poured in a well stirred mixture of 400 ml (AcOEt/Hexane 1:1) and 400 ml of $H_2O$. The organic phase was then extracted with 400 ml of sat. $NaHCO_3$, dried with $MgSO_4$ and evaporated. FC (100 g of $SiO_2$, AcOEt/hexane 5:95 to 15:85): 1 (2.47 g, 55%) as colorless oil. $R_f$ 0.58 (AcOEt/Hexane 2:8). $^1$H-NMR (400 MHz, $CDCl_3$): 2.15 (s, MeS); 3.89 (m, $SCH_2$); 4.50 (m, $CH_2O$); 4.71 (s, $SCH_2O$); 7.44 (m, 2H arom.); 7.56 (m, 1H arom.); 8.06 (m, 2H arom.). MS: 249.5 (100, [M+Na]$^+$).

Synthesis of Crude 13

At −78°, $SO_2Cl_2$ (0.39 ml, 4.9 mmol) was added dropwise to a stirred solution of 12 (1.00 g, 4.4 mmol) and cyclohexene (0.89 ml, 8.8 mmol) in $CH_2Cl_2$ (17.5 ml). After 30 min, the reaction mixture was allowed to warm up to room temperature and stirred for another 45 min. After evaporation of the solvent, the residue was dried under high vacuum for 15 min, dissolved in 1,2-dichloroethane and directly used for the alkylation reactions.

General Procedure for the Synthesis of Nucleosides 15a-d

To a solution of nucleosides 14a-d (1 eq) in 1,2-dichloroethane (0.25 M) were added successively ($^i$Pr)$_2$NEt (3.5 eq) and $Bu_2SnCl_2$ (1.2 eq). The reaction mixtures were stirred at room temperature for 30 min, heated to 70°, treated with the chloromethylether 13 (1.2 eq) and stirred for 30 min at 70°. The reaction mixtures were then subjected to usual work up. The organic phase was filtered through Celite, dried with $MgSO_4$ and evaporated. The residue was purified by FC.

Synthesis of 15a

According to the general procedure with 14a (1.20 g, 2.0 mmol) and crude 13. FC (25 g of $SiO_2$, AcOEt/hexane 5:5 to AcOEt then to AcOEt/MeOH 97:3): 15a (442 mg, 27%) as white foam. $R_f$ 0.38 (AcOEt). $^1$H-NMR (400 MHz, $CDCl_3$): 2.60 (s, MeCO); 2.90 (d, J=5.4, HO—(C3')>>; 3.44 (dd, J=4.0, 10.7, H—(C5')); 3.52 (dd, J=3.0, 10.7, H—(C5')); 3.79-3.84 (m, MeO, 1H $CH_2O$); 3.88-3.94 (m, 1H $CH_2O$); 4.26 (m, H—(C4'); 4.39-4.42 (m, $CH_2OBz$); 4.57 (m, H—(C3')>; 4.93-4.96 (m, $OCH_2O$, H—(C2')); 6.26 (d, J=4.4, H—(C1')); 6.79-6.83 (m, 4H arom.); 7.20-7.44 (m, 1lH arom); 7.52-7.57 (m, 1H arom); 7.99-8.02 (m, 2H arom); 8.18 (s, H—(C2)); 8.62 (s, H—(C8)); 8.82 (br, s, NHAC). MS: 789 (100, [Mj$^+$]); 811 (16, [MH—Na]$^+$).

Synthesis of 15b

According to the general procedure with 14b (1.17 g, 2.0 mmol) and crude 13. FC (25 g of $SiO_2$, AcOEt/hexane 5:5 to AcOEt then to AcOEt/MeOH 97:3): 15b (680 mg, 45%) as white foam. $R_f$ 0.57 ($CH_2Cl_2MeOH$ 9:1). $^1$H-NMR (400 MHz, $CDCl_3$): 2.21 (s, MeCO); 2.91 (d, J=9.2, HO—(C3')); 3.50 (dd, J=2.4, 11.2, H—(C5')); 3.55 (dd, J=2.0, 11.3, H—(C5')); 3.81 (s, 2 MeO); 3.92 (m, $CH_2O$); 3.99-4.08 (m, $CH_2O$, H—(C4')); 4.27 (d, J=4.27, H—(C2')); 4.35-4.49 (m, H—(C3')); 4.47-4.50 (m, $CH_2OBz$); 5.03, 5.22 (2d, J=6.6, $OCH_2O$); 5.98 (s, H—(C1')); 6.84-6.88. (m, 4H arom.); 7.08 (d, J=7.5; H—(C5)); 7.24-7.42 (m, H H arom.); 7.49-7.53 (m, 1H arom.); 8.01-8.05 (m, 2H arom.); 8.45 (d, J=7.5; H—(C6)); 9.18 (br, s, NHAc). MS: 765 (100, [M]$^+$); 787 (37, [M+Na]$^+$) 803 (20, [N+K]$^+$).

Synthesis of 15c

According to the general procedure with 14c (1.25 g, 2.0 mmol) and crude 13. FC (25 g of $SiO_2$, AcOEt/hexane 5:5 to AcOEt then to AcOEt/MeOH 97:3): 15c (840 mg, 54%) as white foam. $R_f$ 0.42 ($CH_2Cl_2MeOH$ 9:1). $^1$B-NMR (400 MHz, $CDCl_3$): 1.92 (s, MeCO); 3.24-3.30 (m, H—(C5'), HO—(C3'); 3.49 (dd, J=2.1, 10.7, H—(C5')); 3.74 (s, 2 MeO); 3.86 (m, $CH_2O$); 4.20 (m, H—(C4'); 4.40-4.55 (m, $CH_2OBz$, H—(C3'); 4.87 (m, OCH 20, H—(C2')); 6.01 (d, J=4.6, H—(C1∝)); 6.74-6.79 (m, 4H arom.); 7.14-7.54 (m, 12H arom); 7.85 (s, H—(C5)); 7.97 (m, 2H arom); 9.29 (br, s, NHAc); 12.02 (br, s H—(N1)). MS: 805 (100, [M]$^+$); 827 (24, [M+Na]$^+$).

Synthesis of 15d

According to the general procedure with 14d (1.09 g, 2.0 mmol) and crude 13. FC (25 g of $SiO_2$, AcOEt/hexane 2:8 to AcOEt): 15d (540 mg, 37%) as white foam. $R_f$ 0.72 (AcOEt). $^1$H-NMR (400 MHz, $CDCl_3$): 2.72 (d, J=8.3, OH—(C3')); 3.49 (dd, J=2.3, 11.0, H—(C5')); 3.53 (dd, J=2.2, 11.0, H—(C5')); 3.79 (s, 2 MeO); 3.90-4.05 (m, $CH_2O$, H—(C4'); 4.31 (dd, J=2.4, 5.2, H—(C2'); 4.45-4.55 (m, $CH_2OBz$, H—(C3'); 4.98, 5.09 (2d, J=6.8, $OCH_2O$); 5.29 (d, J=8.1, H—(C5)); 6.02 (d, J=2.4, H—(C1')); 6.85-6.89 (m, 4H arom.); 7.24-7.45 (m, HH arom); 7.54-7.58 (m, 1H arom); 7.95 (d, J=8.1, H—(C6)); 8.05-8.08 (m, 2H arom); 8.47 (br. s, H—(N3)). MS (Pos. Mode): 746 (100, [M+Na]); 762 (13. [M+K]$^+$)

General Procedure for the Synthesis of Phosphoramidites 16a-d

To a solution of the nucleosides 15a-d (1 eq) in $CH_2Cl_2$ (0.25 M) were added successively ($^i$Pr)$_2$NEt (2.5 eq) and diisopropylphosphoramidochloriditite (1.2 eq). The reaction mixtures were stirred for 14 h at room temperature and subjected to FC.

Synthesis of 16a

According to the general procedure with 15a (393 mg, 0.50 mmol). FC: (8 g of $SiO_2$, AcOEt/hexane 2:8 (+2% $NEt_3$) to AcOEt/hexane 8:2 (±2% $NEt_3$)): 16a (390 mg, 79%) as white foam (1:1 mixture of diastereoisomers). $R_f$ 0.70 (AcOEt). $^1$H-NMR (400 MHz, $CDCl_3$): 1.06 (d, 3H, J=6.8, NCH (Me)$_2$); 1.16-1.19 (m, 9H, NCH(Me)$_2$); 2.39 (t, J=6.4, $CH_2CN$); 2.59 (s, MeCO); 2.63 (t, J=6.4, $CH_2CN$); 3.37 (m, $POCH_2$); 3.50-3.94 (m, 2H—(C5'), MeO, $CH_2O$, NCH (Me)$_2$, $POCH_2$); 4.27-4.44 (m, H—(C4'), $CH_2OBz$); 4.70 (m, H—(C3'); 4.81-4.95 (m, $OCH_2O$); 5.11 (m, H—(C2')); 6.24, 6.26 (2d, J=6.4, H—(C1')); 6.79-6.82 (m, 4H arom.); 7.18-7.43 (m, H H arom); 7.52-7.56 (m, 1H arom); 7.96-7.98 (m, 2H arom); 8.18, 8.19 (2s, H—(C2)); 8.58 (br, s, NHAc); 8.60, 8.61 (2s, H—(C8)). MS: 990 (100, [M+H]$^+$).

Synthesis of 16b

According to the general procedure with 15b (579 mg, 0.76 mmol). FC: (11 g of $SiO_2$, AcOEt/hexane 2:8 (±2% $NEt_3$) to AcOEt/hexane 8:2 (+2% $NEt_3$)): 16b (662 mg, 90%) as white foam (1:1 mixture of diastereoisomers). $R_f$ 0.60 (AcOEt).). $^1$H-NMR (400 MHz, $CDCl_3$): 1.00 (d, 3H, J=6.8, NCH (Me)$_2$); 1.14-1.17 (m, 9H, NCH(Me)$_2$); 1.76, 1.85 (2s, MeCO); 2.32 (t, J=6.3, $CH_2CN$); 2.69 (dt, J=3.0, 6.6, $CH_2CN$); 3.34-3.62 (m, 2H—(C5'), NCH(Me)$_2$, 2H $POCH_2$);

3.702, 3.712, 3.715 (3s, MeO); 3.83-4.02 (m, CH$_2$O); 4.16-4.22 (m, H—(C4')); 4.27 (m, H—(C2'), 4.35-4.48 (m, H—(C3'), CH$_2$OBz); 4.92-5.02 (m, OCH$_2$O); 5.99 (s, H—(C1'); 6.73-6.78 (m, 4H arom.); 6.82, 6.90 (2d, J=7.5, H—(C5)); 7.16-7.34 (m, H H arom); 7.41-7.45 (m, IH arom); 7.92-7.96 (m, 2H arom); 8.34, 8.43 (2d, J=7.5, H—(Co)); 9.39, 9.51 (br, 2s, NHAc). MS: 966 (100, [MH-H]$^+$); 988 (25, [AfJ-Na]$^+$): 1005 (15, [JwfH-K]$^+$).

Synthesis of 16c

According to the general procedure with 15c (594 mg, 0.74 mmol). FC: (8 g of SiO$_2$ AcOEt/hexane 5:5 (+2% NEt 3) to AcOEt (+2% NEt 3)): 16c (590 mg, 80%) as white foam (1:1 mixture of diastereoisomers). R$_f$ 0.66 (AcOEt). $^1$H-NMR (400 MHz, CDCl$_3$): 1.00 (d, J=6.8, NCH(Me)$_2$); 1.14-1.17 (m, NCH(Me)$_2$); 1.76, 1.85 (2s, MeCO); 2.31 (t, J=6.3, CH$_2$CN); 2.69 (dt, J=2.9, 6.6, CH$_2$CN); 3.24 (m, POCH$_2$); 3.49-4.00 (m, 2H—(C5'), MeO, CH$_2$O, NCH(Me)$_2$, POCH$_2$); 4.27 (m, 0.5H—(C4')); 4.34-4.56 (m, 0.5H—(C4'), 0.5H—(C3'), CH$_2$OBz); 4.62 (m, 0.5H—(C3')); 4.78, 4.82, 4.85, 4.91 (4d, J=7.1 OCH 20); 5.07 (m, H—(C2')), 5.95, 6.01 (2d, J=5.2, 5.9, H—(C1'); 6.78-6.82 (m, 4H arom.); 7.16-7.59 (m, 13H arom); 7.864, 7.866 (2s, H—(C8)); 8.00-8.02 (m, 2H arom); 8.46, 8.76 (br, 2s, NHAc). MS: 1007 (100, [M+H]$^+$); 1028 (11. [M+Na]$^+$).

Synthesis of 16d

According to the general procedure with 15d (497 mg, 0.69 mmol). FC: (10 g of SiO$_2$ AcOEt/hexane 2:8 (+2% NEt 3) to AcOEt/hexane 6:4 (+2% NEt 3)): 16d (575 mg, 91%) as white foam (1:1 mixture of diastereoisomers). R$_f$ 0.87 (AcOEt). $^1$H-NMR (400 MHz, CDCl$_3$): 1.02 (d, 3H, J=6.8, NCH(Me)$_2$); 1.14-1.17 (m, 9H, NCH(Me)$_2$); 2.43 (t, J=6.3, CH$_2$CN); 2.64 (dt, J=2.4, 6.1, CH$_2$CN); 3.41-3.77 (m, 2H—(C5'), NCH(Me)$_2$' 2H POCH$_2$); 3.791, 3.800, 3.803 (3s, MeO); 3.87-4.02 (m, CH$_2$O); 4.19-4.28 (m, H—(C4$^5$)); 4.42-4.63 (m, H—(C2'), H—(C3'), CH$_2$OBz); 4.92, 5.03 (2d, J=6.8, OCH$_2$O); 4.96 (s, OCH$_2$O); 5.20, 5.24 (2d, J=8.2, H—(C5)); 6.06 (d, J=3.1, H—(C1'); 6.82-6.86 (m, 4H arom.); 7.22-7.44 (m, H H arom); 7.53-7.58 (m, IH arom); 7.94, 7.99 (2d, J=8.2, H—(C6)); 8.03-8.06 (m, 2H arom); 8.33 (br, s, NHAc). MS: 925 (100, [M+H]$^+$).

A preferred embodiment of the synthesis of a support material comprising chemical groups according to Formulas VIIIa and/or VIIIb as defined above and in the claims is described in the following with reference to reaction scheme 3.

Reaction scheme 3: Synthesis of support material comprising 2'O- or 3'O- octyloxymethyl modified nucleosides.

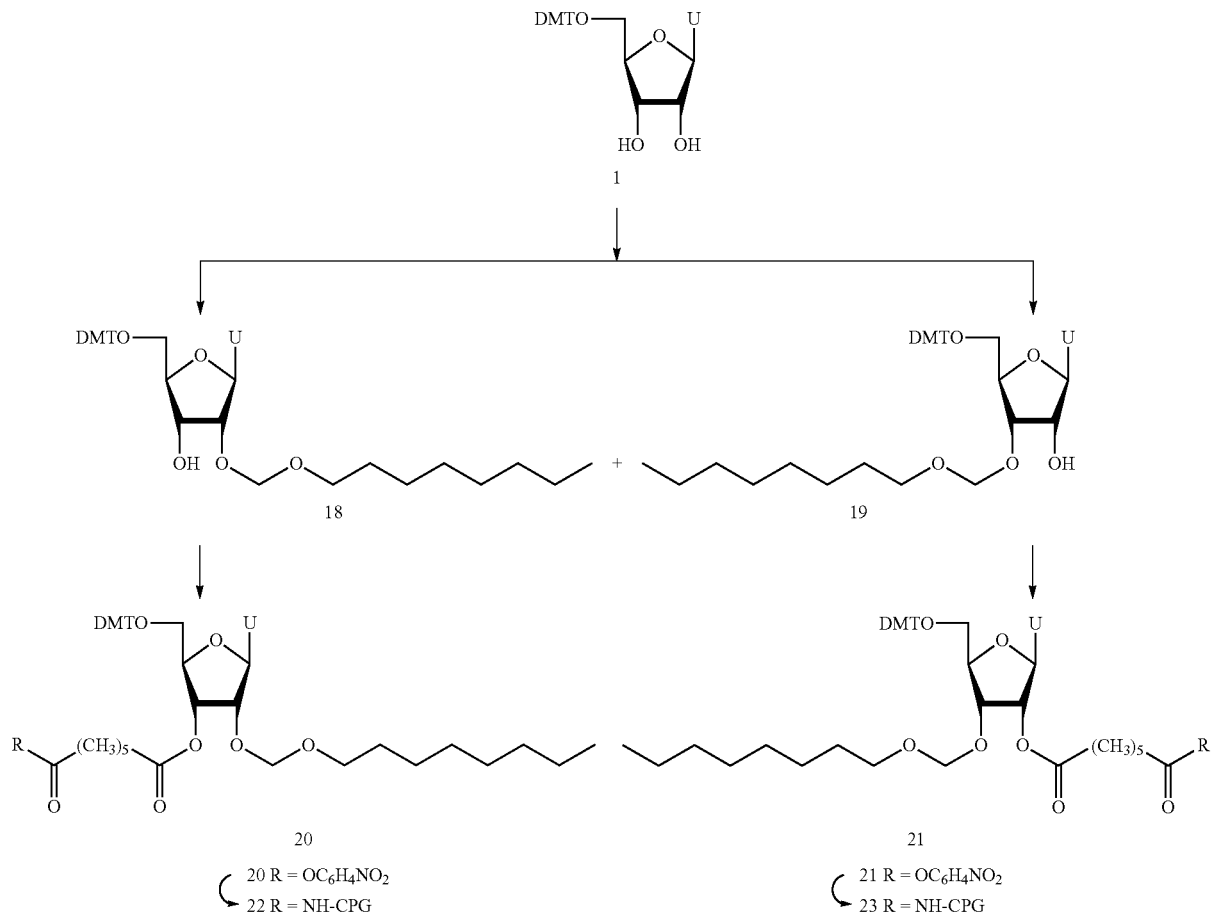

DMT = 4,4'-(Dimethoxy)trityl
CPG = Controlled Pore Glass

Synthesis of 18 and 19

Step 1: A mixture of octane-1-ol (390 mg, 3 mmol) and para-formaldehyde (90 mg, 3 mmol) in CH$_2$Cl$_2$ (11 ml) was dissolved in dichloromethane (18 ml). A flow of HCl(g) was bubbled 15 min through this reaction mixture. The resulting organic layer was separated from the aqueous layer, evaporated to dryness and finally dried 10 min under high vacuum.

Step 2: To a solution of 5'-O-(44'-dimethoxytrityl) uridine 1 (2 g, 3.658 mmol) in 1,2-dichloroethane (12 ml) was added Bu$_2$SnCl$_2$ (1.33 g, 4.39 mmol) and diisopropylethylamine (2.17 ml, 13.8 mmol). The reaction mixture was stirred 15 min at room temperature and then to 70° C. The crude product fom step 1, dissolved in dichloromethane (3 ml), was added slowly to the previous mixture and stirred 30 min at 70° C. After workup, the two diastereoisomers 18 (Ig, 40%) and 19 (490 mg, 20%) were separated by CC (50 g of SiO$_2$, AcOEt/hexane 5:5 to AcOEt 100%). Global yield: 59%. TLC (AcOEt/hexane 95/5): £/0.80 (18); 0.68 (19). $^1$H-NMR (400 MHz, CDCl$_3$); 18: 2.83 (d, J=7.2, OH—(C3')); 3.52-3.68 (m, H—(C5'), H—(OCH$_2$)$_n$); 3.80 (s, 2 MeO); 4.11 (m, H—(C4')); 4.34 (dd, J=3.6, 5.1, H—(C2'); 4.49 (m, H—(C3')); 4.73, 4.78 (2d, J=6.9, OCH$_2$O); 5.31 (d, J=8.2, H—(C5)); 6.04 (d, J=3.1, H—(C1')); 6.85-6.89 (m, 4H arom.); 7.24-7.45 (m, 9H arom); 7.95 (d, J=8.2, H—(C6)); 8.23 (br. s, H—(N3)). 19: 3.39-3.60 (m, OH—(C2'), H—(C5'), H—(OCH$_2$)$_n$); 3.80 (s, 2 MeO); 4.26-4.36 (m, H—C(2'), H—C(3'), H—C(4')); 4.73, 4.78 (2d, J=6.8, OCH$_2$O); 5.37 (d, J=8.1, H—(C5)); 5.97 (d, J=3.1, H—(C1')); 6.85-6.89 (m, 4H arom.); 7.24-7.45 (m, 9H arom); 7.85 (d, J=8.2, H—(CO)); 8.9 (br. s, H—(N3)).

Synthesis of 20 and 21

Pimelicacid-dinitrophenylester (697 mg, 1.73 mmol) was dissolved in pyridine (2.89 ml). DMAP (17.7 mg, 0.14 mmol) and 18 or 19 (200 mg, 0.29 mmol each), respectively, were added. After stirring over night at room temperature, the mixture was evaporated and co-evaporated twice with toluene (20 ml). CC (10 g of SiO$_2$, AcOEt/hexane 3:7 to AcOEt/hexane 6:4) gave 20 (121 mg, 46%) and 21 (118 mg, 45%). Colorless foam. TLC (AcOEt/hexane 7:3): £/0.70 (20); 0.67 (21). $^1$H-NMR (400 MHz, CDCl$_3$); 20:1.46 (m, CH$_2$); 1.70 (m, CH$_2$); 1.77 (m. CH$_2$); 2.42 (t, J=7.6, CH$_2$); 2.62 (t, J=7.5, CH$_2$); 3.52-3.68 (m, H—(C5'), H—(CH$_2$)$_n$); 3.80 (s, 2 MeO); 4.11 (m, H—(C4')); 4.34 (dd, J=3.6, 5.1, H—(C2'); 4.49 (m, H—(C3')); 4.73, 4.78 (2d, J=6.9, OCH$_2$O); 5.31 (d, J=8.2, H—(C5)); 6.04 (d, J=3.1, H—(C1')); 6.85-6.89 (m, 4H arom.); 7.24-7.45 (m, 9H arom); 7.95 (d, J=8.2, H—(Co)); 8.23 (br. s, H—(N3)). 21: 1.46 (m, CH$_2$); 1.70 (m, CH$_2$); 1.77 (m. CH$_2$); 2.42 (Y, J=7.6, CH$_2$); 2.62 (t, J=7.5, CH$_2$); H—(C5'), H—C(CH$_2$)n); 3.80 (s, 2 MeO); 4.26-4.36 (m, H—C(2'), H—C(3'), H—C(4')); 4.73, 4.78 (2d, J=6.8, OCH$_2$O); 5.37 (d, J=8.1, H—(C5)); 5.97 (d, J=3.1, H—(C1')); 6.85-6.89 (m, 4H arom.); 7.24-7.45 (m, 9H arom); 7.85 (d, J=8.2, H—(Co)); 8.9 (br. s, H—(NS)).

Preparation of the Solid Support 22 and 23

To a solution of the active ester (0.05 mmol) 20 or 21 in DMF (1.6 ml) was added long-chain-alkylamino CPG (400 g) and then $^i$Pr2NEt (0.15 ml). The mixture was shaken for 20 h at room temperature. After filtration, the solid support 22 or 23 was washed with DMF and CH$_2$Cl$_2$, dried, suspended in pyridine (1 ml) and Ac$_2$O (0.64 ml) and shaken for 2 h at room temperature. After filtration, the solid was washed with DMF and CH$_2$Cl$_2$, and dried under high vacuum. Typical loadings of the solid support was 30 μmol/g with 500-A CPG.

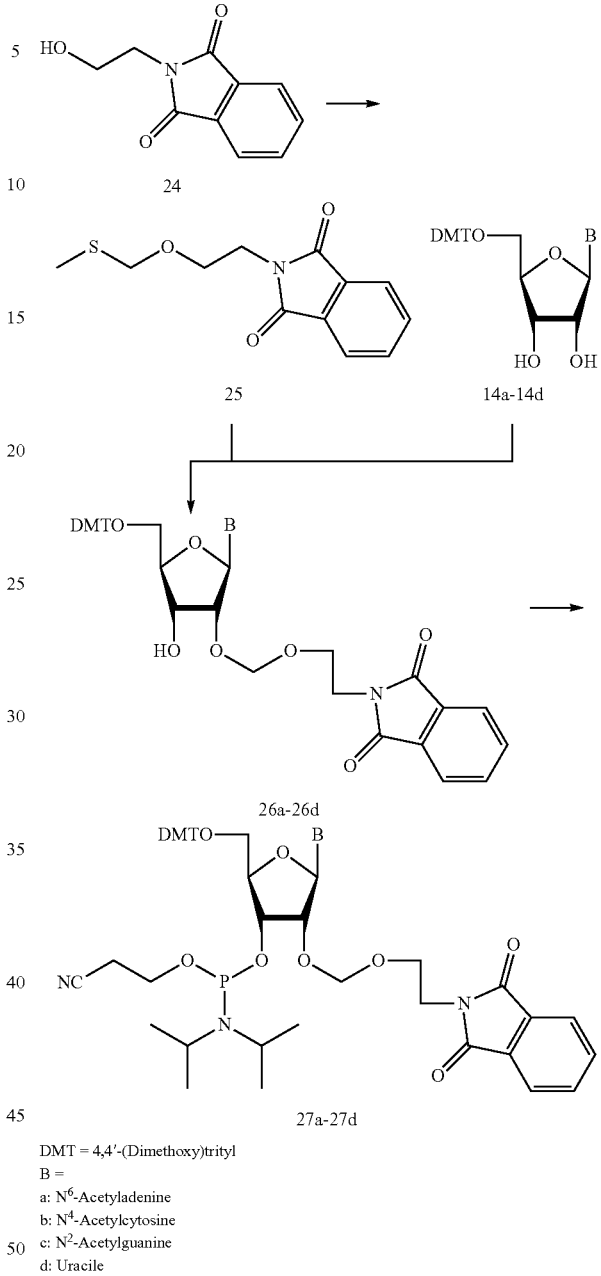

Reaction scheme 4: Preparation of phosphoramidites

DMT = 4,4'-(Dimethoxy)trityl
B =
a: N$^6$-Acetyladenine
b: N$^4$-Acetylcytosine
c: N$^2$-Acetylguanine
d: Uracile In synthetic step I (24→>25) the hydroxyl group of phthalimide derivative 24 is reacted to give a functional thioacetal group. In subsequent step 2, the thioacetal group of 25 is reacted in situ to yield the corresponding chloromethylether. Subsequently, in step 2 (25+14a-d→15a-15d), 5'-O-protected nucleosides 14a-14d (prepared according to S. Pitsch, P. A. Weiss, L. Jenny, A. Stutz. X. Wu, Helv. CHm. Ada, 2001. 84, 3773) are alkylated in the T-O-position to yield 2'-O-formacetal substituted nucleosides 26a-26d. Finally, in step 3 (26a-26d→>27a-27d), nucleosides 26a-26d are reacted with diisopropylphosphoramidochlorodite in the 3'-0 position to yield phosphoramidites 27a-27d.

Synthesis of 25

24 (9.6 g, 50 mmol) was dissolved in DMSO (75 ml), treated with AcOH (75 ml) and Ac$_2$O (75 ml). After 2 days of stirring the reaction mixture was poured in a well stirred mixture of 400 ml (AcOEt/hexane 1:1) and 400 ml Of $H_2O$. The organic phase was then extracted with 400 ml of sat. $NaHCO_3$, dried with $MgSO_4$ and evaporated. The residue was dissolved in hot AcOEt (20 ml) and hexane (180 ml) was added. The mixture was stirred overnight at 4° C. and the crystallised product 25 was filtered, washed with. AcOEt/Hexane 1:9, and dried under vacuum: 25 (9.3 g, 74%) as a white powder. $R_f$ 0.58 (AcOEt). $^1$H-NMR (400 MHz, $CDCl_3$): 2.06 (s, MeS); 3.83, 3.84 (2t, J=5.5, $SCH_2$, $CH_2N$); 4.65 (s, $SCH_2O$); 7.73-7.75 (m, 2H arom.); 7.86-7.89 (m, 2H arom.).

General Procedure for the Synthesis of Nucleosides 26a-d

To a solution of nucleosides 14a-d (1 eq) and thiomethyl-ether 25 in 1,2-dichloroethane (0.25 M) were added successively ($^i$Pr)$_2$NEt (3.5 eq) and $Bu_2SnCl_2$ (1.2 eq). The reaction mixtures were stirred at room temperature for 30 min, heated to 70°, treated with N-chlorosuccinimide (2 eq) and stirred for 30 min at 70°. The reaction mixtures were then subjected to usual work up. The organic phase was filtered through Celite, dried with $MgSO_4$ and evaporated. The residue was purified by CC.

Synthesis of 26a

According to general procedure with 14a (2.44 g, 4.0 mmol). CC (50 g of $SiO_2$, AcOEt/hexane 7:3 to AcOEt then to AcOEt/MeOH 97:3): 26a (785 mg, 24%) as a foam. $R_f$ 0.45 (AcOEt/MeOH 95:5). $^1$H NMR (400 MHz, $CDCl_3$): 2.65 (s, MeCO), 2.78 (d, J=5.4 Hz, HO—(CS')), 3.43 (dd, J=10.6. 4.2 Hz. H—(C5)), 3.49 (dd, J=10.6, 3.2 Hz, H—(C5')), 3.73-3.88 (m. MeO, $CH_2O$, $CH_2N$), 4.24 (q, J=4.2 Hz, H—(C4'), 4.53 (q, J=5.1 Hz, H—(C3')); 4.84-4.90 (m, $OCH_2O$, H—(C2')), 6.20 (d. J=4.5 Hz, H—(C1')), 6.79-6.85 (m, 4H arom.), 7.21-7.34 (m, 7H arom.), 7.40-7.45 (m, 2H arom.), 7.68-7.72 (m, 2H arom.), 7.79-7.83 (m, 2H arom.), 8.18 (s, H—(C2)), 8.50 (br, s, NHAc), 8.60 (s, H—(C8)). ESI-MS (Pos. Mode): 815.4 (100, [M+H]$^+$).

Synthesis of 26b

According to general procedure with 14b (2.38 g, 4.0 mmol. CC (50 g of $SiO_2$ AcOEt/hexane 7:3 to AcOEt then to AcOEt/MeOH 97:3): 26b (582 nig, 19%) as light yellow foam. Rf 0.43 (AcOEtMeOH 95:5). $^1$H-NMR (400 MHz, $CDCl_3$): 2.23 (s, MeCO), 2.96 (d, J=9.3 Hz, HO—(C3')), 3.53 (dd, J=11.2, 2.6 Hz, H—(C5)), 3.58 (dd, J=11.5, 2.2 Hz, H—(C5')), 3.84 (d, J=1.0 Hz, MeO), 3.88-3.98 (m, $CH_2O$, $CH_2N$), 4.07 (m, H—(C4')), 4.21 (d, J=5.1 Hz, H—(C2')), 4.42 (td, J=9.3, 5.4 Hz, H—(C3')), 4.99 (d, J=6.7 Hz, $OCH_2O$), 5.17 (d, J=6.4 Hz, $OCH_2O$), 5.94 (s, H—(C1')), 6.87-6.91 (m, 4H arom.), 7.09 (d, J=7.5 Hz, H—(C5)), 7.26-7.37 (m, 7H arom.), 7.41-7.45 (m, 2H arom.), 7.68-7.72 (m, 2H arom.), 7.81-7.85 (m. 2Ii arom.), 8.46 (d, J=7.5 Hz, H—(C6)), 9.11 (br, s, NHAc). ESI-MS (Pos. Mode): 791.3 (100, [M+H]$^+$).

Synthesis of 26c

According to general procedure with 14c (2.51 g, 4.0 mmol). CC (25 g of $SiO_2$, AcOEt/hexane 8:2 to AcOEt then to AcOEt/MeOH 95:5): 26c (1950 mg, 60%) as yellow foam. $R_f$ 0.38 (AcOEt/MeOH 95:5). $^1$H-NMR (400 MHz, $CDCl_3$) 1.99 (s, MeCO), 3.30 (dd, J=10.9, 4.2 Hz, H—(C5')), 3.51 (dd, J=10.9, 2.2 Hz, H—(CS')), 3.73-3.99 (m, MeO, $CH_2O$, $CH_2N$), 4.17 (m, H—(C4')), 4.45 (q, J=5.1 Hz, H—(C3')), 4.79-4.88 (m, $OCH_2O$, H—(CT)), 5.96 (d, J=4.2 Hz, H—(C1')), 6.79-6.85 (m, 4H arom.), 7.19-7.38 (m, 7H arom.), 7.46-7.50 (m, 2H arom.), 7.70-7.74 (m, 2H arom.), 7.78-7.82 (m, 2H arom.), 7.86 (s, H—(C8)), 8.96 (br, s, NHAc), 12.02 (br, s H—(Nl)). ESI-MS (Pos. Mode): 831.3 (100, [M+H]$^+$).

Synthesis of 26d

According to general procedure with 14d (2.18 g, 4.0 mmol). CC (55 g of $SiO_2$, AcOEt/hexane 2:8 to AcOEt): 26d (840 mg, 28%) as white foam. $R_f$ 0.75 (AcOEt/MeOH 95:5). $^1$H-NMR (400 MHz, $CDCl_3$): 2.75 (d, J=7.4 Hz, OH—(C3')), 3.51 (dd, J=11.2, 2.6 Hz, H—(C5')), 3.55 (dd, J=11.2, 2.2 Hz, H—(CS')), 3.82 (s, MeO), 3.87-3.98 (m, $CH_2O$, $CH_2N$), 4.05 (m, H—(C4')), 4.24 (dd, J=5.1, 2.6 Hz, H—(C2')), 4.44 (m, H—(C3')), 4.91 (d, J=6.7 Hz, $OCH_2O$), 5.00 (d, J=6.7 Hz, $OCH_2O$), 5.29 (dd, J=8.3, 1.9 Hz, H—(CS)), 5.96 (d, J=2.6 Hz, H—(C1')). 6.84-6.90 (m, 4H arom.). 7.23-7.42 (m. 9H arom.), 7.70-7.74 (m, 2H arom.), 7.83-7.87 (m, 2H arom.). 7.94 (d, J=8.0 Hz. H—(Co)), 8.13 (br. s, H—(N3)).

General Procedure for the Synthesis of Phosphoramidites 27a-d

To a solution of the nucleosides 26a-d (1 eq) in $CH_2Cl_2$ (0.25 M) were added successively ($^i$Pr)$_2$NEt (2.5 eq) and diisopropylphosphoramidochloridite (1.2 eq). The reaction mixtures were stirred for 14 h at room temperature and subjected to CC.

Synthesis of 27a

According to general procedure with 26a (870 mg, 1.07 mmol). CC: (17 g of $SiO_2$. AcOEt/hexane 2:8 (+2% NEt$_3$) to AcOEt (+2% NEt$_3$)): 27a (970 mg 89%) as white foam (1:1 mixture of diastereoisomers). $R_f$ 50 (AcOEt). $^1$H-NMR (400 MHz, $CDCl_3$): 1.07 (d, J=6.7 Hz. NCH(Me)$_2$), 1.16-1.20 (m, NCH(M?)$_2$), 2.40 (t, J=6.4 Hz, $CH_2CN$), 2.63-2.69 (m, $CH_2CN$, MeCO), 3.36 (m, IH POCH$_2$), 3.49-3.97 (m. 2H—(C5'), MeO, $CH_2N$, $CH_2O$, IH POCH$_2$), 4.36 (m, H—(C4')), 4.69 (m, H—(C3')), 4.76 (d. J=7.0 Hz. IH $OCH_2O$), 4.80 (d, J=7.0 Hz, 0.5H $OCH_2O$), 4.87 (d, J=6.7 Hz, 0.5H $OCH_2O$), 5.08 (m. H—(C2')), 6.19 (d, J=5.1 Hz, 0.5H H—(Cr)), 6.22 (d, J=4.8 Hz, 0.5H H—(CF)X 6.78-6.83 (m, 4H arom.), 7.19-7.44 (m, 9H arom.), 7.68-7.74 (m, 2H arom.), 7.77-7.83 (m, 2H arom.), 8.22 (s, H—(C2)), 8.50 (br, s, NHAc), 8.60 (S, H—(C8)). $^{31}$P-NMR (161 MHz, $CDCl_3$): 151.67; 151.77. ESI MS (Pos. Mode): 1015.37 (100. [M+H]$^+$)

Synthesis of 27b

According to general procedure with 26b (550 mg, 0.70 tπmol). CC: (11 g of $SiO_2$, AcOEt/hexane 2:8 (+2% NEt$_3$) to AcOEt/hexane 8:2 (+2% NEt$_3$)): 27b (540 mg, 78%) as white foam (1:1 mixture of diastereoisomers). $R_f$ 0.43 (AcOEt).). $^1$H-NMR (400 MHz, $CDCl_3$): 0.99 (d, J=7.0 Hz, NCHC Me)$_2$), 1.11 (d, J=6.7 Hz, NCH(Me)$_2$), 1.12 (d, J=7.0 Hz. NCH(Me)$_2$), 1.16 (d, J=6.7 Hz, NCH(Me)$_2$), 2.22 2.23 (2s, MeCO), 2.43 (t, J=6.4 Hz: $CH_2CN$), 2.66 (m, $CH_2CN$), 3.42-3.78 (m, 2H—(C5'), NCH(Me)$_2$, 2H POCH$_2$), 3.79-4.07 (m, MeO, $CH_2N$, $CH_2O$), 4.24-4.38 (m, H—(C4'). H—(C2')), 4.49 (m, H—(C3')). 4.95 (d, J=6.7 Hz, 0.5H $OCH_2O$), 4.97 (d, J=6.7 Hz, 0.5H $OCH_2O$), 5.02 (d, J=6.7 Hz, 0.5H $OCH_2O$), 5.02 (d, J=6.4 Hz, 0.5H $OCH_2O$), 6.05 (d, J=1.0 Hz. 0.5H H—(C1')), 6.06 (d, J=1.3 Hz, 0.5H H—(C1'))-6.85-6.90 (m, 4H arom.), 6.92 (d, J=7.7 Hz. 0.5H H—(CS)). 7.00 (d, J=7.7 Hz, 0.5H H—(CS)). 7.26-7.46 (m, 9H arom.), 7.68-7.73 (m, 2H arom.), 7.82-7.86 (m. 2H arom.), 8.44 (d, J=7.4 Hz. 0.5H H—(Co)). 8.50 (d, J=7.4 Hz. 0.5H H—(Co)). 8.94. 9.07 (br. 2s, NHAC). 31P-NMR (161 MHz, $CDCl_3$): 150.88: 152.42. MALDI-TOF MS (Pos. Mode): 1013.9 (100. [M+Na]$^+$); 1029.9 (49, [M+K]$^+$)

Synthesis of 27c

According to general procedure with 26c (1940 mg, 2.33 mmol). CC: (35 g of $SiO_2$, AcOEt/hexane 5:5 (+2% NEt$_3$) to AcOEt (±2% NEt$_3$)): 27bc (1810 mg, 80%) as white foam (1:1 mixture of diastereoisomers). $R_f$ 0.44 (AcOEt). $^1$H-NMR (400 MHz, $CDCl_3$): 1.00 (d. J=7.0 Hz, NCH(Me)$_2$), 1.15 (d, J=6.7 Hz. NCH(MO$_2$), 1.15 (d, J=6.7 Hz, NCH(Me)$_2$), 1.87, 1.96 (2s, MeCO), 2.32 (t J=6.1 Hz, $CH_2CN$), 2.68 (td, J=6.4, 2.2 Hz, CH$_2$CN), 3.27 (m, IH POCH$_2$), 3.48-3.99 (m, IH POCH$_2$. 2H—(C5'). MeO. CH$_2$O, CH$_2$N, NCIZ(Me)$_2$), 4.30 (m. H—(C4')). 4.51 (m, 0.5H—(C3')). 4.61 (m. 0.5H—(C3')), 4.73-4.82 (m, 1.5H OCH$_2$O). 4.89 (d, J=7.0 Hz, 0.5H, OCH$_2$O), 4.97 (m. B—(CT)), 5.93 (d, J=4.5 Hz, 0.5H H—(CF)). 5.98 (d. J=5.1 Hz, 0.5H H—(CF)). 6.79-6.86 (m. 4H arom.), 7.19-7.55 (m, 9H arom.), 7.70-7.77 (m, 2H arom.), 7.79-7.84 (m, 2H arom.), 7.88, 7.91 (2 s, H—(C8)). 8.62, 8.87 (br, 2s, NHAc). 11.93 (br, s, H—(Nl)). 31P-NMR (161 MHz, CDCl$_3$): 150.93; 151.60. MALDI-TOF MS (Pos. Mode): 1031.9 (57. [M+Naf] 1053.9 (100, [M+Na]$^+$); 1069.9 (53, [M+K]$^+$).

Synthesis of 27d

According to general procedure with 26d (473 mg. 0.63 mmol). CC: (10 g of SiO$_2$. AcOEt/hexane 2:8 (+2% NEt$_3$) to AcOEt/hexane 9:1 (+2% NEt$_3$)): 27d (446 mg. 75%) as white foam (1:1 mixture of diastereoisomers). R$_1$ 0.80 (AcOEt). $^1$H-NMR (400 MHz, CDCl 3) δ 1.02 (d. J=6.7 Hz, NCH (Me)$_2$), 1.13-1.18 (m. NCH(Me)$_2$), 2.44 (t, J=6.1 Hz. CH$_2$CN), 2.70 (m. CH$_2$CN), 3.39-3.84 (m, POCH$_2$, 2H—(C5'), MeO, NCT-Z(Me)$_2$), 3.88-4.01 (m. CH$_{12}$O. CH$_2$N), 4.20 (m, H—(C4')). 4.40 (m, H—(C2')), 4.55 (m. H—(C3')), 4.83 (d, J-6.7 Hz, 0.5H OCH$_2$O), 4.87 (s, IH OCH$_2$O), 4.99 (d. J=6.7 Hz. 0.5H OCH$_2$O), 5.21 (d, J=8.3 Hz, 0.5H H—(C5)), 5.28 (d. J=8.3 Hz. 0.5H H—(CS)), 6.01 (d. J=3.2 Hz. 0.5H H—(CF)), 6.03 (d, J=3.5 Hz. 0.5H H—(CF)), 6.83-6.88 (m, 4H arom.). 7.23-7.43 (m. 9H arom.), 7.71-7.76 (m. 2H arom.). 7.83-7.87 (m. 2H arom.), 7.91 (d. J=8.3 Hz. 0.5H H—(C6)). 7.94 (d-J=8.3 Hz, 0.5H H—(C6)), 8.09 (br, s, H—(N3)). $^{31}$P-NMR (161 MJ-Iz$_3$ CDCl$_3$): 151.14; 152.27. MALDI-TOF MS (Pos. Mode): 972.7 (85$_r$ [A/+Na]*): 988.8 (100, [M+K]$^+$).

Oligonucleotide Synthesis and Deprotection

The RNA oligonucleotides were prepared using a Gene Assembler Plus {Pharmacia) with 40 mg of solid support (either conventional solid supports or solid supports according to the present invention) (loading 30 μmol/g) and 2'-O-tom-protected ribonucleoside phosphoramidites, DNA phosphoramidites (obtained from the Glen Research Corporation, Sterling, Va., USA), 2'OMe ribonculesoide phosphoramidites (obtained from the Glen Research Corporation, Sterling, Va., USA) or phosphoramidites according to the present invention utilizing standard procedures as for instance outlined by S. Pitsch, P. A. Weiss, L. Jenny, A. Stutz, X. Wu, *Helv. Chim. Acta* 2001, 84, 3113. The selection of the solid supports and the selection of the respective phosphoramidites used in the syntheses depend on the nature of the modification of the RNA oligonucleotides. Additionally used modifications in the nucleosides included 2'-deoxy-modified nucleotides, 2'-methoxy-modified nucleotides as well as nucleotides comprising in the 3'-position a —O—CH$_2$—O—(CBb)$_7$-CHs group. An example of such a modified nucleotide is shown below in Formula IV.

FORMULA IV

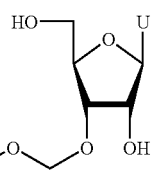

The solid support was subsequently removed from the cartridge and treated with a 1:1 mixture of 12 M MeNH$_2$ in H$_2$O and 8 M MeNH$_2$ in EtOH (1 ml) for 5 h at 35° C. By centrifugation, the supernatent solution was separated from the solid support and evaporated, and the residue was dissolved in 1 M Bu$_4$NF—SH$_2$O soln. in THF (1 ml). After 14 h at 25° C., 1 M 7ra.HCl buffer (pH 7.4, ImI) was added. The solution was concentrated to 1 ml and desalted on NAP-10 column {Pharmacia) according to the manufacturer's instructions. The crude RNA sequence was purified by AE-HPLC (20-60% B in A, see below, in 45 min, 3 injections). The fractions containing the pure sequence were pooled (30 ml), treated with 1 M aqueous Et$_3$N. AcOH (pH 7, 5 ml) and applied to Sepak cartridges {Waters). After elution of the salts with 0.1 M aqueous Et$_3$N—AcOH (pH 7, 10 ml), followed by H$_2$O (20 ml), the sequences was eluted with MeCN/H$_2$O 1:1 (5 ml) and finally evaporated to dryness. The residue was redissolved in ImI water, quantified and analysed by MALDI TOF MS.

For an example of a RNA oligonucleotide according of the present invention FIG. 1 demonstrates different purification steps of the RNA oligonucleotide.

Oligonucleotide Hybridization and Duplex Purification

The two single strands (sense and antisense strand) in H$_2$O were mixed in a 1:1 ratio (total double strand concentration ca. 20 nmol), heated 1 min. to 80° C. and slowly cooled to 25° C. After lyophilization, the duplex was dissolved in 50 μl, mixed with 50 μl formamide blue (10 ml formamide, 200 μl 0.5M EDTA, bromphenol blue) and then subjected to a polyacrylamid gel electrophoresis. (12% acrylamide, 1:40 bisacrylamide, 250 V). After UV revelation the duplex was separated from the gel in a electrolution cell (45 min, 70 V). The crude product was purified by AE-HPLC (20-60% B in A, see below, in 25 min, 1 injection). The fractions containing the pure duplex were pooled, treated with 1 M aqueous Et$_3$N. AcOH (pH 7) and applied to Sepak cartridges (Waters). After elution of the salts with 0.1 M aqueous Et$_3$NAcOH (pH 7; 10 ml), followed by H$_2$O (20 ml), the duplex was eluted with MeCN/H$_2$O 1:1 (5 ml) and finally evaporated to dryness.

Stability Tests

Stability in Culture Medium

2 μg siRNA were incubated at 37° C. in 300 μl DMEM/10% FCS (Dulbecco's Modified Eagle Medium (D-MEM) (IX), Invitrogen-GIBCO). The resulting mixture was analyzed on AE-HPLC (20-60% B in A, see below, in 25 min, 1 injections) at 10, 4 h, 24 h, 48 h and 3 d.

Stability in Human Serum

3 μg siRNA were pipetted in 100 μl 100% human serum. The siRNA was incubated in serum at 37° C. and at different time points 25 μl aliquots were collected and frozen until analysis.

Stability in Cell Culture Medium after Complexation with Transfection Reagent

2 μg siRNA were incubated for 15 min with RNAiFect (obtained from QIAGEN GmbH. Hilden, Germany) in 1:6 ratio (μg siRNA:μl transfection reagent) to form transfections complexes at real transfection conditions. After complex formation the mixture was pipetted in 300 μl cell culture medium with 10% FCS (fetal calf serum). The transfection complexes were incubated at normal cell growth conditions (i.e. 37° C., 5% CO$_2$) and at different time points aliquots were collected and frozen until analysis.

Analysis of siRNA Stability

PAA Gels

12% PAA-TBE mini gels (Mini-PROTEAN 3 Electrophoresis System, from Bio-Rad) were used for analysis of the treated siRNAs. 11 μl of each aliquot were mixed with 4 μl Loading Buffer (2.5×TBE, 50% Formamid, Orange G, 20% Glycerol) and loaded onto the gel. The samples were separated for 2.5 h at 100 V.

HPLC Analysis

HPLC analysis was performed under denaturing conditions using the following protocol:

Column:
DNAPac PA1OO Analytical, 4*250 mm
Eluants:
A: 0.0 M NaClO$_4$, 5 M urea, 12.5 mM Tris HCl (pH=7.4), final volume: 1 l 1 (Aqua Braun H$_2$O)
B: 0.5 M NaClO$_4$, 5 M urea, 12.5 mM Tris HCl (pH=7.4), final volume: 1 l (H$_2$O)
Gradient: linear gradient from 20 to 60% B in A
Time: 25 min.
Flow rate: 1 ml/min
Temperature: 80 to 85° C.
Inject volume: 500 μl (300 μl sample+200 μl buffer A)
Column wash: 20% MeOH, 50 mM NH$_4$Cl, final volume: 1 l H2O
Column Storage: 20% MeOH, 50 mM NH$_4$Cl, final volume: 1 l H2O The following is a brief description of the drawings.

Figure 6:
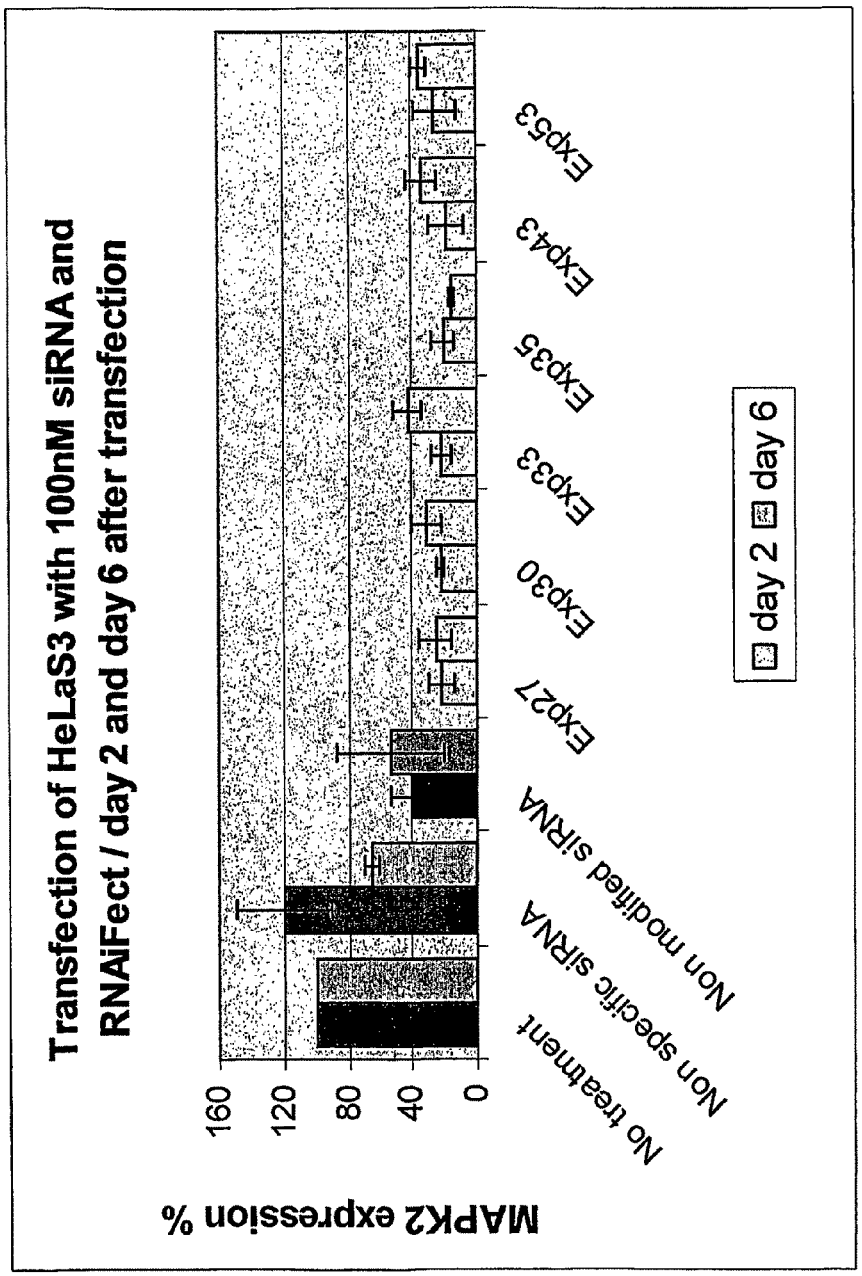
Figure 6:
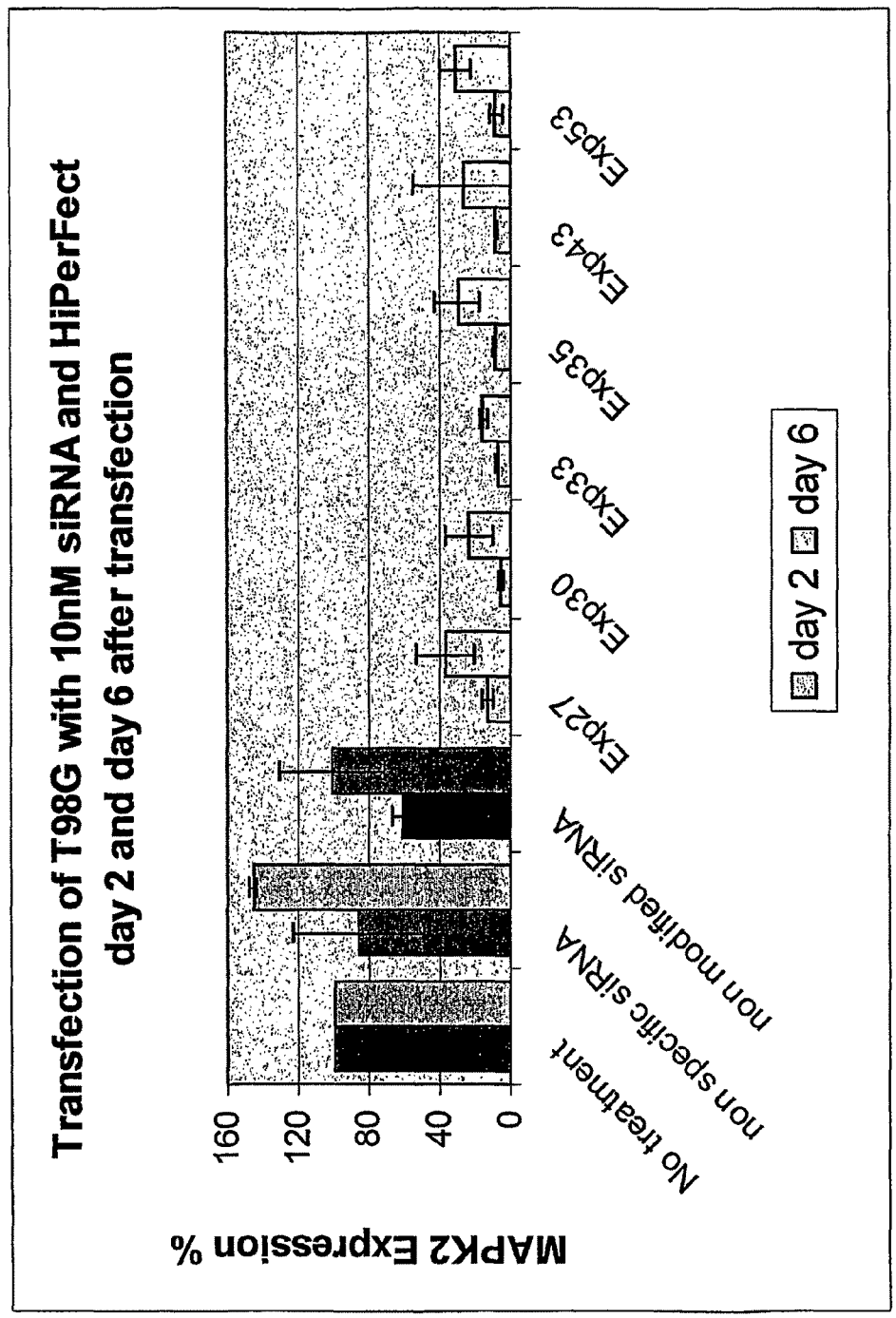
Figure 7:
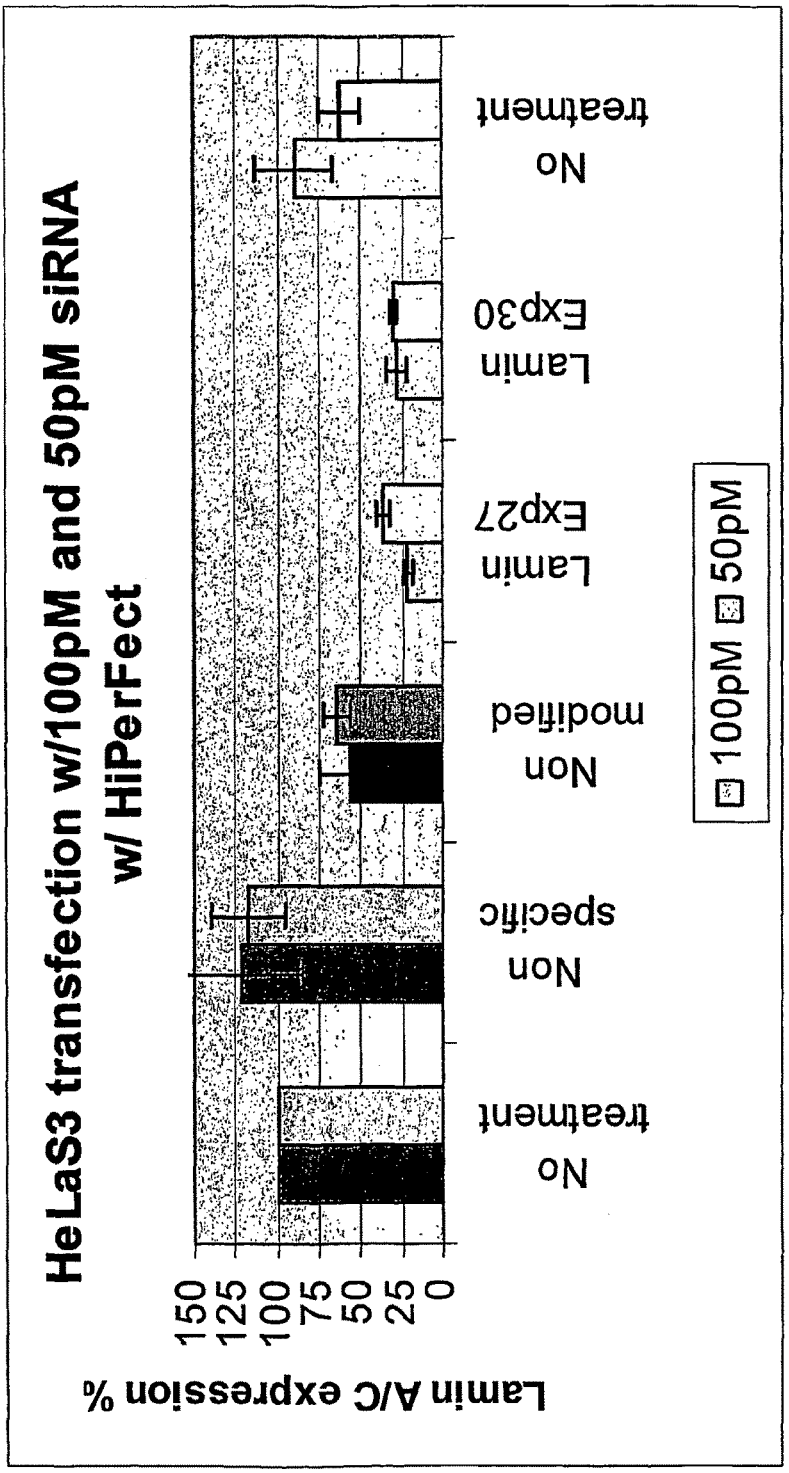
Figure 7:
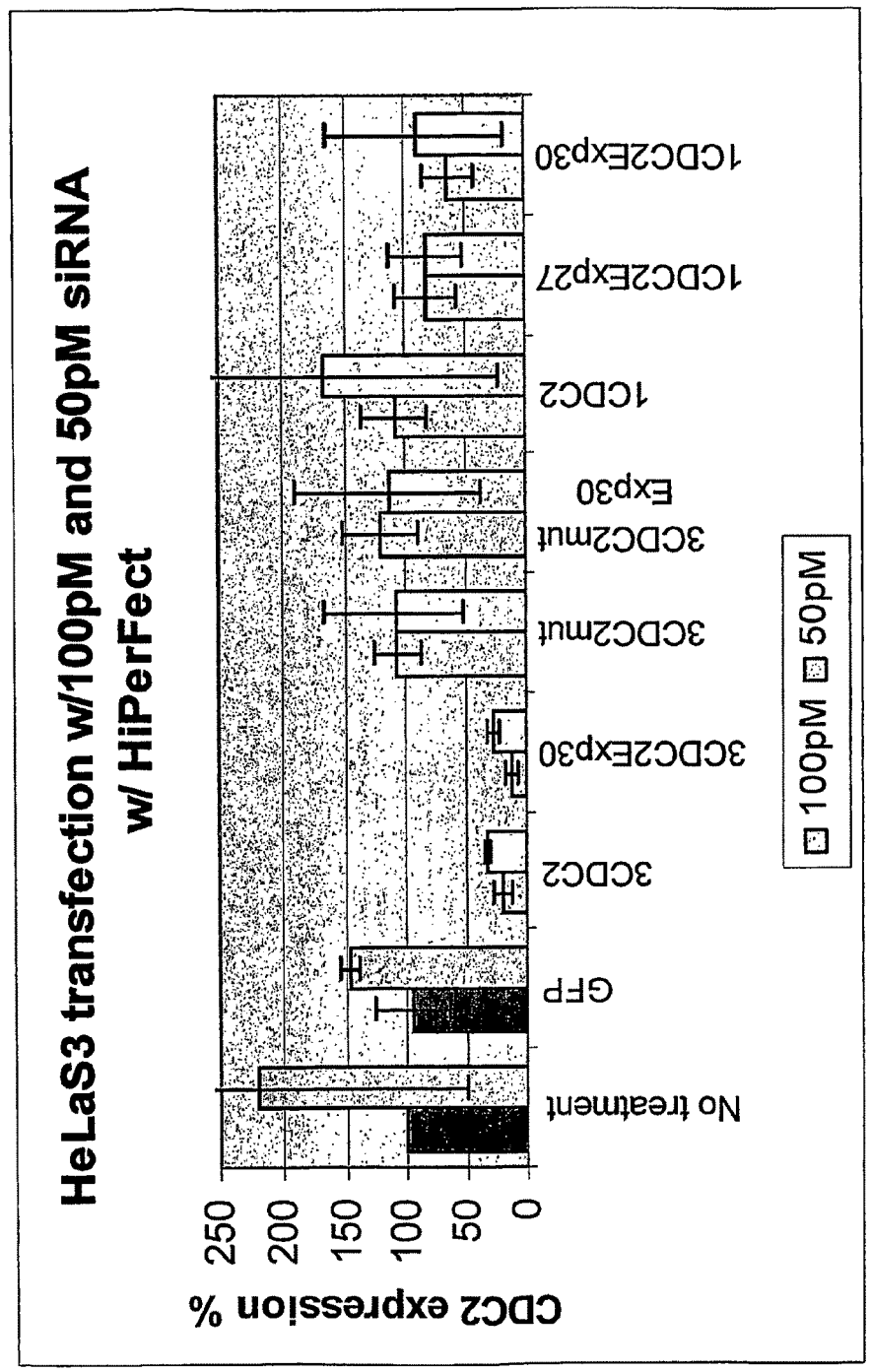
Figure 8:
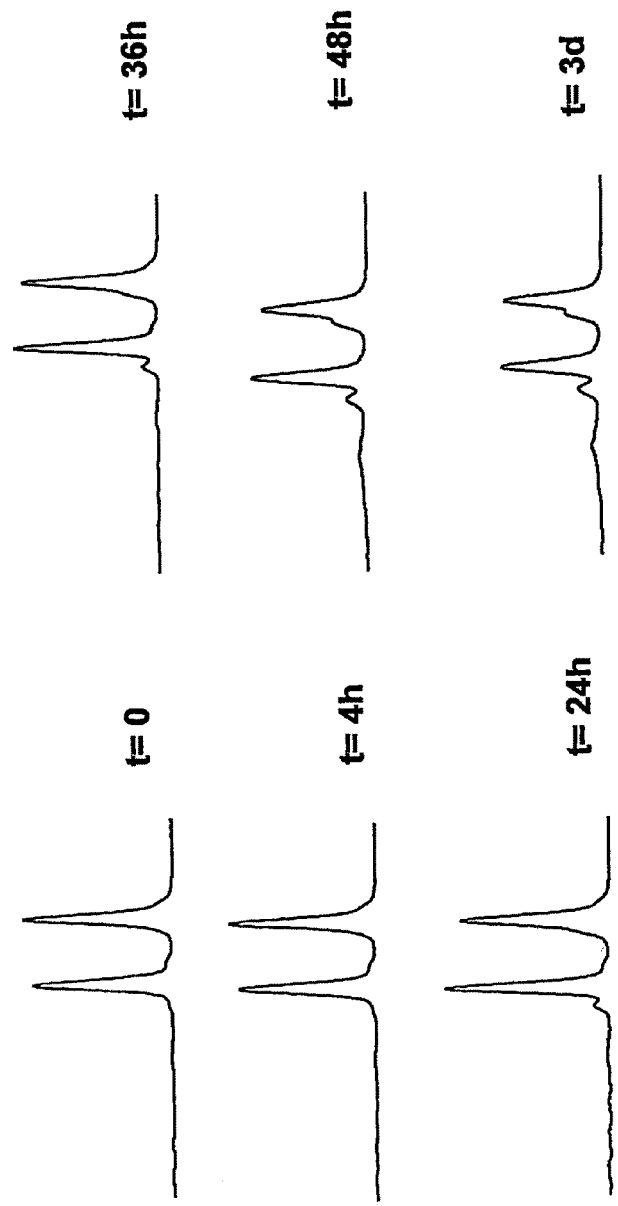
Figure 9:
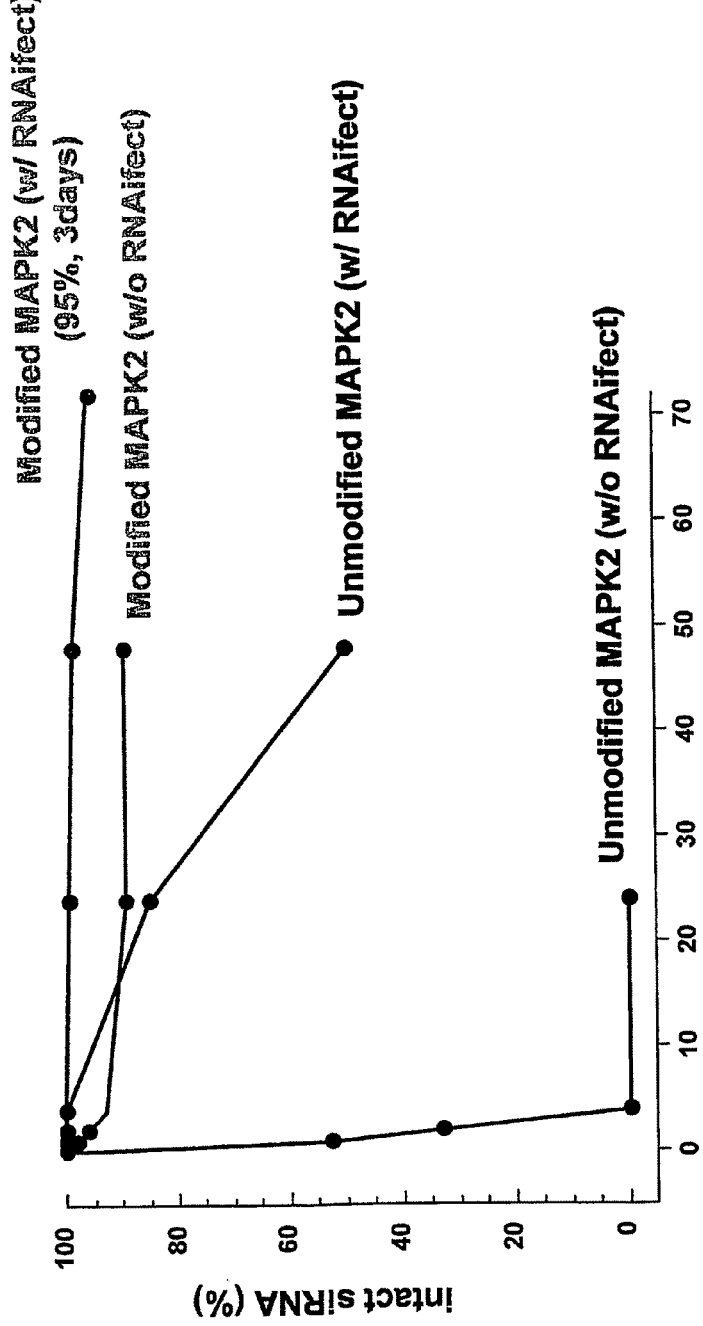
Figure 10:
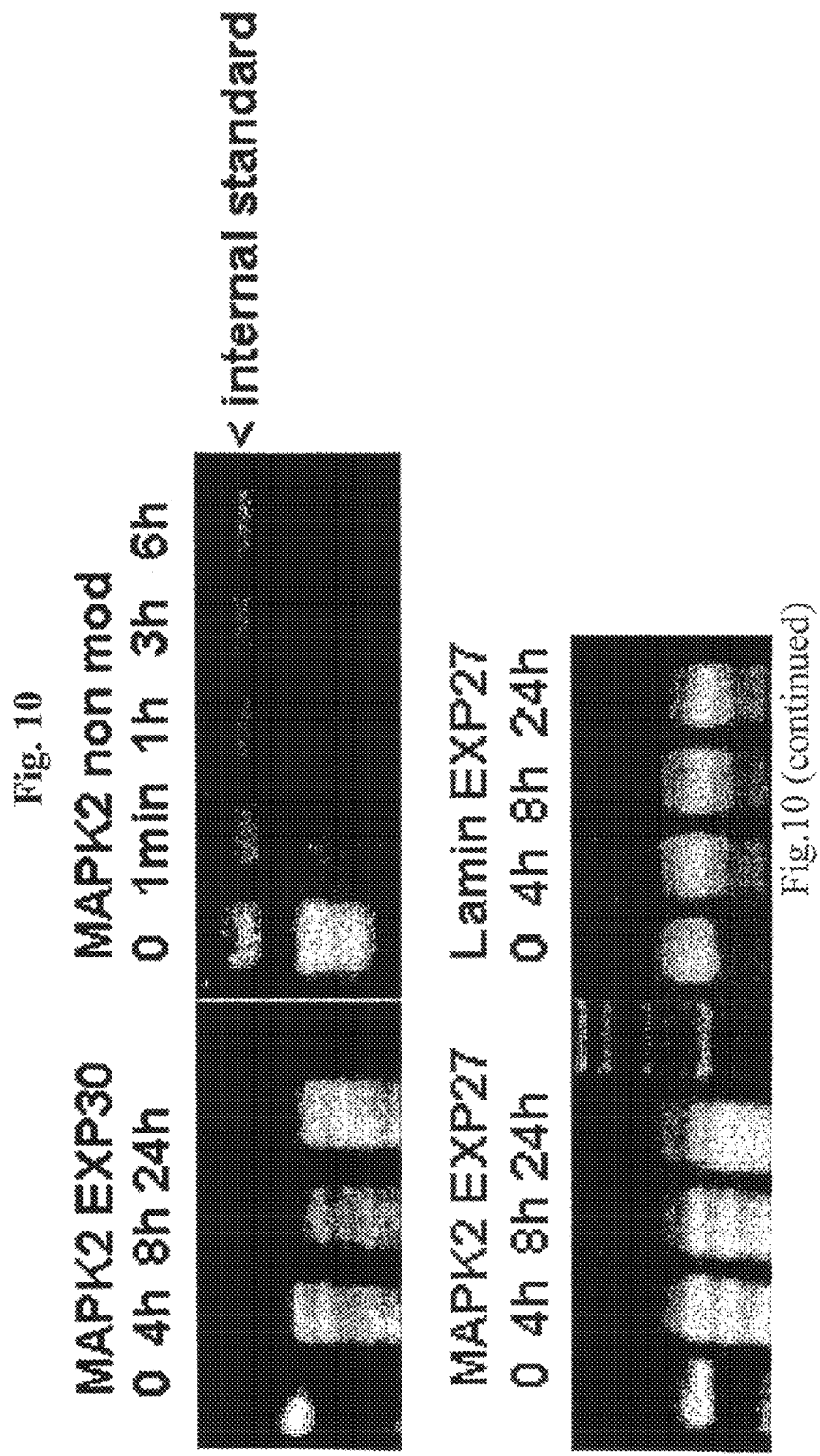
Figure 10:
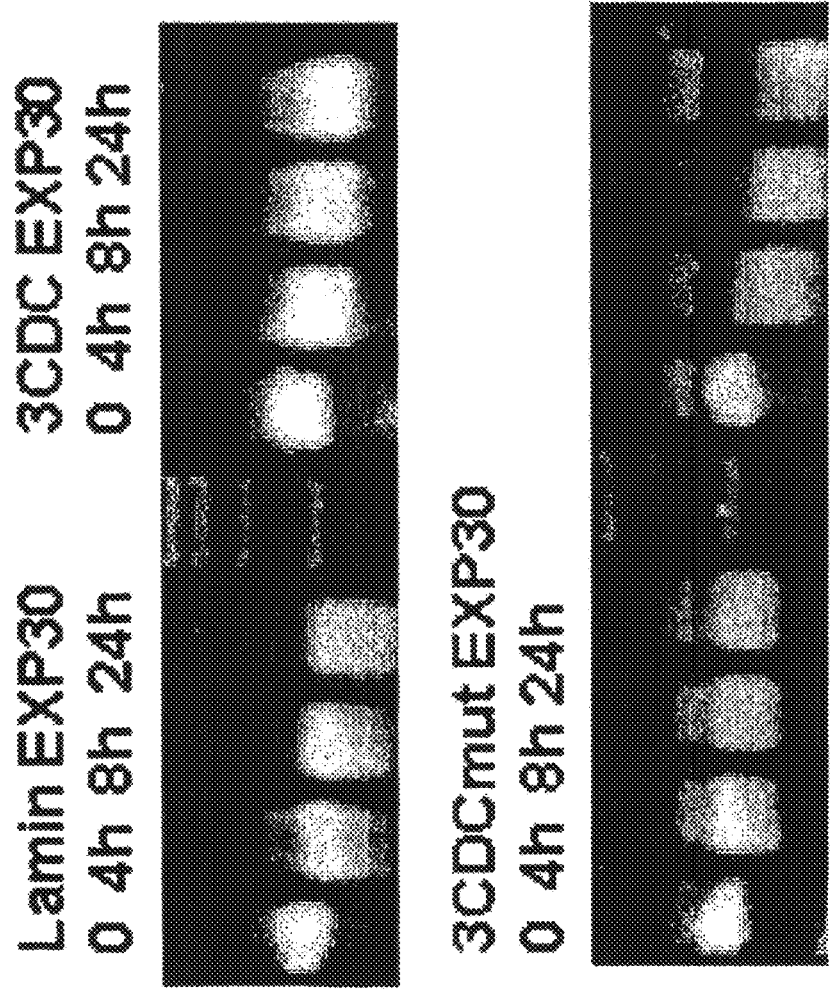
Figure 10:
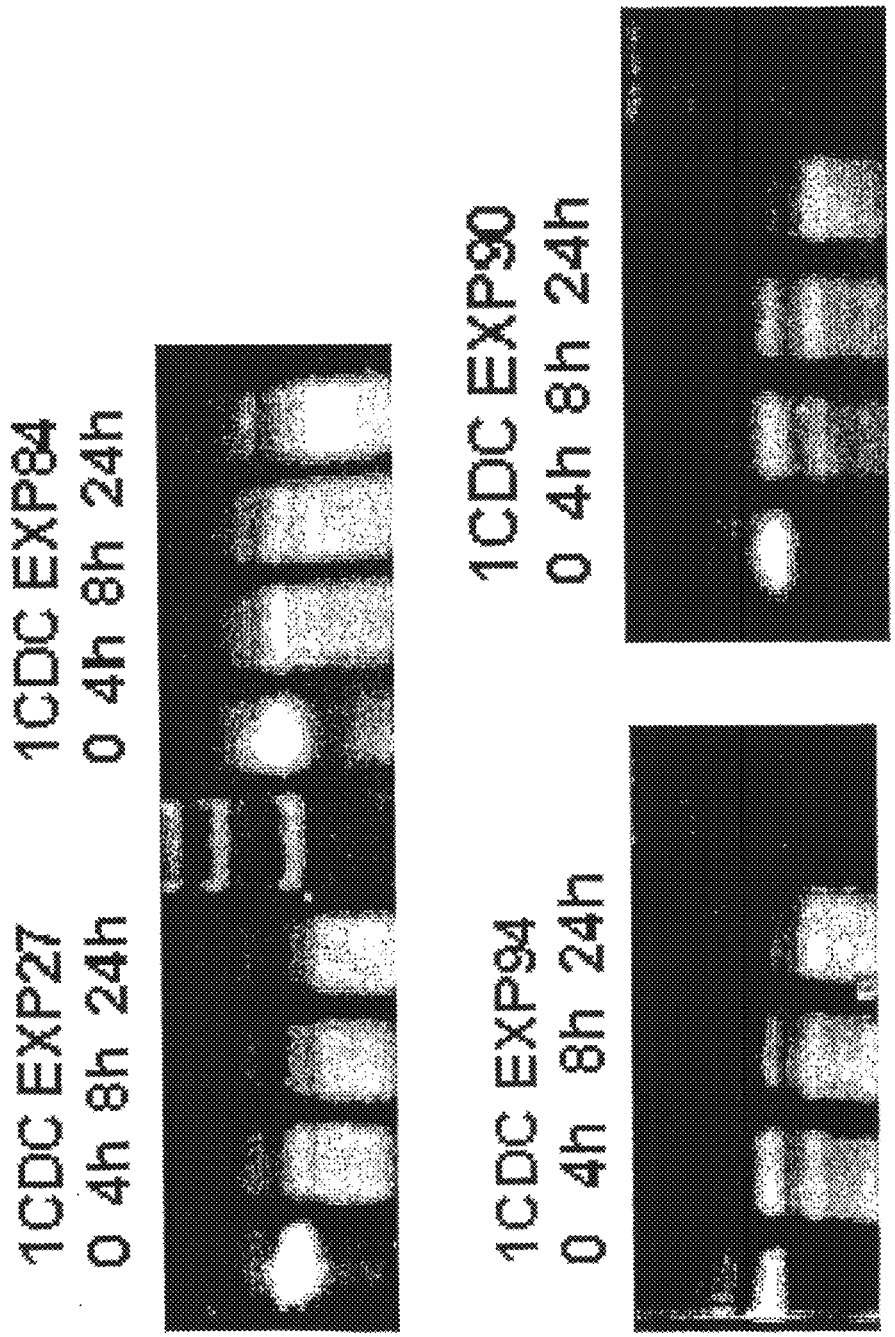

FIG. 6 shows the gene silencing efficiency in HeLaS3 cells transfected with 100 nM modified siRNA according to the present invention and of T98G cells transfected with 10 nM modified siRNA according to the present invention after 2 days and 6 days, respectively;

FIG. 7 shows the gene silencing efficiency in HeLaS3 cells transfected with 100 pM and 50 pM modified siRNA according to the present invention, respectively, with HiPerFect being used as a transfection reagent;

FIG. 8 shows the HPLC spectrum of siRNA modified according to the present invention, incubated in medium with 10% serum (Example 58);

FIG. 9 shows the stability of siRNA (non-modified versus modified according to the present invention) over 72 h; from which it is evident that transfection agents can only slightly prevent the degradation of non-modified siRNA;

FIG. 10 shows a PAGE which shows that modified siRNAs are stable in 100% human serum for at least 8 h, while non-modified siRNA is degraded within minutes.

Figure 11:
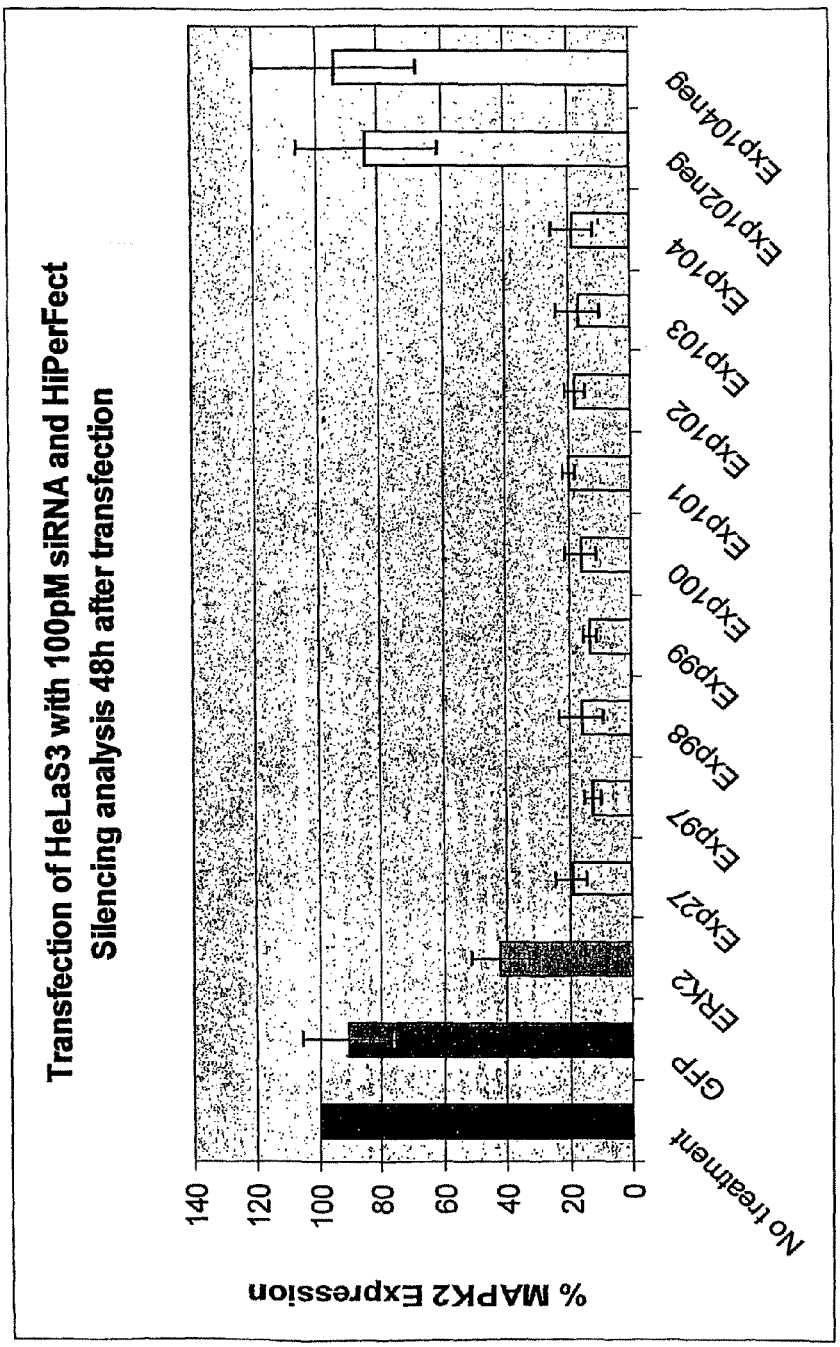
Figure 11:
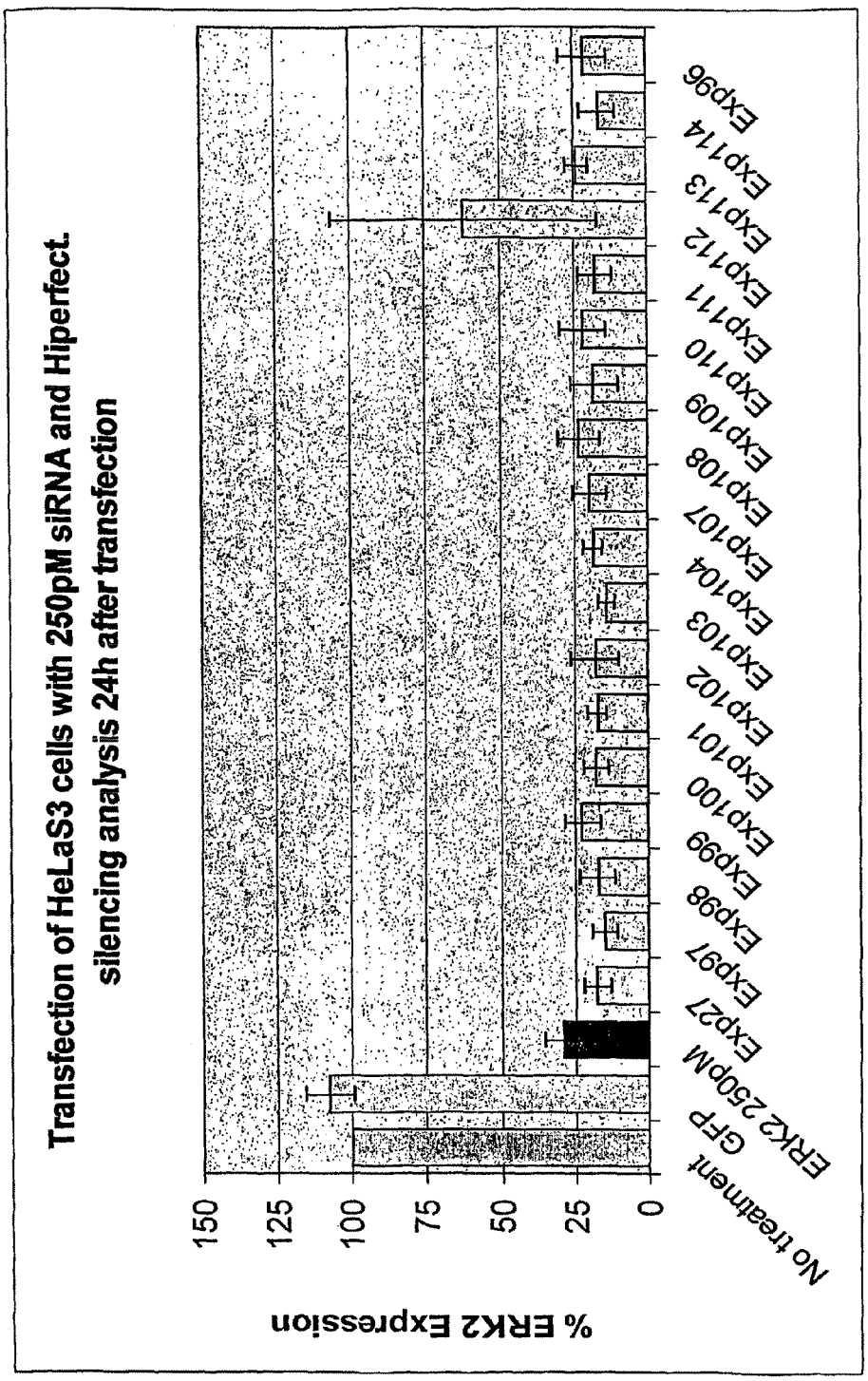
Figure 11:
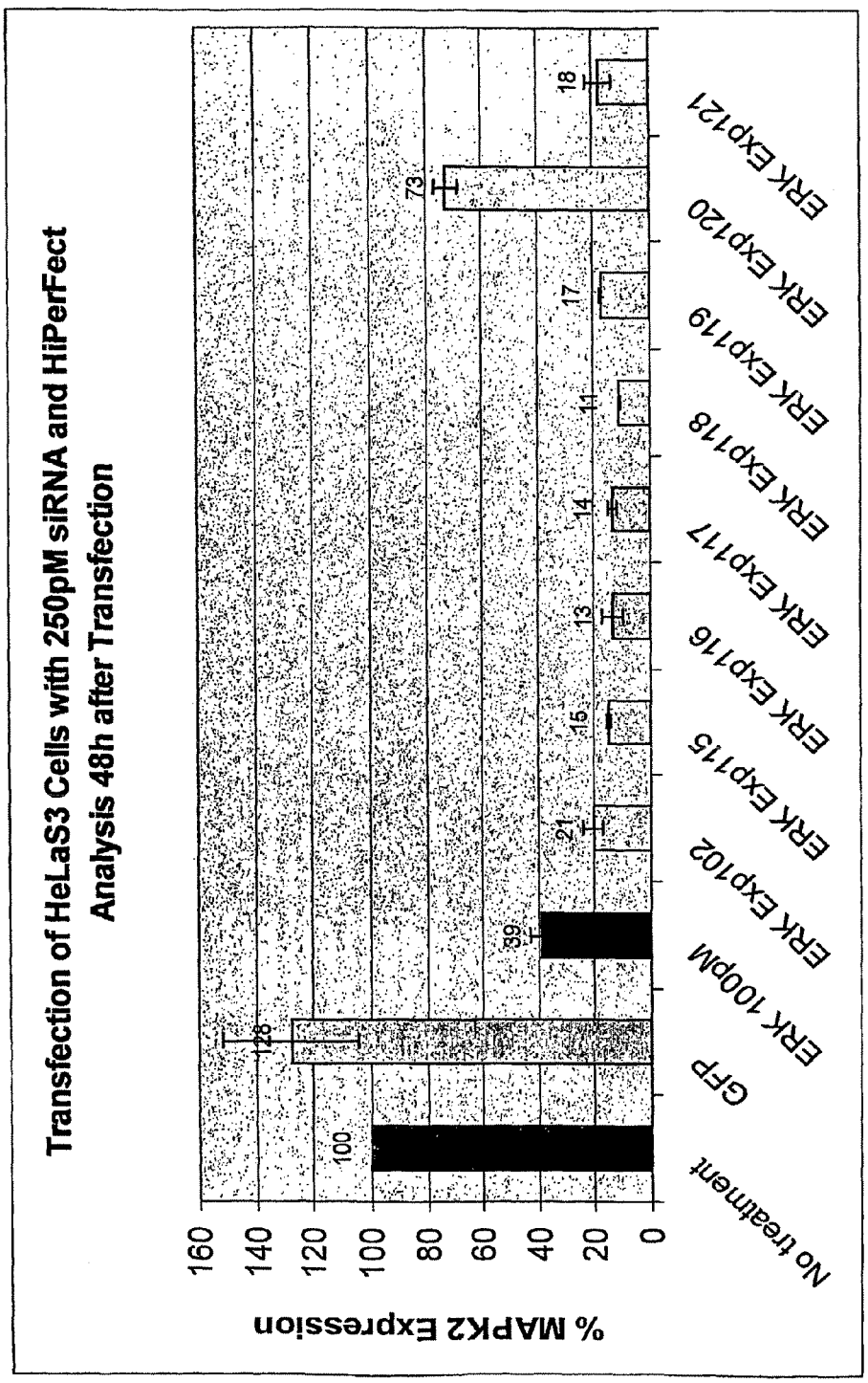

FIG. 11. shows the gene silencing efficiency in HeLaS3 cells transfected with 100 pM and 250 pM siRNA, with HiPerFect being used as transfection reagent.

Figure 12:
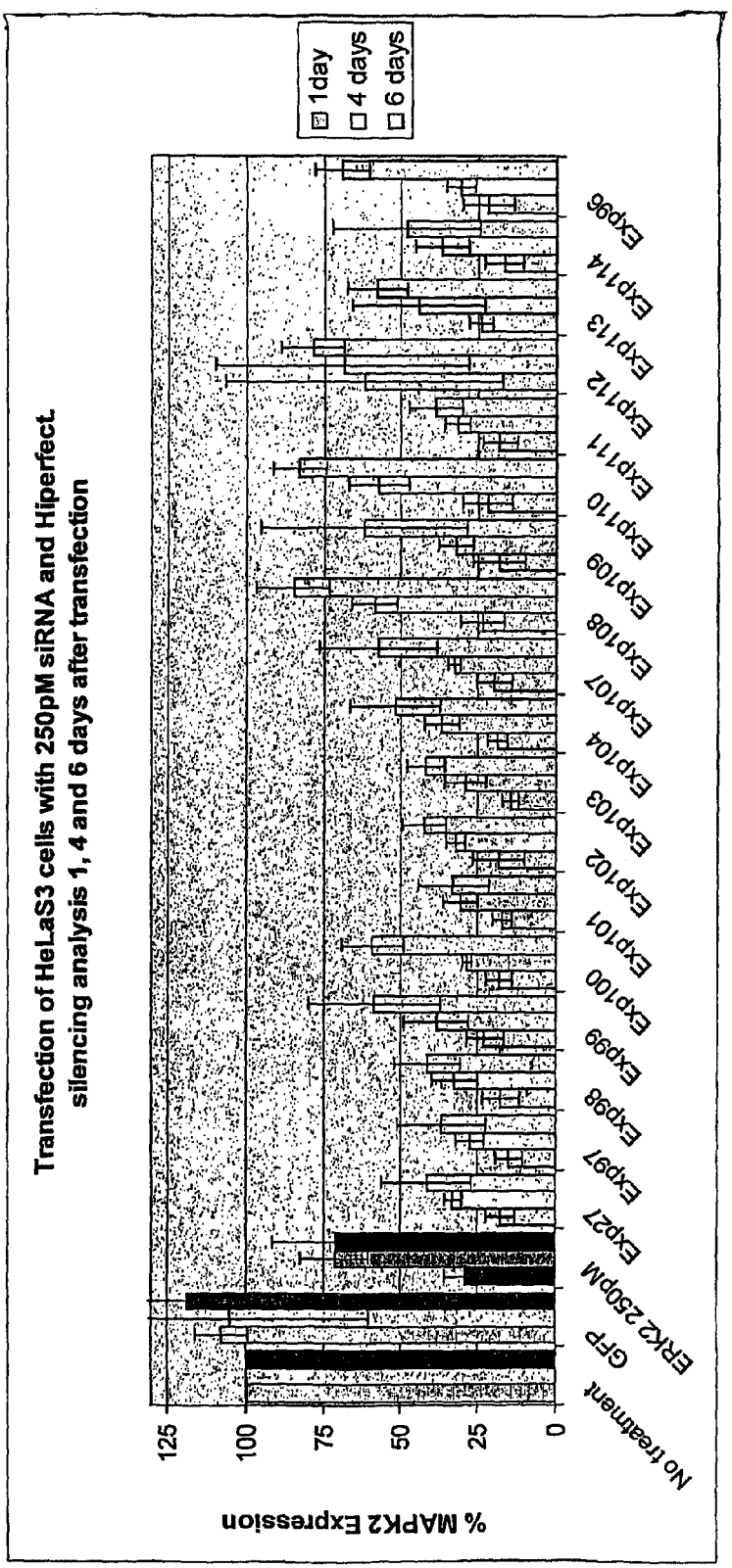

FIG. 12. shows the gene silencing efficiency in HeLaS3 cells transfected with 250 pM siRNA after 1, 4 and 6 days, with HiPerFect being used as a transfection reagent.

Figure 13:
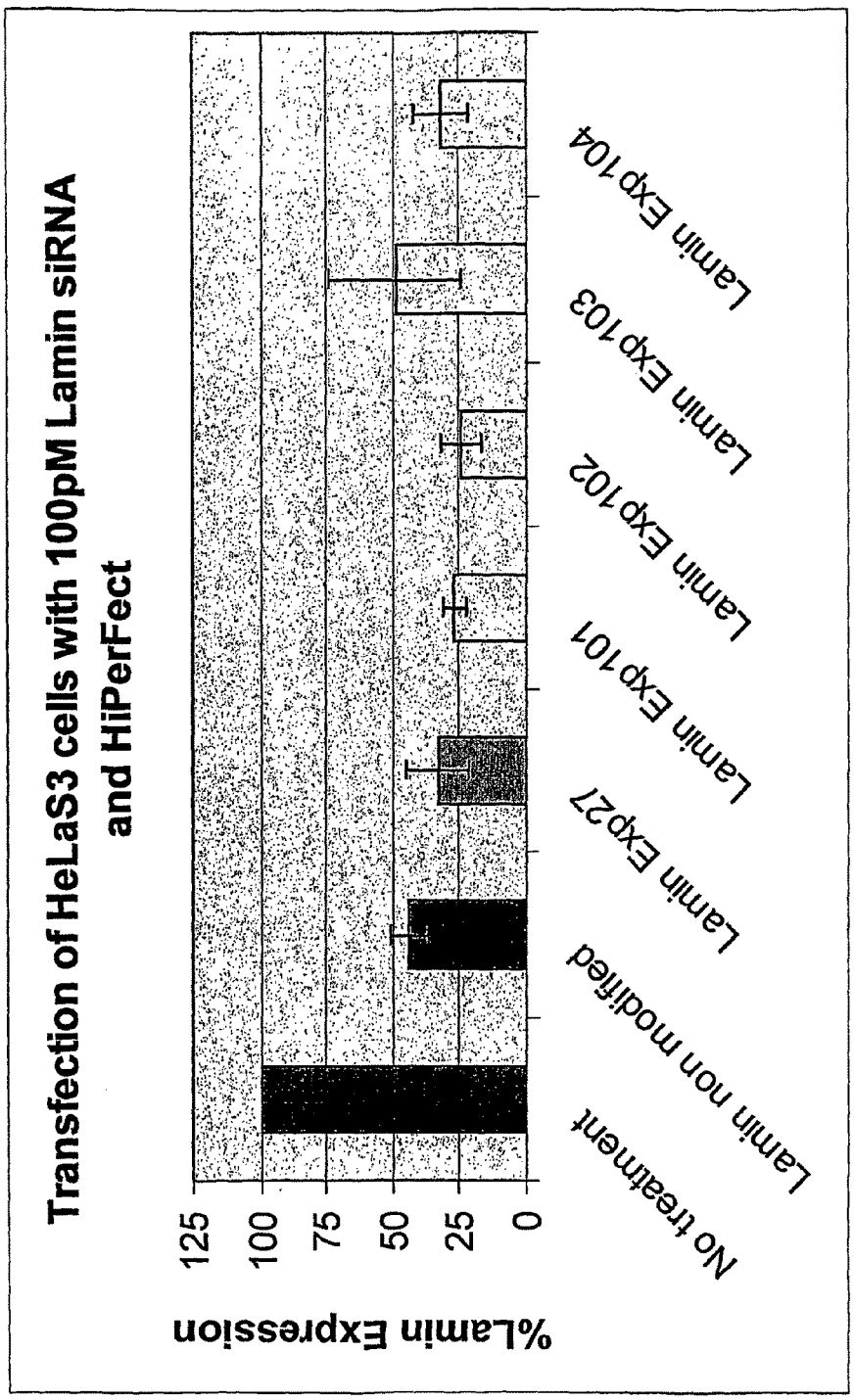
Figure 13:
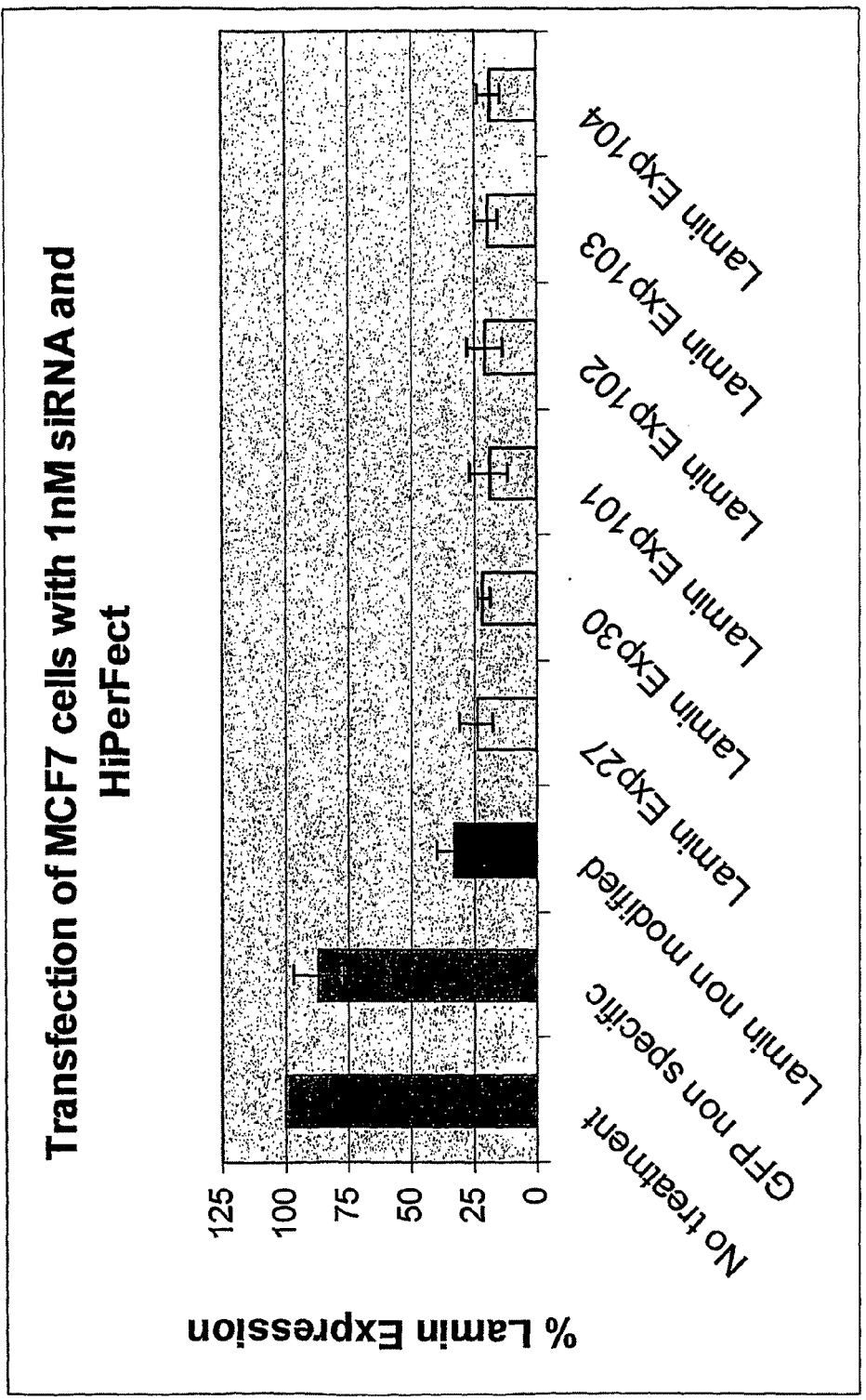

FIG. 13. shows the gene silencing efficiency in HeLaS3 and MCF7 cells transfected with 100 pM and 1 nM siRNA respectively, with HiPerFect being used as a transfection reagent.

Figure 14:
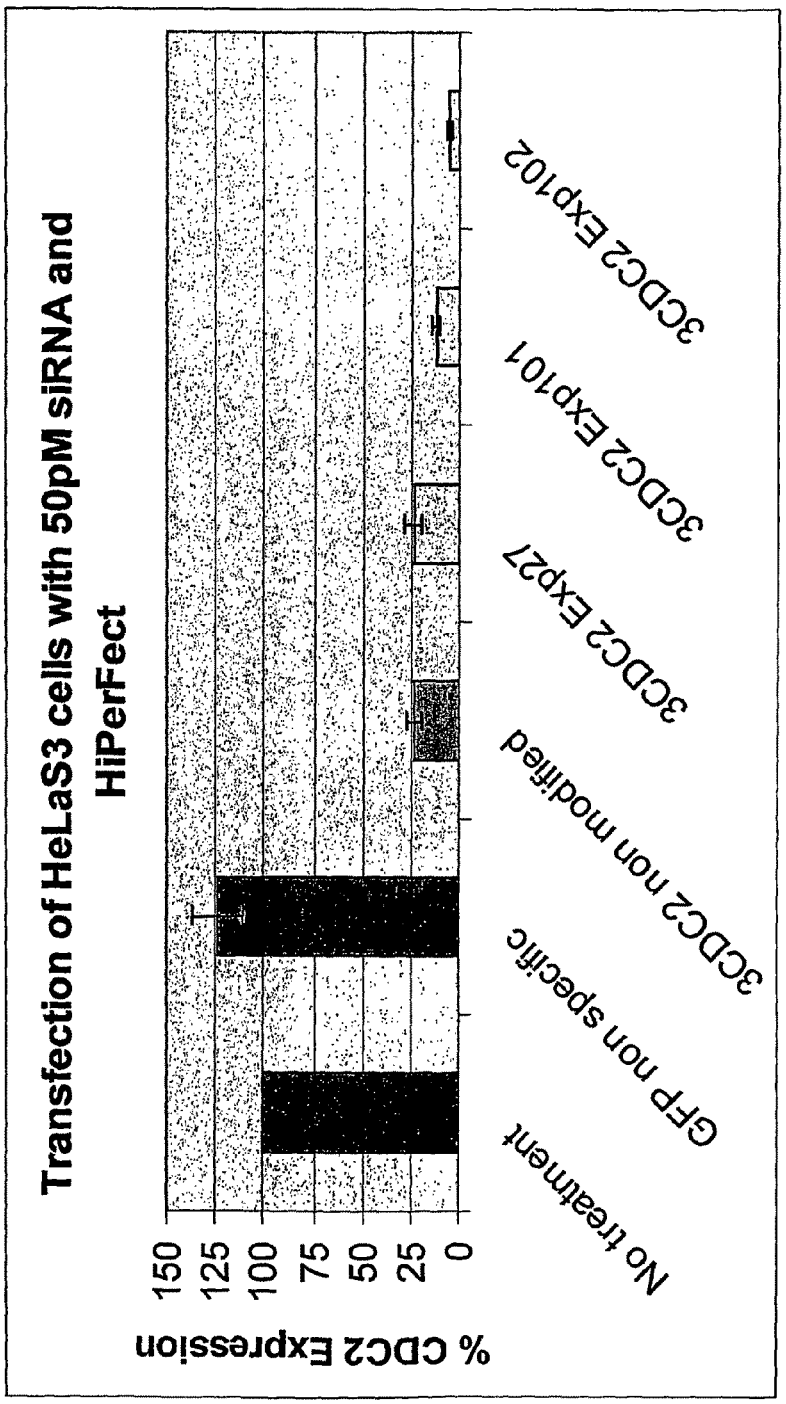
Figure 14:
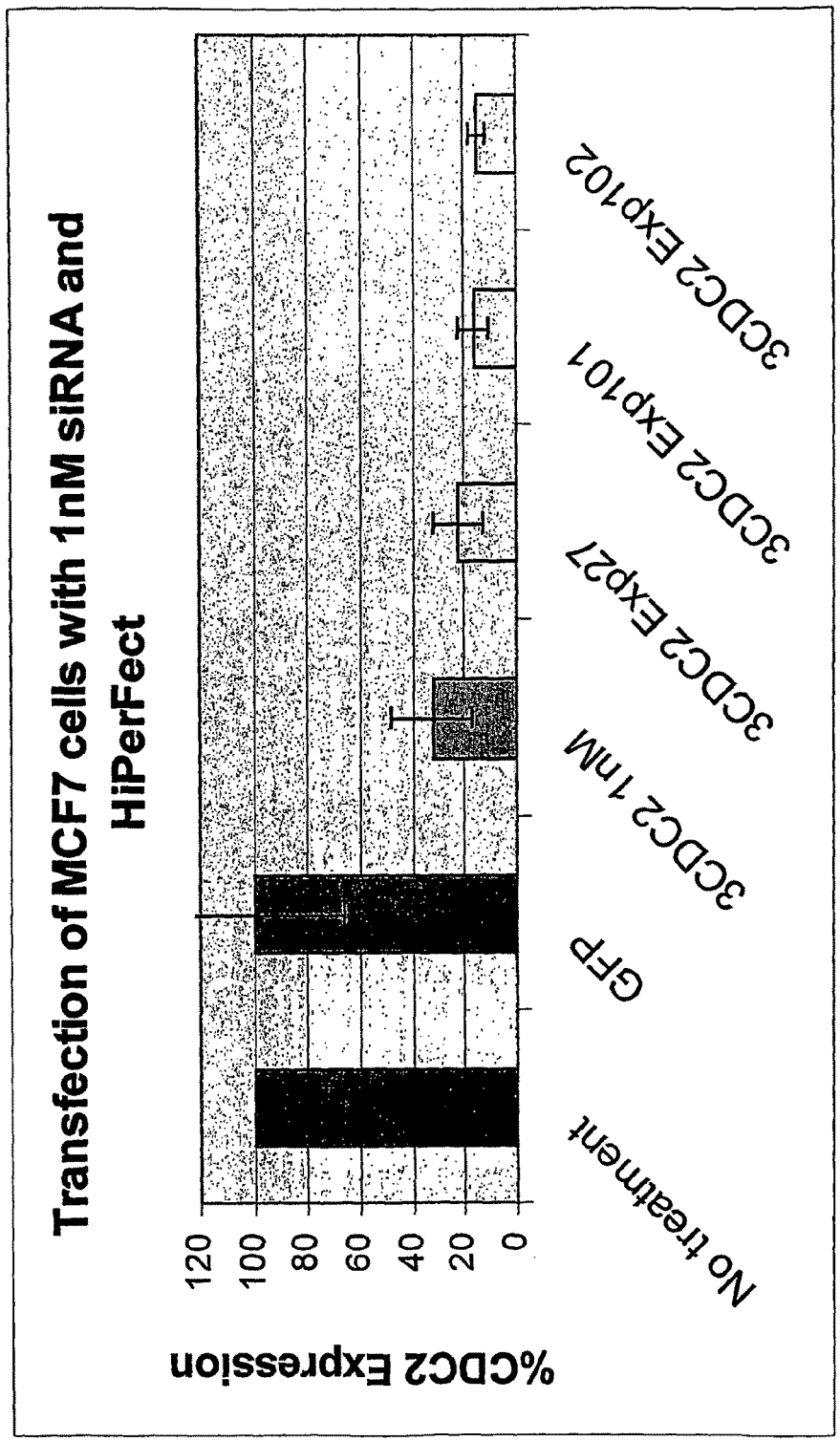

FIG. 14. shows the gene silencing efficiency in HeLaS3 and MCF7 cells transfected with 50 pM and 1 nM siRNA respectively, with HiPerFect being used as a transfection reagent.

Figure 15:
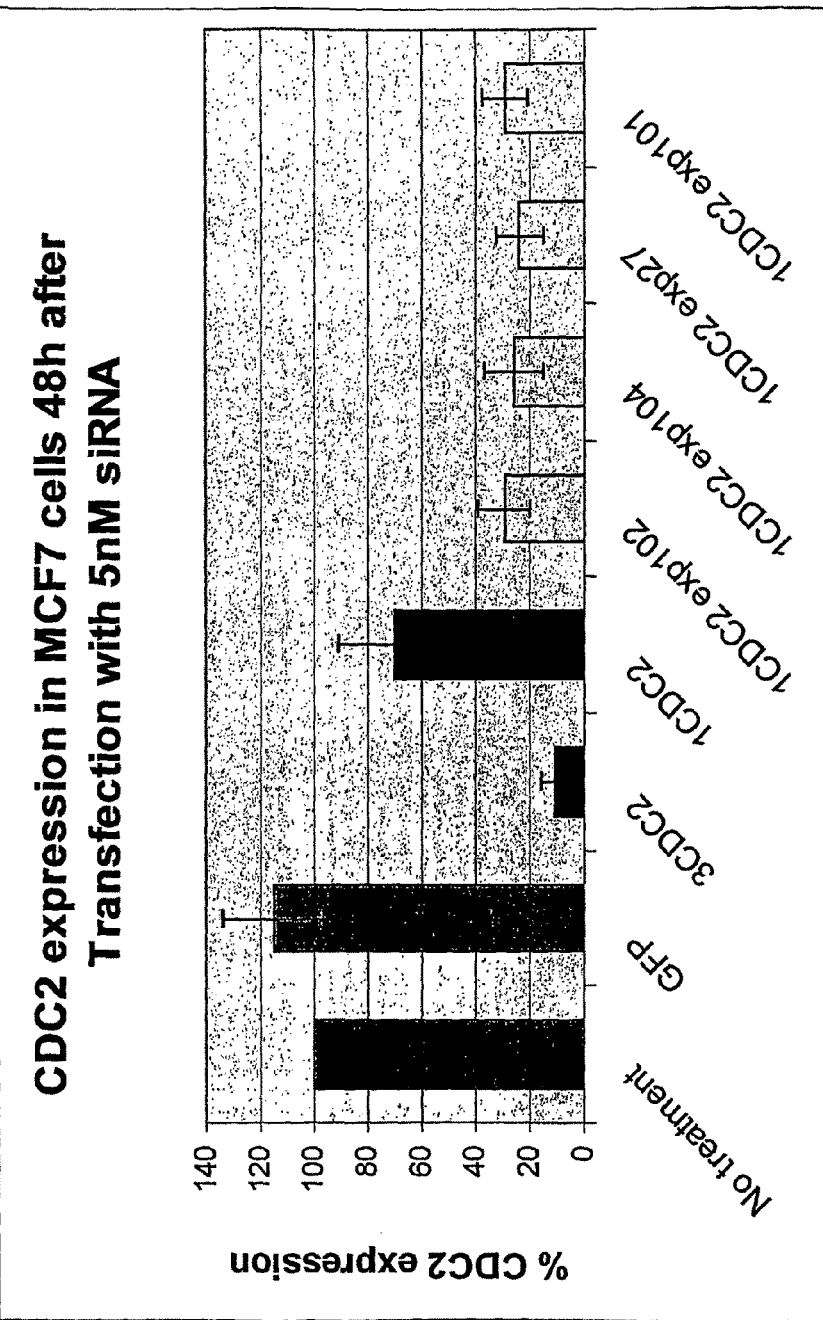

FIG. 15. shows the gene silencing efficiency in MCF7 cells transfected with siRNA after 48 hours.

Figure 16:
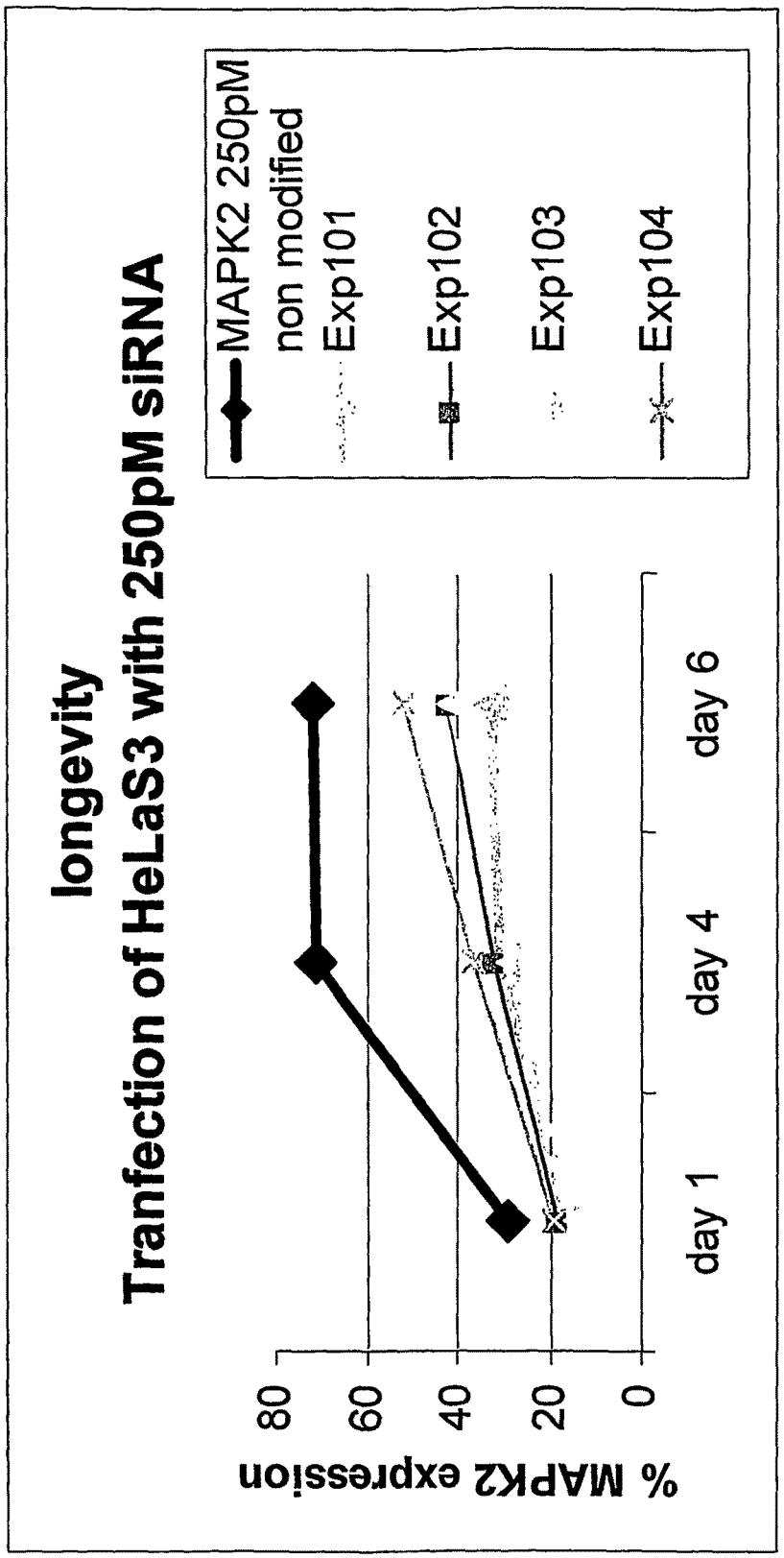
Figure 16:
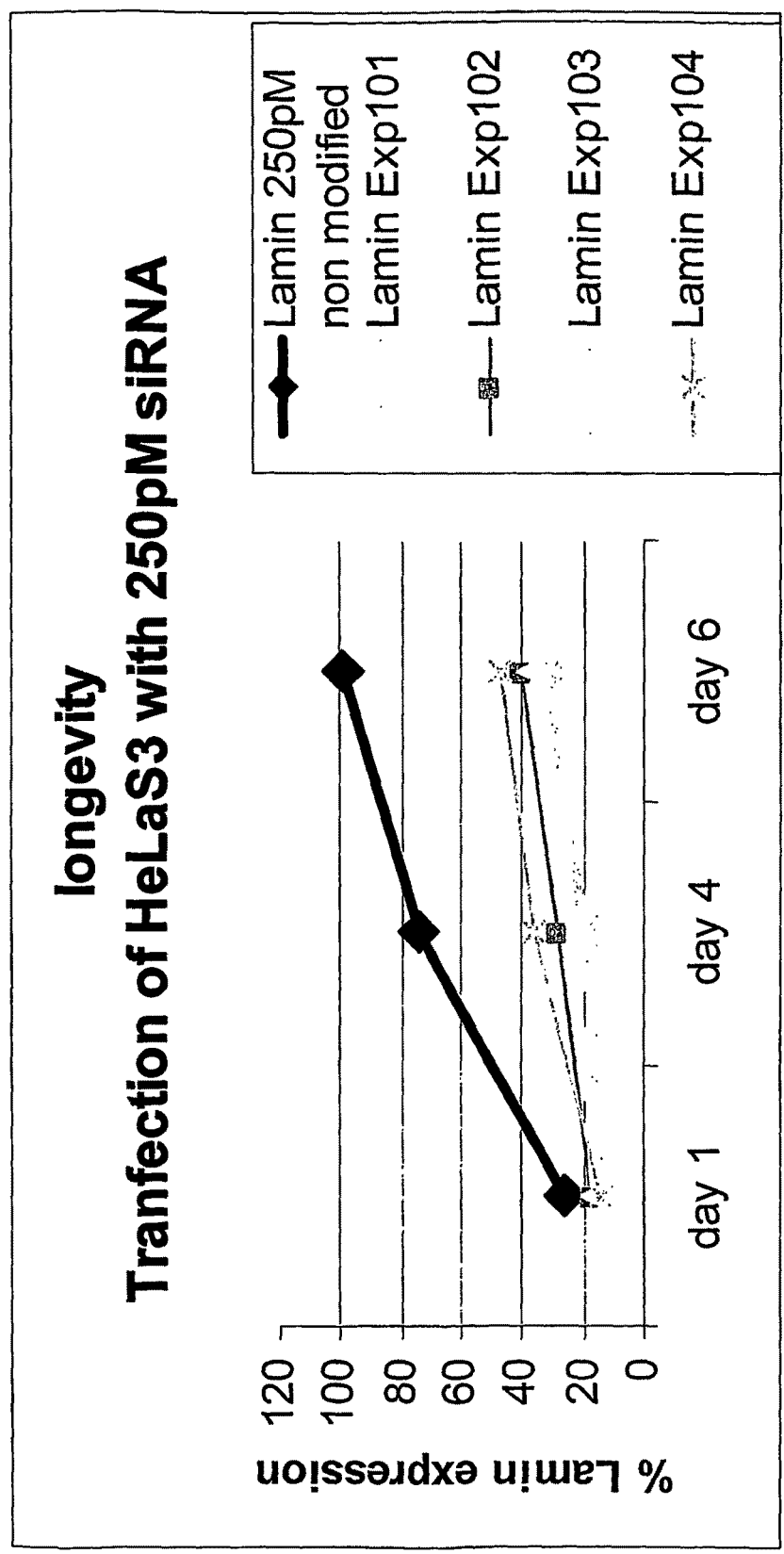
Figure 17A:
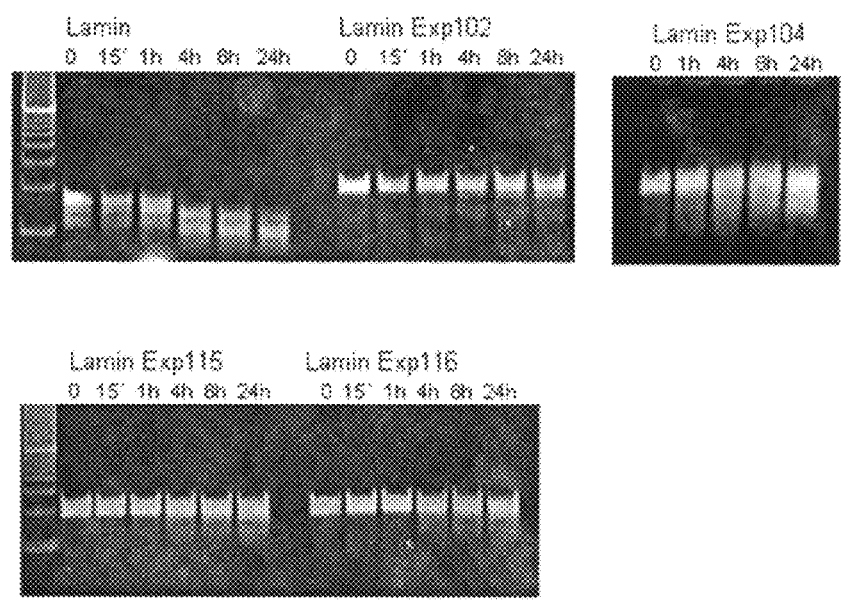
Figure 17B:
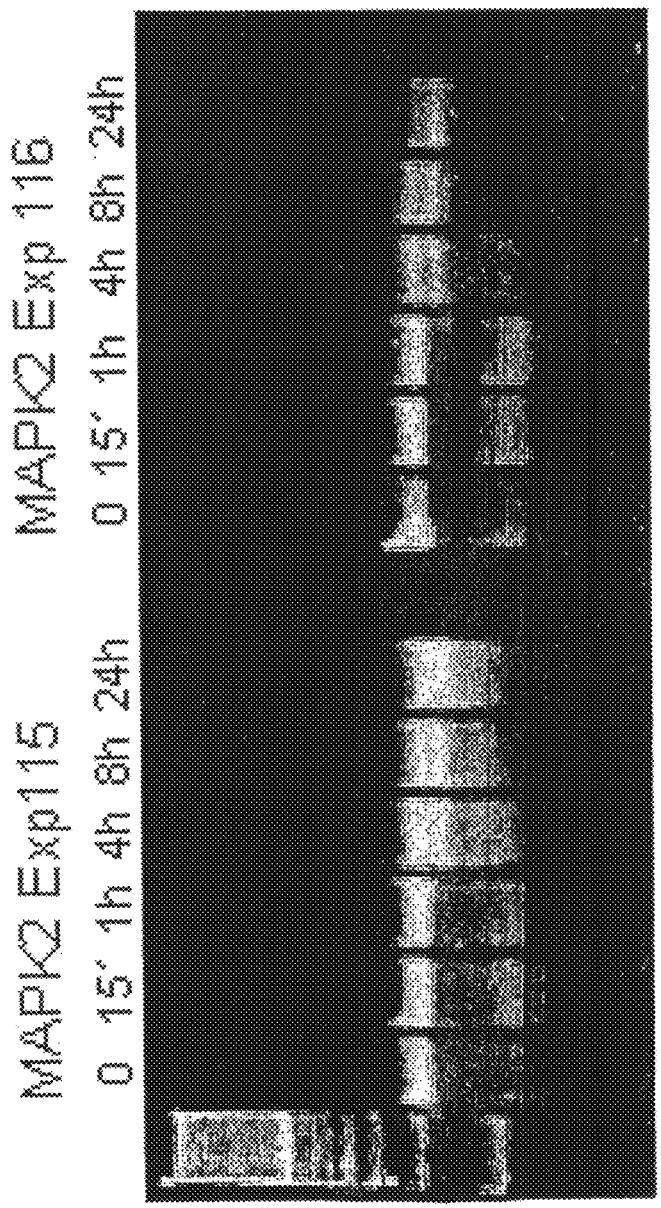
Figure 17B:
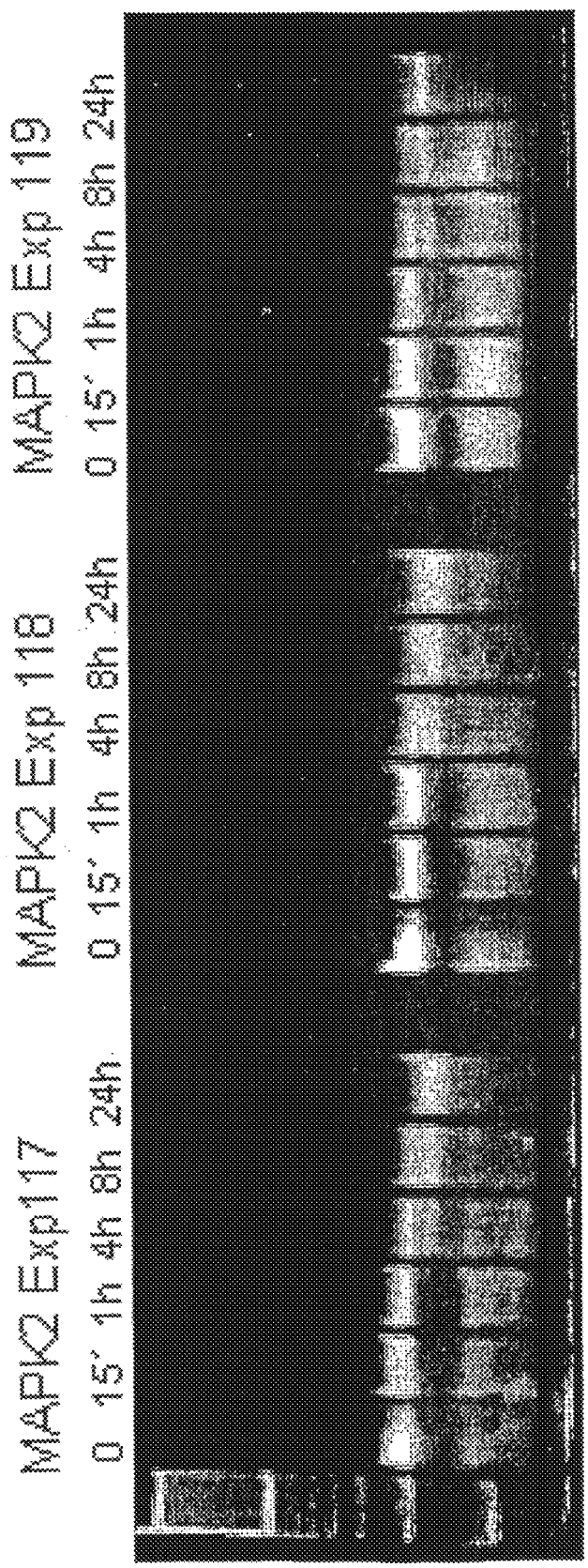
Figure 17B:
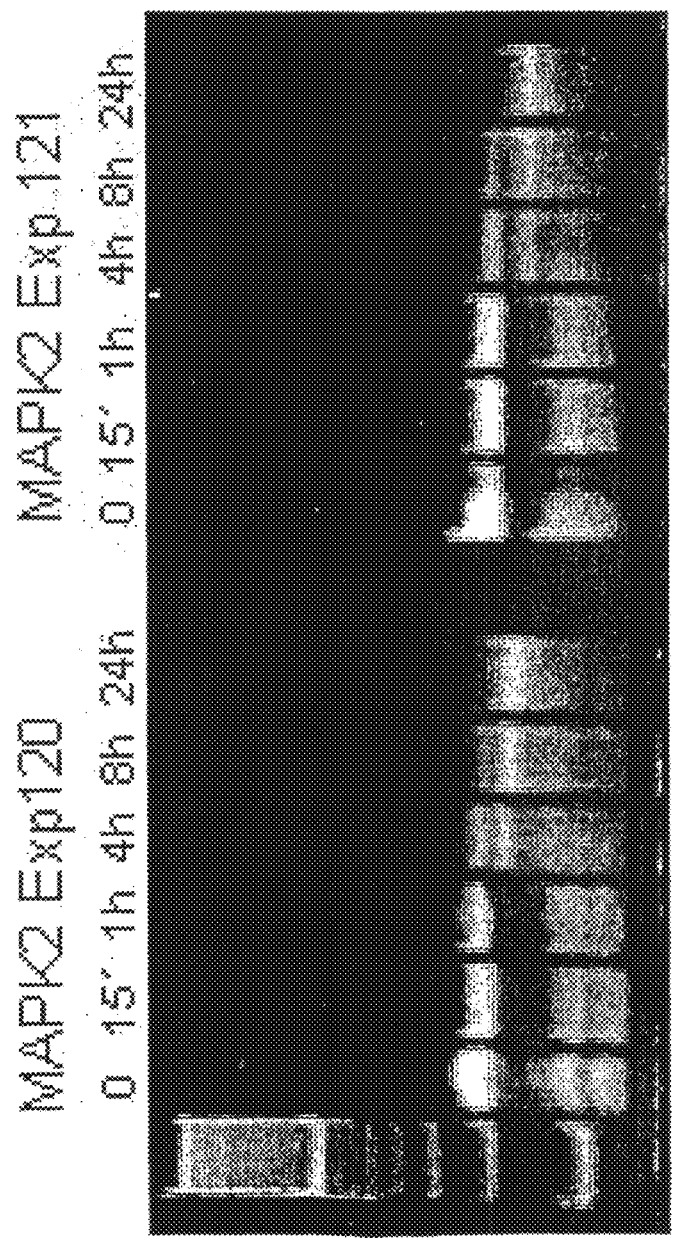
Figure 17C:
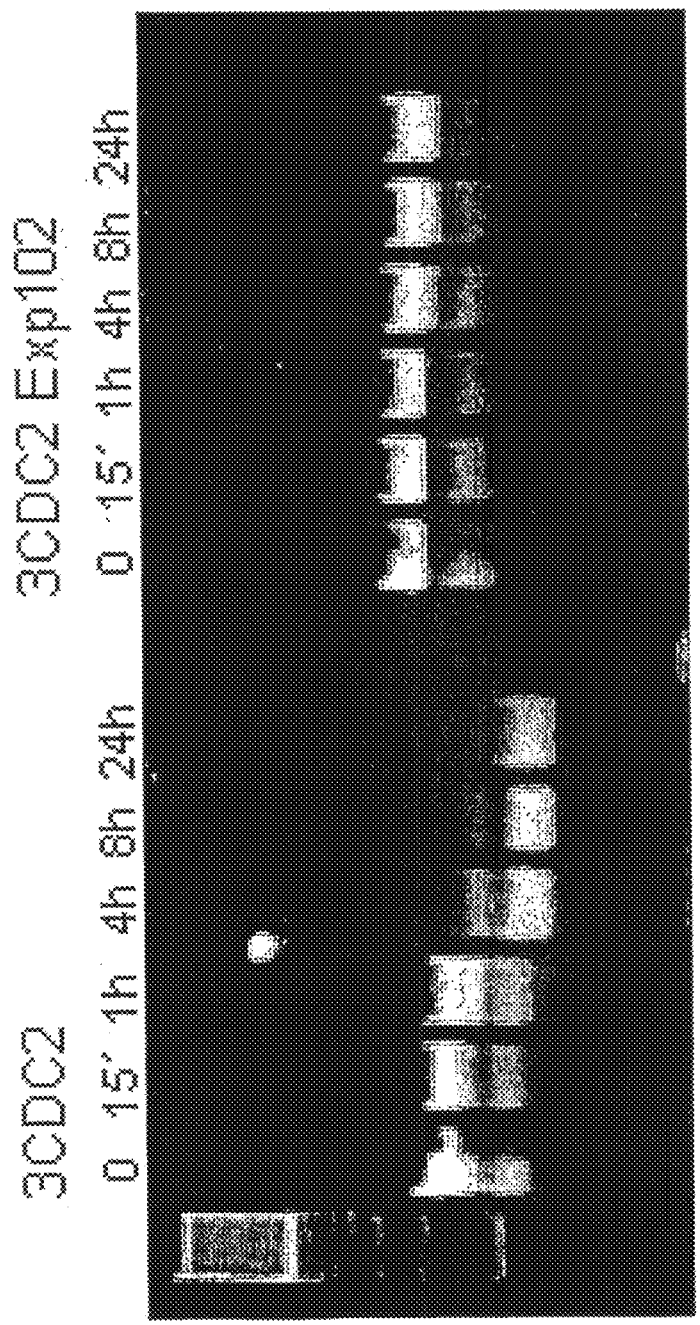
Figure 17C:
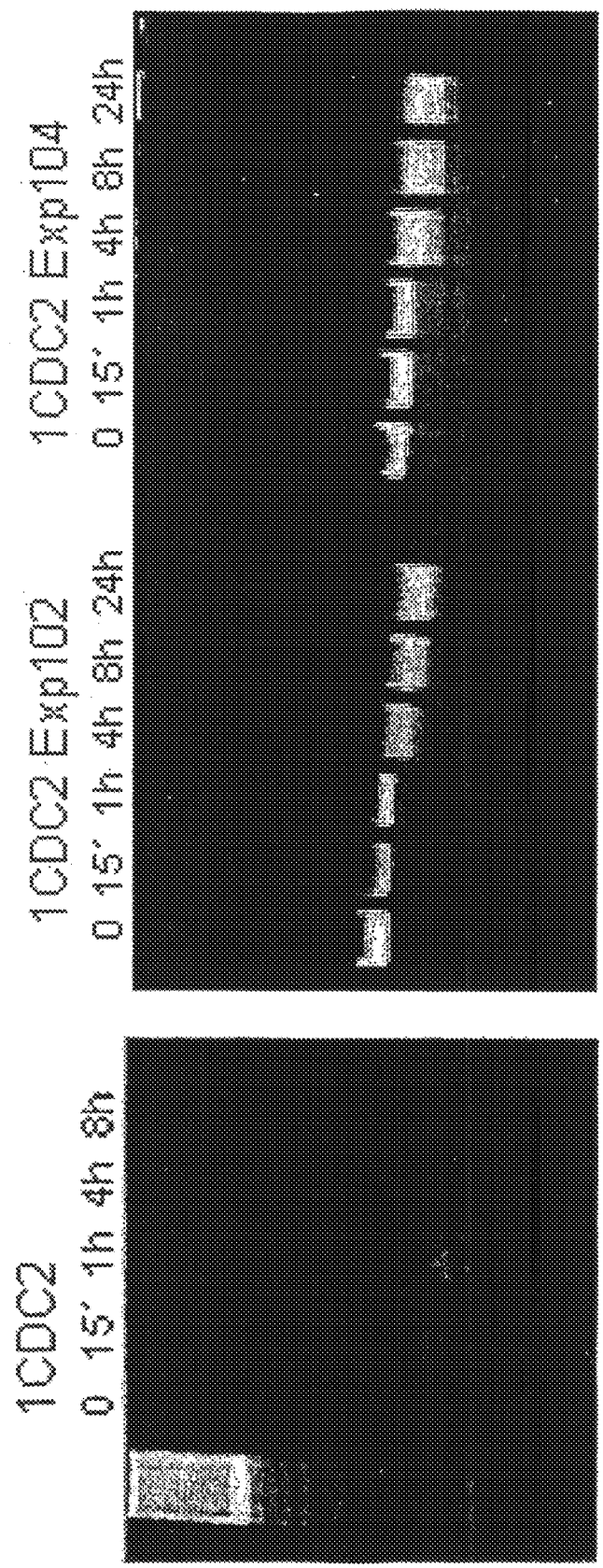

FIG. 16. shows the longevity of MAPK2 and Lamin expression silencing in HeLaS3 cells transfected with 250 pM siRNA after 1, 4 and 6 days.

FIG. 17. Panels A, B and C shows modified siRNAs and their extended stability in human serum.

Examples 1 to 95

The siRNA molecules tested did predominantly comprise 19 nt as the core sequence. In the following Table 1, the core sequence is given between the two straight lines. Left and right of the two straight lines, the 3'- and 5' overhangs are indicated. Moreover, the Table indicates the strand name and the name of the siRNA duplex. The sense strand of each paragraph forms a duplex with one of the antisense strands of the same paragraph. The top row of each paragraph denotes the sense strand (e.g. J8-S, MAPK2S etc.), and the further rows of each paragraph represent the antisense strands (e.g. J8-AS, MAPK2AS etc.). The siRNA duplex name is abbreviated with "exp 1" to "exp 95". The following further symbols are used in Table 1:

A, C, G, U: nucleotides with nucleobases adenine, cytosine, guanine, uracil dA, dC, dG, dT, dU: 2'-deoxy-modified nucleotides niA, mC, mG, mT, mU: 2'-methoxy-modified nucleotides $U^{3'\wedge 5'}$ U: 3' to 5 Tormacetal linkage $U^{2'\wedge 5'}$ U: 2' to 5' formacetal linkage Ac2, Cc2, Gc2, Tc2, Uc2: 2'-hydroxyethylmethyl-modified nucleotides Uc8: 3'-octyloxymethyl modified nucleotides MAPK2S and MAPK2AS: nonmodified 3VIAPK2 sense and antisense respectively $U^{3'\wedge 5'}$ U represents a 3' to 5' formacetal linkage as shown below in formula A:

Dc2: 2'-hydroxyethylmethyl-modified diaminopurine nucleotides

FORMULA A

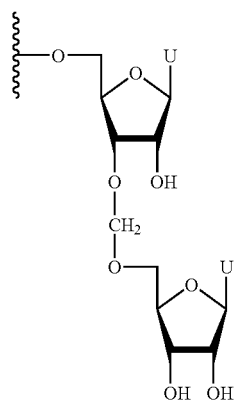

$U^{2'^{\wedge}5'}$ represents a 2' to 5' formacetal linkage as shown below in formula B:

FORMULA B

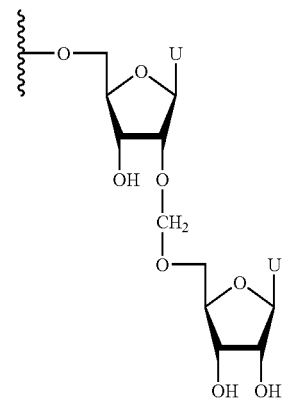

Ac2, Cc2, Gc2, Tc2, Uc2 represent 2'-hydroxyethylm-ethyl-modified nucleotides according to formula C shown below:

FORMULA C

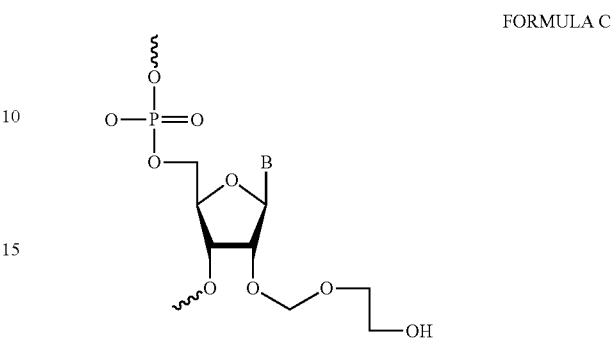

(B = nucleobase: adenine, cytosine, thymine, guanine, uracil, respectively)

Uc8 represents 3'-octyloxymethyl modified nucleotides according to formula D shown below:

FORMULA D

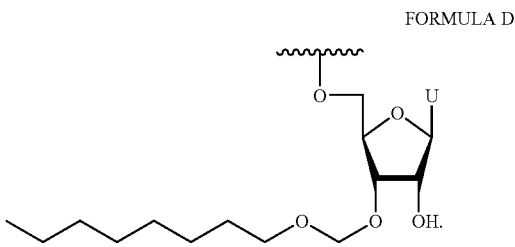

The compound according to formula D is connected via a phosphodiester to the 5'-oxygen of the nucleoside

TABLE 1

| overhang | core sequence | | | | | | | | | | | | | | | | | overhang | strand name | siRNA duplex name | SEQ ID* |
|---|---|---|---|---|---|---|---|---|---|---|---|---|---|---|---|---|---|---|---|---|---|
| 5'- | | U | G | C | U | G | A | C | U | C | C | A | A | A | G | C | U | C U G | $U^{3'^{\wedge}5'}U$ -3' | J8-S | | 18(s/m1)) |
| 3'-$U^{3'^{\wedge}5'}U$ | A | C | G | A | C | U | G | A | G | G | U | U | U | C | G | A | G A C | -5' | J8-AS | exp 2 | 19(a/m2) |
| 3'- dU dU | A | C | G | A | C | U | G | A | G | G | U | U | U | C | G | A | G A C | -5' | MAPK2AS | exp 5 | 20(a/m3) |
| 5'- | | U | G | C | U | G | A | C | U | C | C | A | A | A | G | C | U C U G | $U^{2'^{\wedge}5'}U$ -3' | J7-S | | 21(s/m4) |
| 3'-$U^{2'^{\wedge}5'}U$ | A | C | G | A | C | U | G | A | G | G | U | U | U | C | G | A | G A C | -5' | J7-A | exp 1 | 22(a/m5) |
| | | | | | | | | | | | | | | | | | | | MAPK2A | | 23(a/m6) |
| 3'- dU dU | A | C | G | A | C | U | G | A | G | G | U | U | U | C | G | A | G A C | -5' | S | exp 3 | |
| 5'- | | U | G | C | U | G | A | C | U | C | C | A | A | A | G | C | U C U G | dU dU -3' | MAPK2S | | 24(s/m7) |
| 3'-$U^{2'^{\wedge}5'}U$ | A | C | G | A | C | U | G | A | G | G | U | U | U | C | G | A | G A C | -5' | J7-AS | exp 4 | 25(a/m8) |

TABLE 1-continued

| overhang | core sequence | overhang | strand name | siRNA duplex name | SEQ ID* |
|---|---|---|---|---|---|
| 3'-U$^{3'\wedge 5'}$U | A C G A C U G A G G U U U C G A G A C | -5' | J8-AS | exp 6 | 26(a/m9) |
| 3'-U$^{3'\wedge 5'}$U | mA C G A C U G A G G U U U C G A G A C | -5' | J9-AS | exp 9 | 27(a/m10) |
| 5'- | U G C U G A C U C C A A A G C U C U G U$^{3'\wedge 5'}$U | -3' | J9-S | | 28(s/m11) |
| 3'-U$^{3'\wedge 5'}$U | mA C G A C U G A G G U U U C G A G A C | -5' | J9-AS | exp 7 MAPK2A | 29(a/m12) 30(a/m13) |
| 3'- dU dU | A C G A C U G A G G U U U C G A G A C | -5' | S | exp 8 | |
| 5'- mA mA | U G C U G A C U C C A A A G C U C U G U$^{3'\wedge 5'}$U | -3' | J10-S | | 31(s/m14) |
| 3'-U$^{3'\wedge 5'}$U | A C G A C U G A G G U U U C G A G A C | -5' | J8-AS | exp 10 | 32(a/m15) |
| 3'- mU mU | A C G A C U G A G G U U U C G A G A C | -5' | J15-AS | exp 11 | 33(a/m16) |
| 3'- mU U | A C G A C U G A G G U U U C G A G A C | -5' | J16-AS | exp 12 MAPK2A | 34(a/m17) 35(a/m17) |
| 3'- dU dU | A C G A C U G A G G U U U C G A G A C | -5' | S | exp 13 | |
| 5'- mA mA | U G C U G A C U C C A A A G C U C U mG U$^{3'\wedge 5'}$U | -3' | J13-S | | 36(s/m18) |
| 3'-U$^{3'\wedge 5'}$U | A C G A C U G A G G U U U C G A G A C | -5' | J8-AS | exp 14 | 37(a/m19) |
| 3'- mU mU | A C G A C U G A G G U U U C G A G A C | -5' | J15-AS | exp 15 | 38(a/m20) |
| 3'- mU U | A C G A C U G A G G U U U C G A G A C | -5' | J16-AS | exp 16 MAPK2A | 39(a/m21) 40(a/m22) |
| 3'- dU dU | A C G A C U G A G G U U U C G A G A C | -5' | S | exp 17 | |
| 5'- mA mA | U G C U G A C U C C A A A G C U C U mG mU mU | -3' | J11-S | | 41(s/m23) |
| 3'-U$^{3'\wedge 5'}$U | A C G A C U G A G G U U U C G A G A C | -5' | J8-AS | exp 18 | 42(a/m24) |
| 3'-mU mU | A C G A C U G A G G U U U C G A G A C | -5' | J15-AS | exp 19 | 43(a/m25) |
| 3'- mU U | A C G A C U G A G G U U U C G A G A C | -5' | J16-AS | exp 20 MAPK2A | 44(a/m26) 45(a/m27) |
| 3'- dU dU | A C G A C U G A G G U U U C G A G A C | -5' | S | exp 21 | |
| 5'- mA mA | U G C U G A C U C C A A A G C U C U mG mU mU | -3' | J17-S | | 46(s/m28) |
| 3'-U$^{3'\wedge 5'}$U | A C G A C U G A G G U U U C G A G A C | -5' | J8-AS | exp 22 | 47(a/m29) |
| 3'- mU mU | A C G A C U G A G G U U U C G A G A C | -5' | J15-AS | exp 23 | 48(a/m30) |

TABLE 1-continued

| overhang | core sequence | | | | | | | | | | | | | | | | | | | overhang | strand name | siRNA duplex name | SEQ ID* |
|---|---|---|---|---|---|---|---|---|---|---|---|---|---|---|---|---|---|---|---|---|---|---|---|
| 3'- mU | U | A | C | G | A | C | U | G | A | G | G | U | U | U | C | G | A | G | A | C | -5' J16-AS | exp 24 | 49(a/m31) |
|  |  |  |  |  |  |  |  |  |  |  |  |  |  |  |  |  |  |  |  |  | MAPK2A | | 50(a/m32) |
| 3'- dU | dU | A | C | G | A | C | U | G | A | G | G | U | U | U | C | G | A | G | A | C | -5' S | exp 25 | |
| 5'- mA | mA | U | G | C | U | G | A | C | U | C | C | A | A | A | G | C | dU | dC | dU | mG U³'^5'U | -3' J18-S | | 51(s/m33) |
| 3'- U³'^5'U | | A | C | G | A | C | U | G | A | G | G | U | U | U | C | G | A | G | A | mC | -5' J22-AS | exp 26 | 52(a/m34) |
| 3'- U³'^5'U | | A | C | G | A | C | U | G | A | G | G | U | U | U | C | G | A | G | A | dC | -5' J23-AS | exp 27 | 53(a/m35) |
| 3'- U³'^5'U | | A | C | G | A | C | U | G | A | G | G | U | U | U | C | G | dA | dG | dA | dC | -5' J26-AS | exp 28 | 54(a/m36) |
| 3'- mU | mU | A | C | G | A | C | U | G | A | G | G | U | U | U | C | G | A | G | A | mC | -5' J27-AS | exp 29 | 55(a/m37) |
| 3'- mU | mU | A | C | G | A | C | U | G | A | G | G | U | U | U | C | G | A | G | A | dC | -5' J28-AS | exp 30 | 56(a/m38) |
| 3'- mU | mU | A | C | G | A | C | U | G | A | G | G | U | U | U | C | G | dA | dG | dA | dC | -5' J29-AS | exp 31 | 57(a/m39) |
| 3'- Uc8 | mU | A | C | G | A | C | U | G | A | G | G | U | U | U | C | G | A | G | A | mC | -5' J24-AS | exp 32 | 58(a/m40) |
| 3'- Uc8 | mU | A | C | G | A | C | U | G | A | G | G | U | U | U | C | G | A | G | A | dC | -5' J25-AS | exp 33 | 59(a/m41) |
| 5'- dA | dA | U | G | C | U | G | A | C | U | C | C | A | A | A | G | C | dU | dC | dU | mG U³'^5'U | -3' J19-S | | 60(s/m42) |
| 3'- U³'^5'U | | A | C | G | A | C | U | G | A | G | G | U | U | U | C | G | A | G | A | mC | -5' J22-AS | exp 34 | 61(a/m43) |
| 3'- U³'^5'U | | A | C | G | A | C | U | G | A | G | G | U | U | U | C | G | A | G | A | dC | -5' J23-AS | exp 43 | 62(a/m44) |
| 3'- U³'^5'U | | A | C | G | A | C | U | G | A | G | G | U | U | U | C | G | dA | dG | dA | dC | -5' J26-AS | exp 38 | 63(a/m45) |
| 3'- mU | mU | A | C | G | A | C | U | G | A | G | G | U | U | U | C | G | A | G | A | mC | -5' J27-AS | exp 39 | 64(a/m46) |
| 3'- mU | mU | A | C | G | A | C | U | G | A | G | G | U | U | U | C | G | A | G | A | dC | -5' J28-AS | exp 40 | 65(a/m47) |
| 3'- mU | mU | A | C | G | A | C | U | G | A | G | G | U | U | U | C | G | dA | dG | dA | dC | -5' J29-AS | exp 41 | 66(a/m48) |
| 3'- Uc8 | mU | A | C | G | A | C | U | G | A | G | G | U | U | U | C | G | A | G | A | mC | -5' J24-AS | exp 51 | 67(a/m49) |
| 3'- Uc8 | mU | A | C | G | A | C | U | G | A | G | G | U | U | U | C | G | A | G | A | dC | -5' J25-AS | exp 37 | 68(a/m50) |
| 5'- mA | mA | U | G | C | U | G | A | C | U | C | C | A | A | A | G | C | dU | dC | dU | dG U³'^5'U | -3' J20-S | | 69(s/m51) |
| 3'- U³'^5'U | | A | C | G | A | C | U | G | A | G | G | U | U | U | C | G | A | G | A | mC | -5' J22-AS | exp 42 | 70(a/m52) |
| 3'- U³'^5'U | | A | C | G | A | C | U | G | A | G | G | U | U | U | C | G | A | G | A | dC | -5' J23-AS | exp 35 | 71(a/m53) |
| 3'- U³'^5'U | | A | C | G | A | C | U | G | A | G | G | U | U | U | C | G | dA | dG | dA | dC | -5' J26-AS | exp 46 | 72(a/m54) |
| 3'- mU | mU | A | C | G | A | C | U | G | A | G | G | U | U | U | C | G | A | G | A | mC | -5' J27-AS | exp 47 | 73(a/m55) |

TABLE 1-continued

| overhang | core sequence | overhang | strand name | siRNA duplex name | SEQ ID* |
|---|---|---|---|---|---|
| 3'- mU mU | A C G A C U G A G G U U U C G A G A dC | -5' | J28-AS | exp 48 | 74(a/m56) |
| 3'- mU mU | A C G A C U G A G G U U U C G dA dG dA dC | -5' | J29-AS | exp 49 | 75(a/m57) |
| 3'- Uc8 mU | A C G A C U G A G G U U U C G A G A mC | -5' | J24-AS | exp 44 | 76(a/m58) |
| 3'- Uc8 mU | A C G A C U G A G G U U U C G A G A dC | -5' | J25-AS | exp 45 | 77(a/m59) |
| 5'- dA dA | U G C U G A C U C C A A A G C dU dC dU dG U³'^5'U | -3' | J21-S | | 78(s/m60) |
| 3'- U³'^5'U | A C G A C U G A G G U U U C G A G A mC | -5' | J22-AS | exp 50 | 79(a/m61) |
| 3'- U³'^5'U | A C G A C U G A G G U U U C G A G A dC | -5' | J23-AS | exp 36 | 80(a/m62) |
| 3'- U³'^5'U | A C G A C U G A G G U U U C G dA dG dA dC | -5' | J26-AS | exp 54 | 81(a/m62) |
| 3'- mU mU | A C G A C U G A G G U U U C G A G A mC | -5' | J27-AS | exp 55 | 82(a/m63) |
| 3'- mU mU | A C G A C U G A G G U U U C G A G A dC | -5' | J28-AS | exp 56 | 83(a/m64) |
| 3'- mU mU | A C G A C U G A G G U U U C G dA dG dA dC | -5' | J29-AS | exp 57 | 84(a/m65) |
| 3'- Uc8 mU | A C G A C U G A G G U U U C G A G A mC | -5' | J24-AS | exp 52 | 85(a/m66) |
| 3'- Uc8 mU | A C G A C U G A G G U U U C G A G A dC | -5' | J25-AS | exp 53 | 86(a/m67) |
| 5'- mA mA | U G C U G A C U C C A A A G C U C mU mG U³'^5'U | -3' | J30-S | | 87(s/m68) |
| 3'- U³'^5'U | A C G A C U G A G G U U U C G A G A mC | -5' | J22-AS | exp 58 | 88(a/m69) |
| 3'- mU mU | A C G A C U G A G G U U U C G A G A mC | -5' | J27-AS | exp 59 | 89(a/m70) |
| 3'- mU mU | A C G A C U G A G G U U U C G A G mA mC | -5' | J35-AS | exp 60 | 90(a/m71) |
| 3'- U³'^5'U | A C G A C U G A G G U U U C G A G mA mC | -5' | J36-AS | exp 73 | 91(a/m72) |
| 3'- U³'^5'U | mA C G A C U G A G G U U U C G A G A mC | -5' | J37-AS | exp 74 | 92(a/m73) |
| 3'- U³'^5'U | mA C G A C U G A G G U U U C G A G mA mC | -5' | J38-AS | exp 75 | 93(a/m74) |
| 5'- mA mA | dU dG dC dU dG dA dC dU dC dC dA dA dA dG dC dU dC mU mG U³'^5'U | -3' | J31-S | | 94(s/m75) |
| 3'- U³'^5'U | A C G A C U G A G G U U U C G A G A mC | -5' | J22-AS | exp 61 | 95(a/m76) |
| 3'- mU mU | A C G A C U G A G G U U U C G A G A mC | -5' | J27-AS | exp 62 | 96(a/m77) |
| 3'- mU mU | A C G A C U G A G G U U U C G A G mA mC | -5' | J35-AS | exp 63 | 97(a/m78) |
| 5'- mA mA mU | dG dC dU dG dA dC dU dC dC dA dA dA dG dC dU mC mU mG U³'^5'U | -3' | J32-S | | 98(a/m79) |

TABLE 1-continued

| overhang | core sequence | overhang | strand name | siRNA duplex name | SEQ ID* |
|---|---|---|---|---|---|
| 3'-U³'^5'U | A C G A C U G A G G U U U C G A G A mC | -5' | J22-AS | exp 64 | 99 (a/m80) |
| 3'- mU mU | A C G A C U G A G G U U U C G A G A mC | -5' | J27-AS | exp 65 | 100 (a/m81) |
| 3'- mU mU | A C G A C U G A G G U U U C G A G mA mC | -5' | J35-AS | exp 66 | 101 (a/m82) |
| 5'- mA mA | dU dG dC dU dG dA dC dU dC dC dA dA dA dG dC dU mC mU mG U³'^5'U | -3' | J33-S | | 102 (s/m83) |
| 3'-U³'^5'U | A C G A C U G A G G U U U C G A G A mC | -5' | J22-AS | exp 67 | 103 (a/m84) |
| 3'- mU mU | A C G A C U G A G G U U U C G A G A mC | -5' | J27-AS | exp 68 | 104 (a/m85) |
| 3'- mU mU | A C G A C U G A G G U U U C G A G mA mC | -5' | J35-AS | exp 69 | 105 (a/m86) |
| 5'- mA mA mU | dG dC dU dG dA dC dU dC dC dA dA dA dG dC dU dC mU mG U³'^5'U | -3' | J34-S | | 106 (s/m87) |
| 3'-U³'^5'U | A C G A C U G A G G U U U C G A G A mC | -5' | J22-AS | exp 70 | 107 (a/m88) |
| 3'- mU mU | A C G A C U G A G G U U U C G A G A mC | -5' | J27-AS | exp 71 | 108 (a/m89) |
| 3'- mU mU | A C G A C U G A G G U U U C G A G mA mC | -5' | J35-AS | exp 72 | 109 (a/m90) |
| 5'- mA mA | U G C U G A C U C C A A A G C Uc2 Cc2 Uc2 Gc2 U³'^5'U | -3' | J47-S | | 110 (s/m91) |
| 3'-U³'^5'U | A C G A C U G A G G U U U C G A G A Cc2 | -5' | J49-AS | exp 88 | 111 (a/m92) |
| 3'-U³'^5'U | A C G A C U G A G G U U U C G A G A dC | -5' | J23-AS | exp 90 | 112 (a/m93) |
| 3'-U³'^5'U | mA C G A C U G A G G U U U C G A G A dC | -5' | J46-AS | exp 94 | 113 (a/m94) |
| 5'- mA mA | U G C U G A C U C C A A A G C Uc2 Cc2 Uc2 mG U³'^5'U | -3' | J48-S | | 114 (s/m95) |
| 3'-U³'^5'U | A C G A C U G A G G U U U C G A G A Cc2 | -5' | J49-AS | exp 89 | 115 (a/m96) |
| 3'-U³'^5'U | A C G A C U G A G G U U U C G A G A dC | -5' | J23-AS | exp 91 | 116 (a/m97) |
| 3'-U³'^5'U | mA C G A C U G A G G U U U C G A G A dC | -5' | J46-AS | exp 95 | 117 (a/m98) |

TABLE 1-continued

| overhang | core sequence | overhang | strand name | siRNA duplex name | SEQ ID* |
|---|---|---|---|---|---|
| 5'- dA dA | U G C U G A C U C C A A A G C dU dC dU dG | U³'^5'U -3' | J45-S | | 118 (s/m97) |
| 3'- U³'^5'U | mA C G A C U G A G G U U U C G A G A dC | -5' | J46-AS | exp 92 | 119 (a/m98) |
| 3'- U³'^5'U | A C G A C U G A G G U U U C G A G A dC | -5' | J23-AS | exp 93 | 120 (a/m99) |

*: SEQ ID: In this field, the number in front of the parenthesis indicates the SEQ ID NO as listed in field <210> of the sequence listing. The letters "s" or "a" indicate whether the strand is a sense strand (s) or the respective antisense strand (a). The letter "m" in combination with the respective number represents a consecutive numbering of the respective modification of this sense or antisense strand as outlined in field <223> of the sequence listing.

From Table 1, the modifications of siRNA duplexes can be seen. Long chains or other major modification, for example a 2'-acetal modification (modification (d)), on the 5'-end of the antisense strand, are not tolerated by the siRNA. On the 5' end of sense strand, any kind of modification has been tolerated. On the 3' end of the sense and the antisense strand, all kinds of modifications (a) to (e) were also tolerated. Deoxy-modifications on the whole sense strand in combination with the methoxy-modifications on 5'- and 3'-end of this strand (see e.g. Exp. 61-72) can lead to siRNA inactivation. One or more methoxy modification(s) of the 5'-end of the antisense strand in combination with methoxy-modification(s) on the 3'-end of the antisense strand can decrease siRNA activity (see Exp. 60, Exp. 73-75).

While Table 1 refers to siRNA sequences for the target MAPK2, Table 2 shows siRNA sequences for the targets Lamin AC and CDC2, respectively. Otherwise, what was said with regard to Table 1, also applies to Table 2.

TABLE 2 sIRNA sequences for the targets Lamin AC and CDC2.

| overhang | core sequence | overhang | strand name | siRNA duplex name | SEQ ID* |
|---|---|---|---|---|---|
| 5'- mA mA | C U G G A C U U C C A G A A G dA dA dC mA | U³'^5'U -3' | J45-S | | 121 (s/m1) |
| 3'- U³'^5'U | G A C C U G A A G G U C U U C U U G dU | -5' | J46-AS | Lamin exp27 | 122 (a/m2) |
| 3'- mU mU | G A C C U G A A G G U C U U C U U G dU | -5' | J23-AS | Lamin exp30 | 123 (a/m3) |
| 5'- mU mG | G G G U C A G C U C G U U A C dU dC dA mA | U³'^5'U -3' | J45-S | | 124 (s/m1) |
| 3'- mA mC | C C C A G U C G A G C A A U G A G U dU | -5' | J46-AS | 3CDC2 exp30 | 125 (a/m2) |
| 5'- mU mG | G G G A C A C C U C G U A A C dU dC dA mA | U³'^5'U -3' | J45-S | | 126 (s/m1) |
| 3'-mA mC | C C C U G U G G A G C A U U G A G U dU | -5' | J46-AS | 3CDC2 mut3 exp30 | 127 (a/m2) |
| 5'-mA mA | U G G C A C U G A A U C A U C dC dA dU mA | U³'^5'U -3' | J45-S | | 128 (s/m1) |
| 3'- U³'^5'U | A C C G U G A C U U A G U A G G U A dU | -5' | J46-AS | 1CDC2 exp27 | 129 (a/m2) |
| 3'- mU mU | A C C G U G A C U U A G U A G G U A dU | -5' | J23-AS | 1CDC2 exp30 | 130 (a/m3) |

*: SEQ ID: In this field, the number in front of the parenthesis indicates the SEQ ID NO as listed in field <210> of the sequence listing. The letters "s" or "a" indicate whether the strand is a sense strand (s) or the respective antisense strand (a). The letter "m" in combination with the respective number represents a consecutive numbering of the respective modification of this sense or antisense strand as outlined in field <223> of the sequence listing.

With the modified siRNA molecules (exp 1 to exp 95), tests were carried out to determine their ability to perform RNAinterference (RNAi). The ability of siRNA coupled with peptide sequences to induce silencing of the corresponding gene was tested compared to standard siRNA transfections using reagents based on the lipid technology. For this purpose LaminA/C, MAPK2/ERK2 (NM_002745.2), and CDC2 (NM_001786) genes were used as target to perform the silencing experiments. LaminA/C-, MAPK2(ERK2)-, and CDC2-siRNAs were modified and transfected to different cells lines. The silencing results were compared to silencing effects induced by the corresponding non-modified siRNAs. Further controls were non-treated cells and cells transfected with non-specific siRNA (GFP22).

Figure 1:
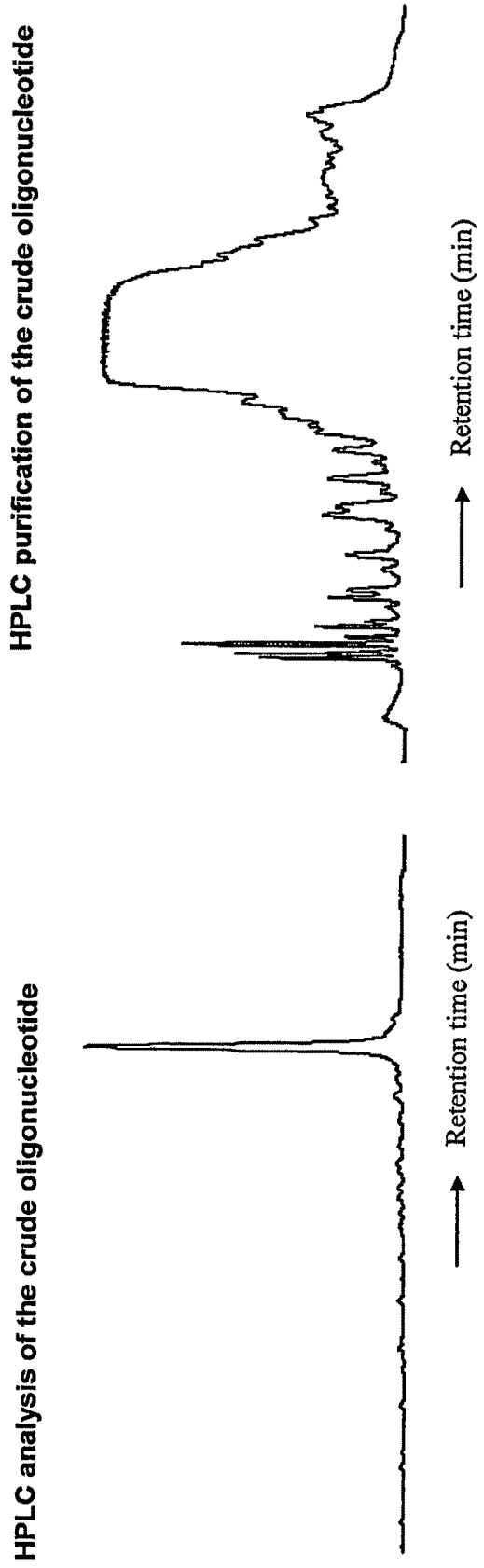
FIG. 1 shows the purification steps of an RNA oligonucleotide according to the present invention.
Figure 1:
Figure 2:
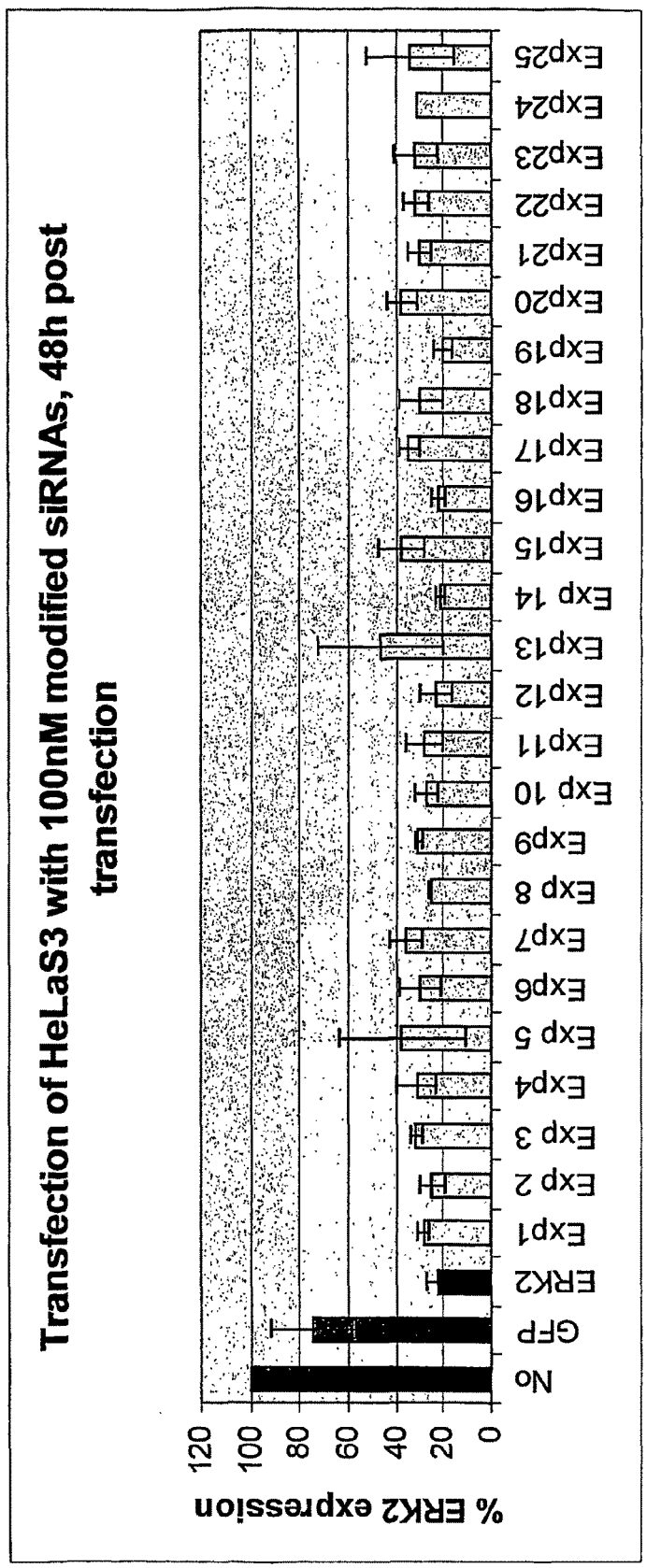
FIG. 2 shows the gene silencing efficiency in HeLAS3 cells transfected with 100 nM modified siRNAs according to the present invention (Examples 1 to 95), 48 h after the transfection.
Figure 2:
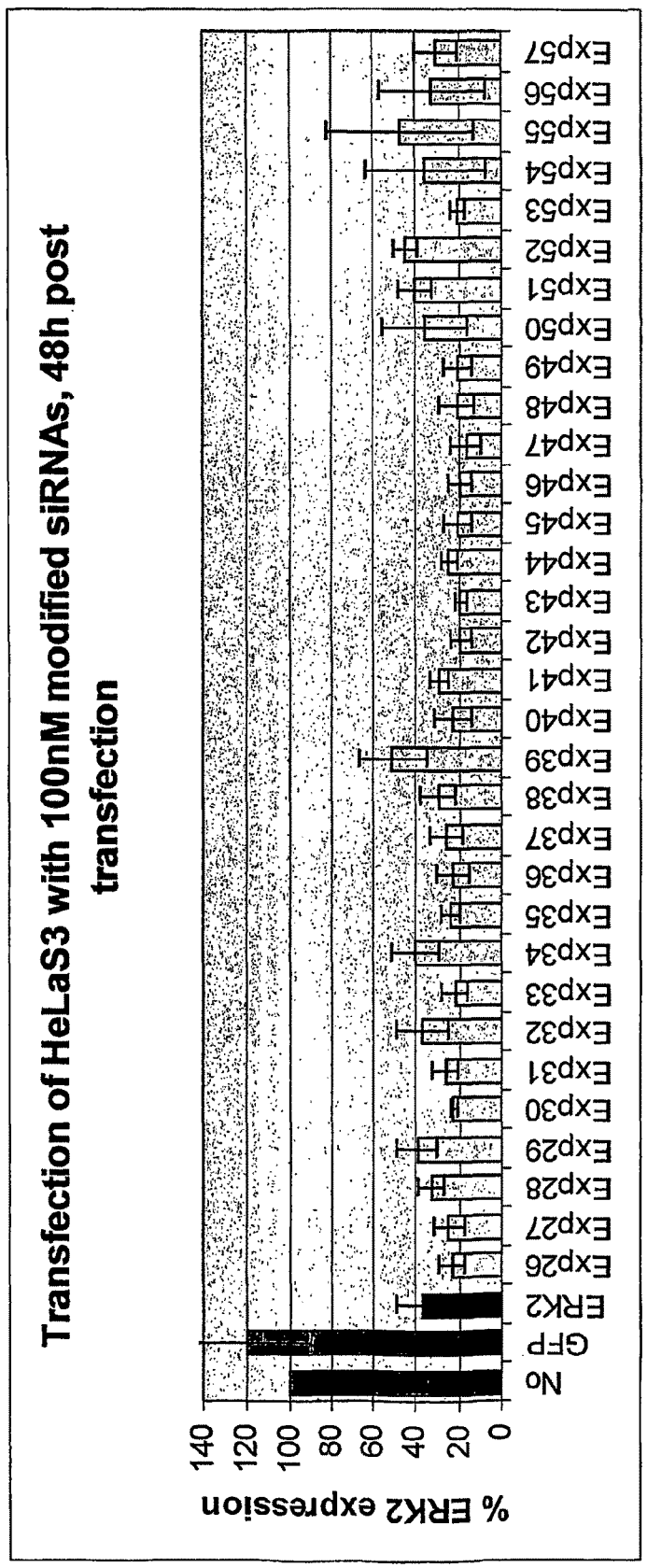
Figure 2:
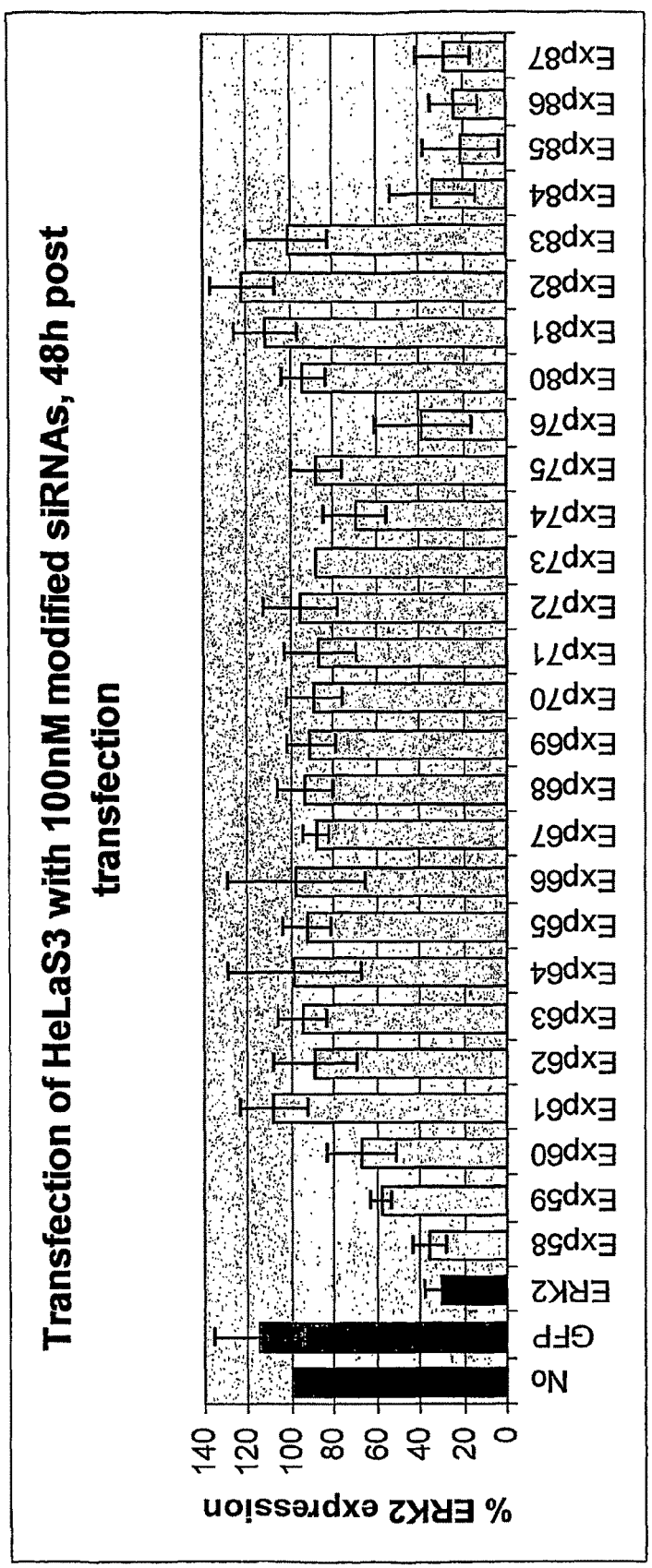
Figure 2:
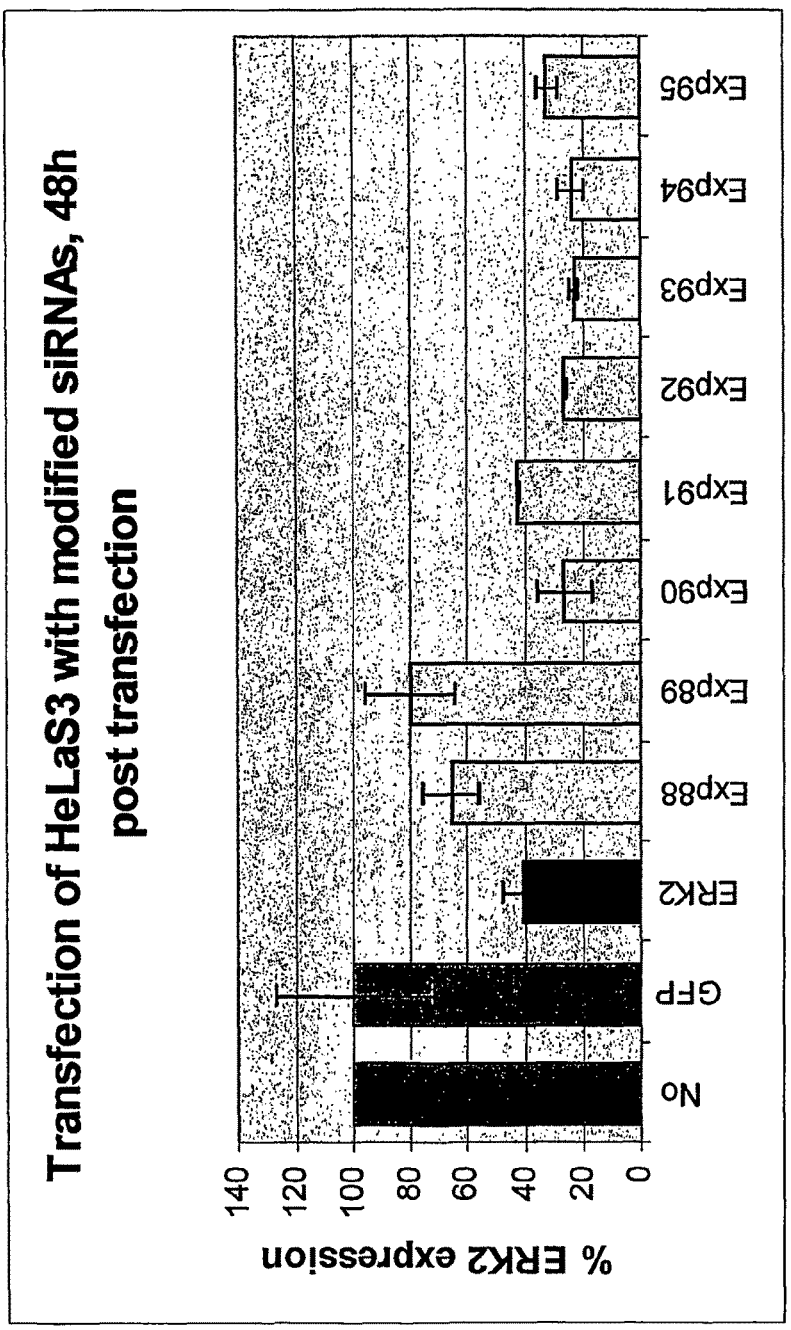

The following cell lines were used for the transfections: Human cervix carcinoma; HeLaS3, human breast carcinoma; MCF7, human glioblastoma; T98G, Human embryonic kidney; 293 cell-Line. FIG. 2 shows the transfection of HeLAS3 cells with 100 nM modified siRNAs 48 hours after transfection (RNAiFect® was used).

The culture conditions prior to transfection were as follows. 24 h before transfection cells were seeded in a density of 5-6×10⁴ cells/well. HeLaS3, T98G and 293 cell lines were incubated in standard DMEM complemented with 10% FCS (Fetal Calf Serum), at 37° C. and 5% $CO_2$ atmosphere. MCF7 cells were incubated in RPMI complemented with 10% FCS, insulin, glutamine and sodium pyruvate, otherwise under the same conditions as the other cell lines.

Transfection with RNAiFect® was carried out as follows (RNAiFect® is a trademark of QIAGEN GmbH, Hilden, Germany). 0.15-0.6 µg siRNA was diluted in complete medium to a final volume of 1001 and mixed by a Vortex mixer ("vortexing"). RNAiFect was added in a ratio of 1:6 (RNA (µg): Reagent (µl)) to the mixture, was mixed by vortexing and incubated for 15 min at room temperature. While complex formation was taking place, the medium was aspirated from the plate and 300 µl growth medium with serum was added onto the cells. After the complex formation was completed, the transfection complexes were added drop by drop onto the cells. The plate was swirled gently and cells were incubated for 48 h under normal growth conditions. No medium change was required.

Transfection with HiPerFect was carried out as follows (HiPerFect is a transfection reagent available from QIAGEN GmbH, Hilden, Germany). 0.375-37.5 ng siRNA (dependent on the transfected cell line) were diluted in 100 µl siRNA Dilution Buffer (100 mM potassium acetate, 30 mM HEPES-KOH, 2 mM Mg(OAc)$_2$, pH=7.4) and mixed by vortexing. 3 µl HiPerFect were added to the mixture, further mixed and incubated for 15 min at room temperature on a plate. While complex formation was taking place, the medium was aspirated from the plate and 500 µl growth medium with 10% serum was added onto the cells. After the complex formation was complete, the complex was added drop wise onto the cells. The plate was swirled gently and cells were incubated for 48 h or longer under normal growth conditions (37° C., 5% $CO_2$).

The modifications to the siRNA molecules were also monitored for possible toxic effects on the cells. The cell toxicity test was carried out as follows. The Roche LDH cytotoxicity detection kit was used for this purpose. The culture supernatants were collected before cell lysis and lactate dehydrogenase (LDH) was measured. The amount of LDH activity released from the cytosol of damaged cells into the supernatant was used to monitor cell toxicity.

In addition, the transfection efficiency was analyzed. 48 h after the transfection the medium was aspirated from the plates, the cells were lysed in 350 µl RLT buffer and the total RNA was prepared using RNeasy 96 plate and RNeasy 96 protocol ("RNeasy 96" are products available from QIAGEN GmbH, Hilden, Germany).

2 µl RNA were amplified in a one tube RT-PCR using TaqMan Primer and Probes ("TaqMan Probe®" is a trademark of Applied Biosystems; Foster City, Calif., USA). Amplification was performed in parallel for the target gene and GAPDH. Target expression was analyzed as quotient of the GAPDH expression. The absolute target expression of the treated cells using modified siRNA was compared to the absolute target expression of the treated cells using standard (i.e. non-modified) siRNA. The targets used were LaminA/C, MAPK2 and CDC2.

Primers and Probes used in QuantiTect Duplex RT-PCR analysis ("QuantiTect" is an assay for gene expression analysis using quantitative, real-time RT-PCR available from QIAGEN GmbH, Hilden; Germany; "F" and "For" denotes "Forward", "R" and "Rev" denotes "Reverse"):

|  | Sequence |
|---|---|
| Primers |  |
| LaminA_776F | GGC GGG TGG ATG CTG AGA ACA (SEQ ID NO: 6) |
| LaminA_881R | TGT CAA TCT CCA CCA GTC GGG (SEQ ID NO: 7) |
| MAPK2_F | CCT TCC AAC CTG CTG CTC AAC AC (SEQ ID NO: 8) |
| MAPK2_R | GCC ACA TAT TCT GTC AGG AAC CC (SEQ ID NO: 9) |
| CDC2_F | AAT AAG CCG GGG ATC TAC CAT AC (SEQ ID NO: 10) |
| CDC2_R | TTT CAT GGC TAC CAC TTG ACC TG (SEQ ID NO: 11) |
| hGAPDH-TM-For | GAA GGT GAA GGT CGG AGT (SEQ ID NO: 12) |
| hGAPDH-TM-Rev | GAA GAT GGT GAT GGG ATT TC (SEQ ID NO: 13) |
| TaqMan Probes: |  |
| LaminA_838TM | 5'-FAM-ATCTACAGTGAGGAGCTGCGTGAGA-3'-BHQ (SEQ ID NO: 14) |
| MAPK2_TM | 5'-FAM-TGGCCCGTGTTGCAGATCCAGAC-3'-BHQ (SEQ ID NO: 15) |
| CDC2_TM | 5'-FAM-ATGGAGTTGTGTATAAGGGTAGAC-3'-BHQ (SEQ ID NO: 16) |
| hGAPDH-TM | 5 -HEX-CAAGCTTCCCGTTCTCAGCCT-3'-BHQ (SEQ ID NO: 17) |

(BHQ = Black Hole Quencher; FAM and HEX = Fluorophores; oligonucleotides are synthesised and modified with fluorophores by Operon)

As a next step the gene silencing efficiency of the siRNA molecules according to the present invention were tested. For this purpose, a screening of modified siRNAs was carried out. FIG. 2 shows the result of this screening experiment. In FIG. 2, the MAPK2 (ERK2) expression in HeLaS3 cells is shown. The "No" bar in FIG. 2 represents untreated cells. "GFP" and "ERK2" represent control transfections with nonspecific siRNA and non modified siRNA, respectively. Exp 1-95 represent the residual MAPK2 expression in cells transfected with different modified MAPK2-siRNAs (the type of the modification can be seen from Table 1). Each of the bars for Exp. 1 to Exp. 95 represents the mean value of four measurements. The line indicated at the top of each bar represents the standard deviation for each of Exp. 1 to 95. The cells were tested also for cytotoxicity. None of the tested siRNAs was found to be cytotoxic.

As can be seen from FIG. 2, the residual MAPK2 expression in HeLaS3 cells transfected with the different modified MAPK2-siRNAs according to Exp. 27, 30, 33, 35, 43, and 53 (see Table 1 for exact structures) show a convincing gene silencing effect. Taking furthermore into account the stability of the respective siRNAs against nuclease attack, Exp. 27, 30, 33, 35, 43, and 53 have shown the best performance of the modified siRNAs tested.

It can be seen from the above that siRNAs with end modifications do not negatively affect the gene silencing mechanism. Depending on the amount and type of modifications, siRNAs are obtained that enhance the siRNA activity. The screening was performed also with 25 nM siRNA to visualize and specify slight differences between the modified siRNAs (data not shown). The data with 25 nM siRNA confirmed the data obtained with 100 nM. In the following, the best performing siRNAs were used to test sensitivity and longevity of siRNA.

Figure 3:
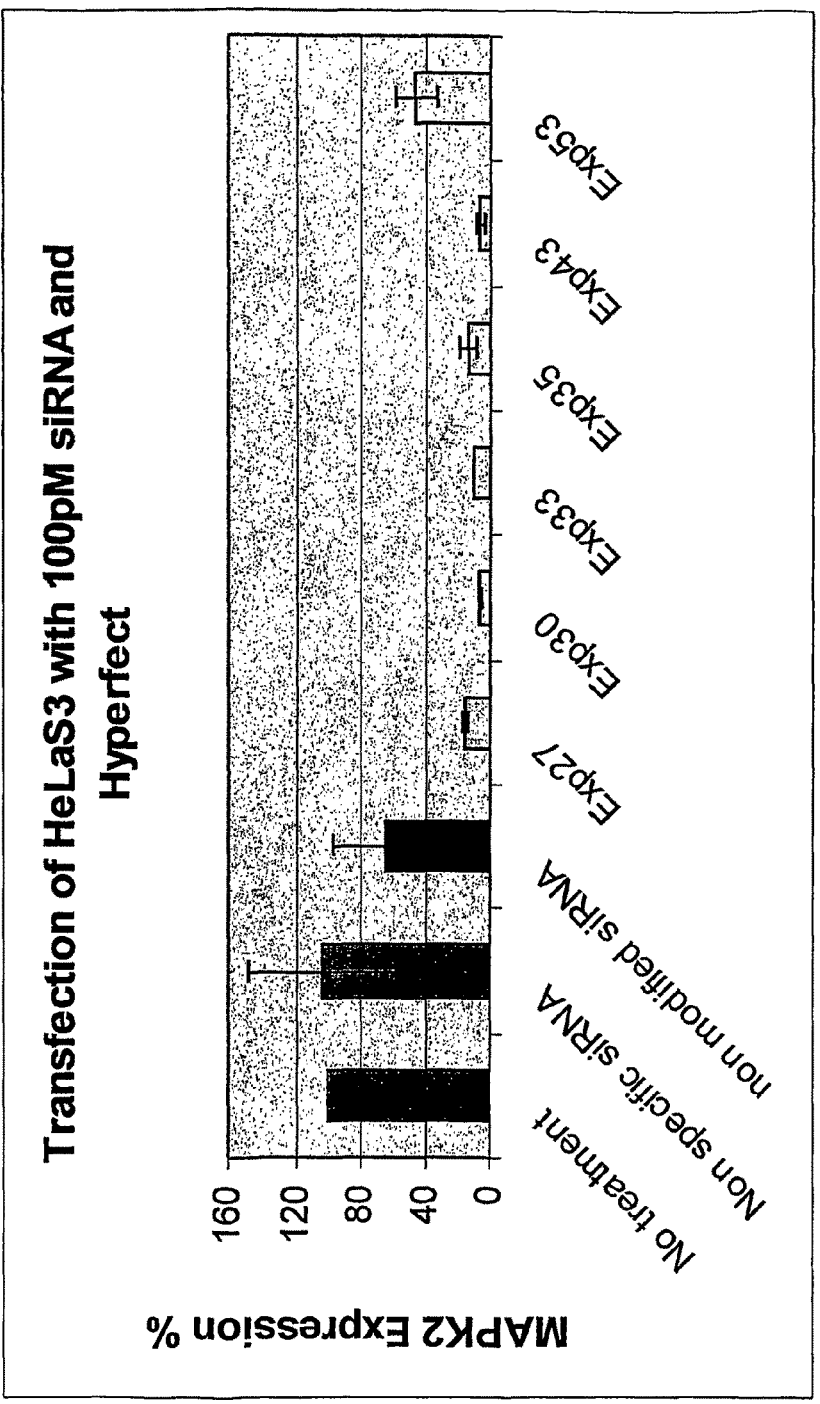
FIG. 3 shows the gene silencing efficiency in HeLAS3 cells transfected with 100 pM modified siRNAs according to the present invention (Examples 27, 30, 33, 35, 43, and 53), with HiPerFect being used as a transfection reagent.

FIG. 3 shows the results of experiments in which transfection of HeLAS3 cells with MAPK2-siRNAs in the HiPerFect transfection system was carried out with lower siRNA concentrations than for the experiments shown in FIG. 2 (100 pM in FIG. 3 compared to 100 nM in FIG. 2). As can be seen, the difference in performance (gene silencing) between modified and non-modified siRNA is becoming greater at very low siRNA concentrations (100 pM). The modified siRNA according to the present invention induces high gene silencing levels even at concentrations in the pmolar range.

Figure 4:
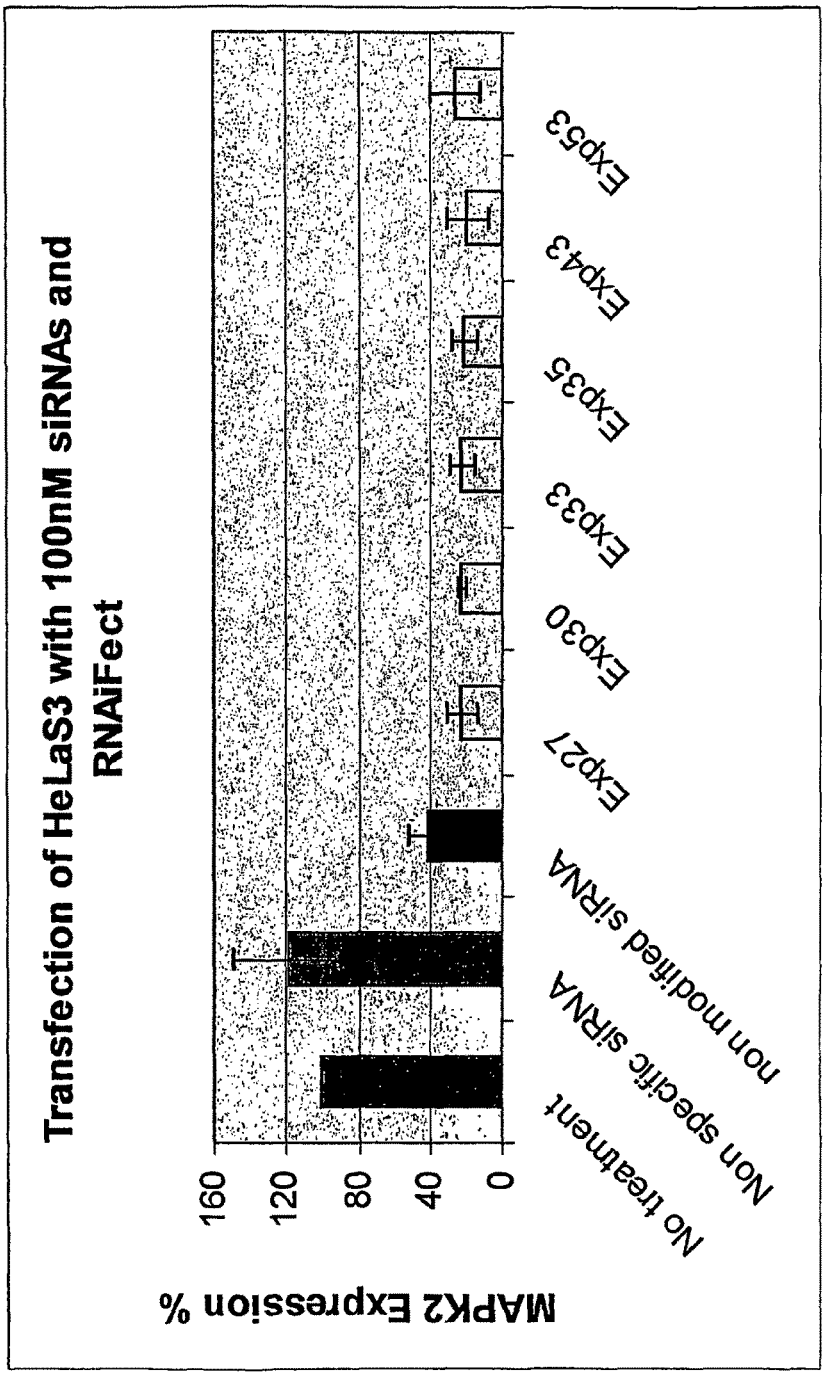
FIG. 4 shows the gene silencing efficiency in different cell types (HeLaS3, MCF7, and T98G) transfected with different amounts of modified siRNA according to the present invention (100 nM, 25 nM, 10 nM, 5 nM)
Figure 4:
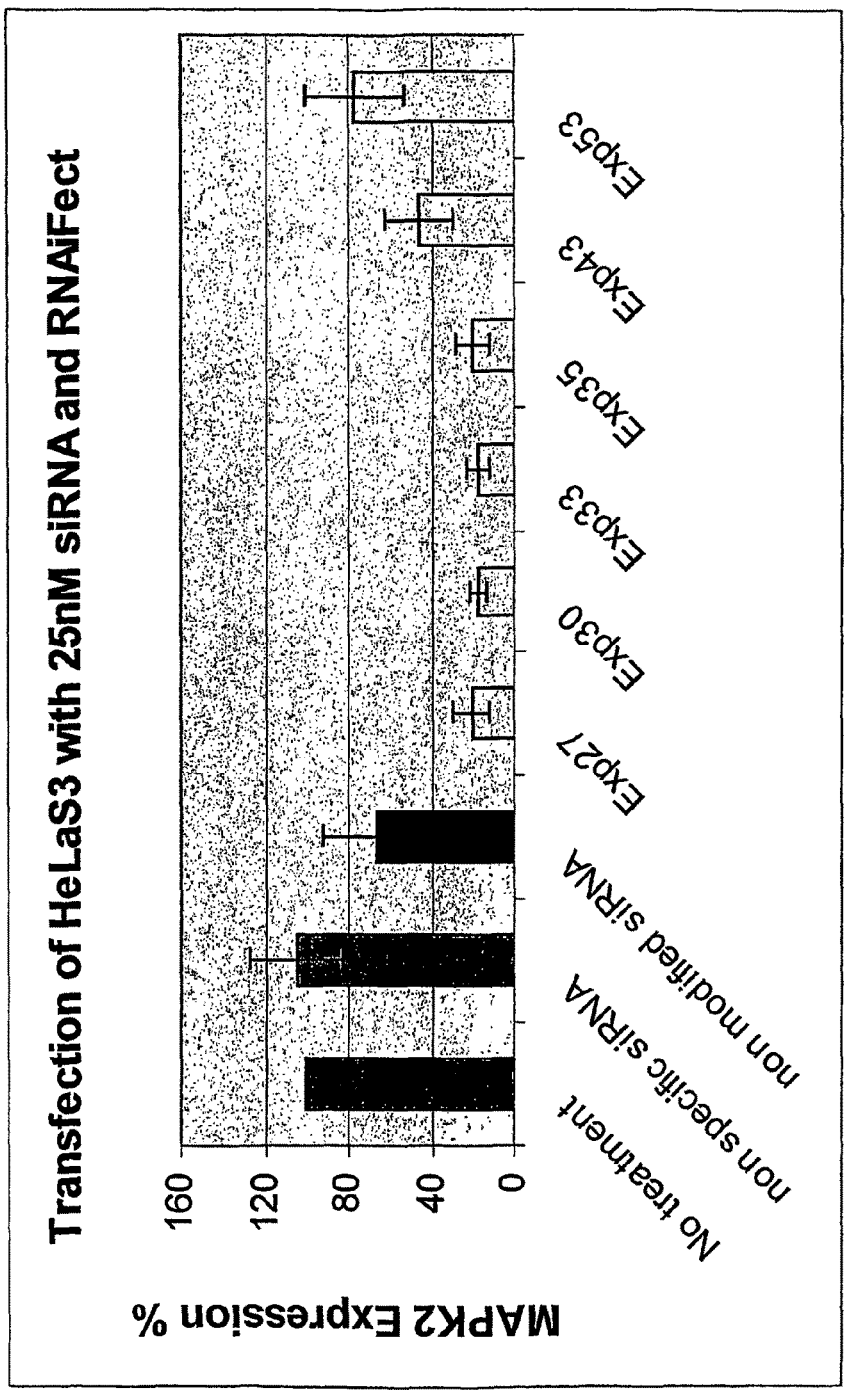
Figure 4:
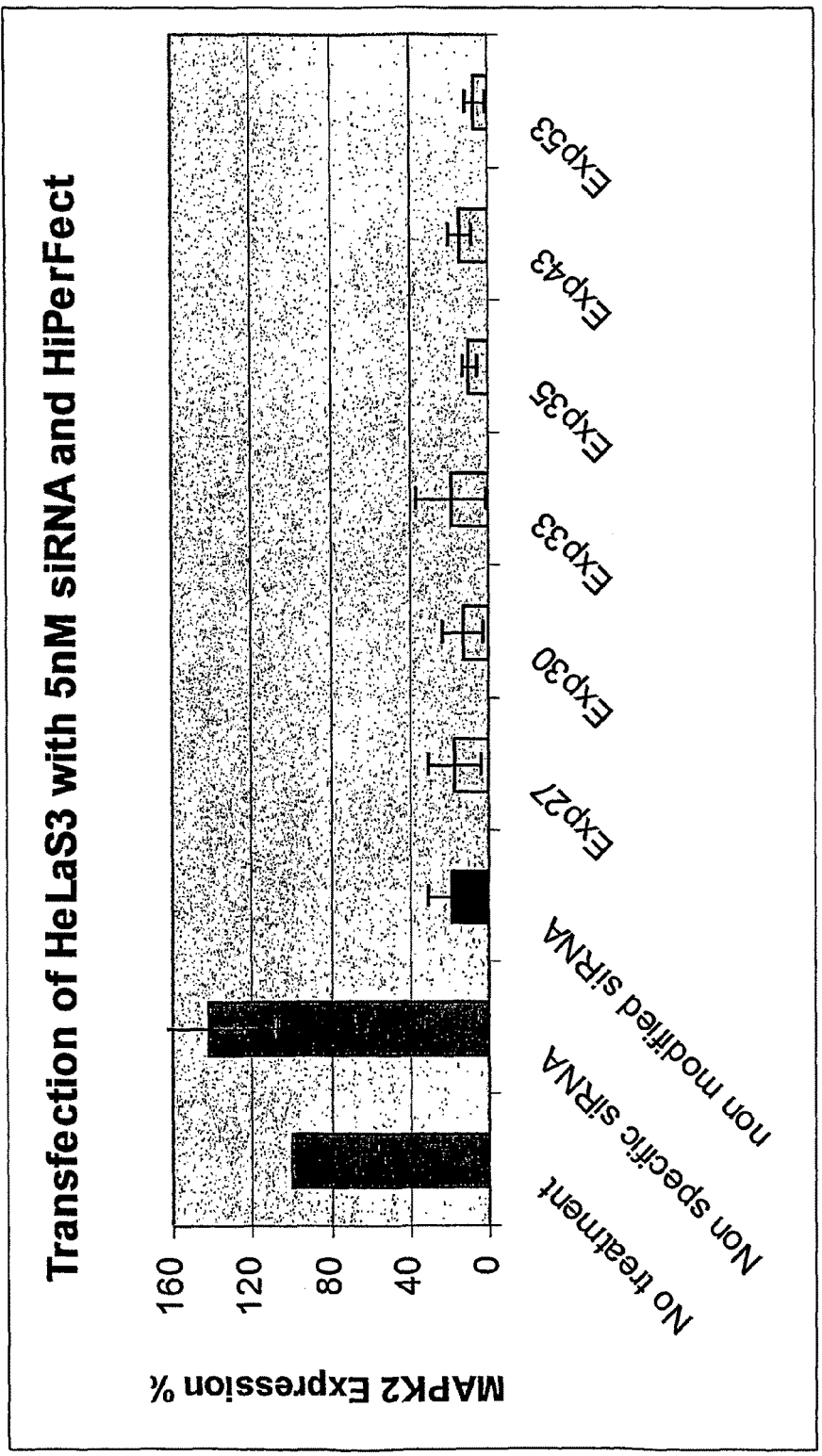
Figure 4:
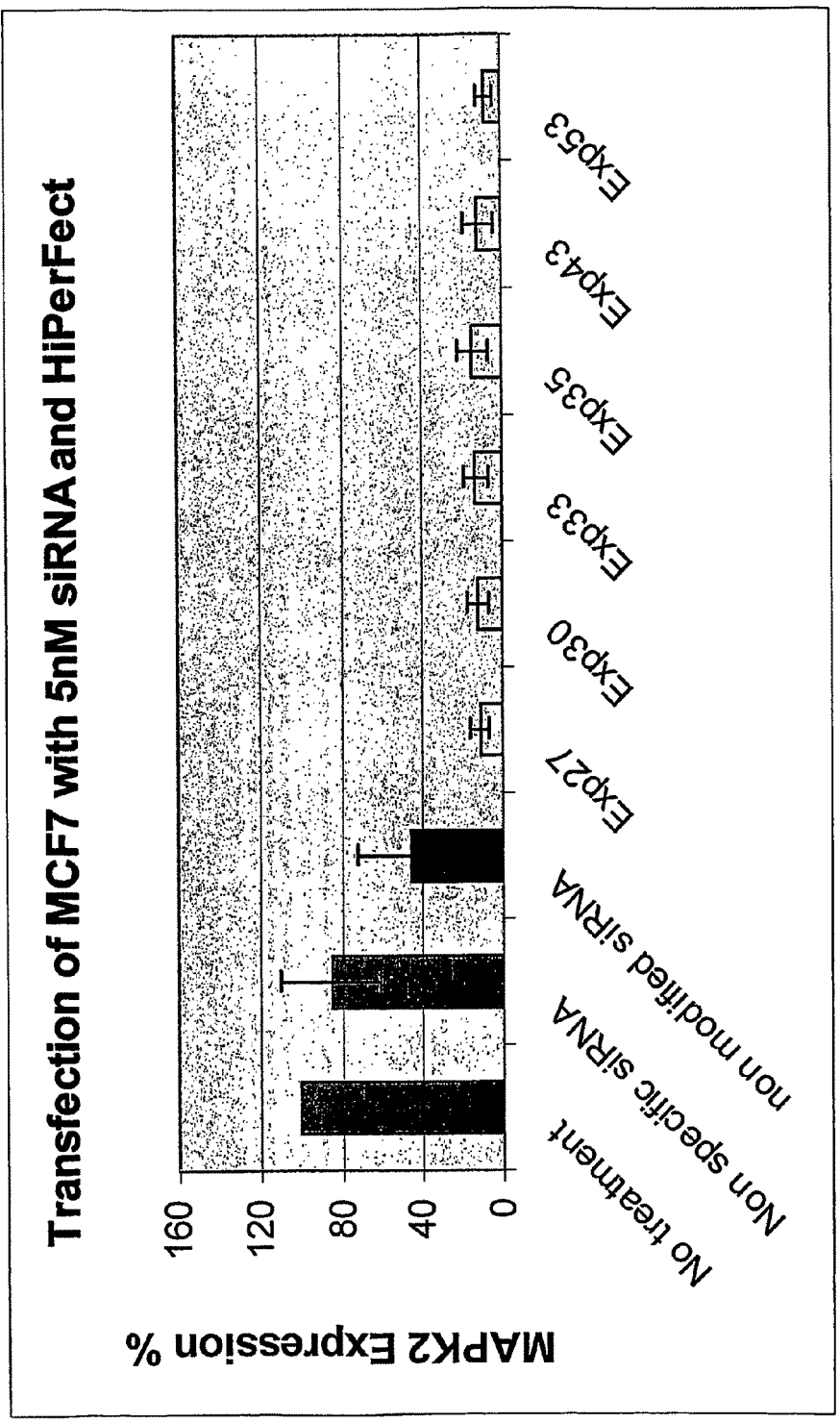
Figure 4:
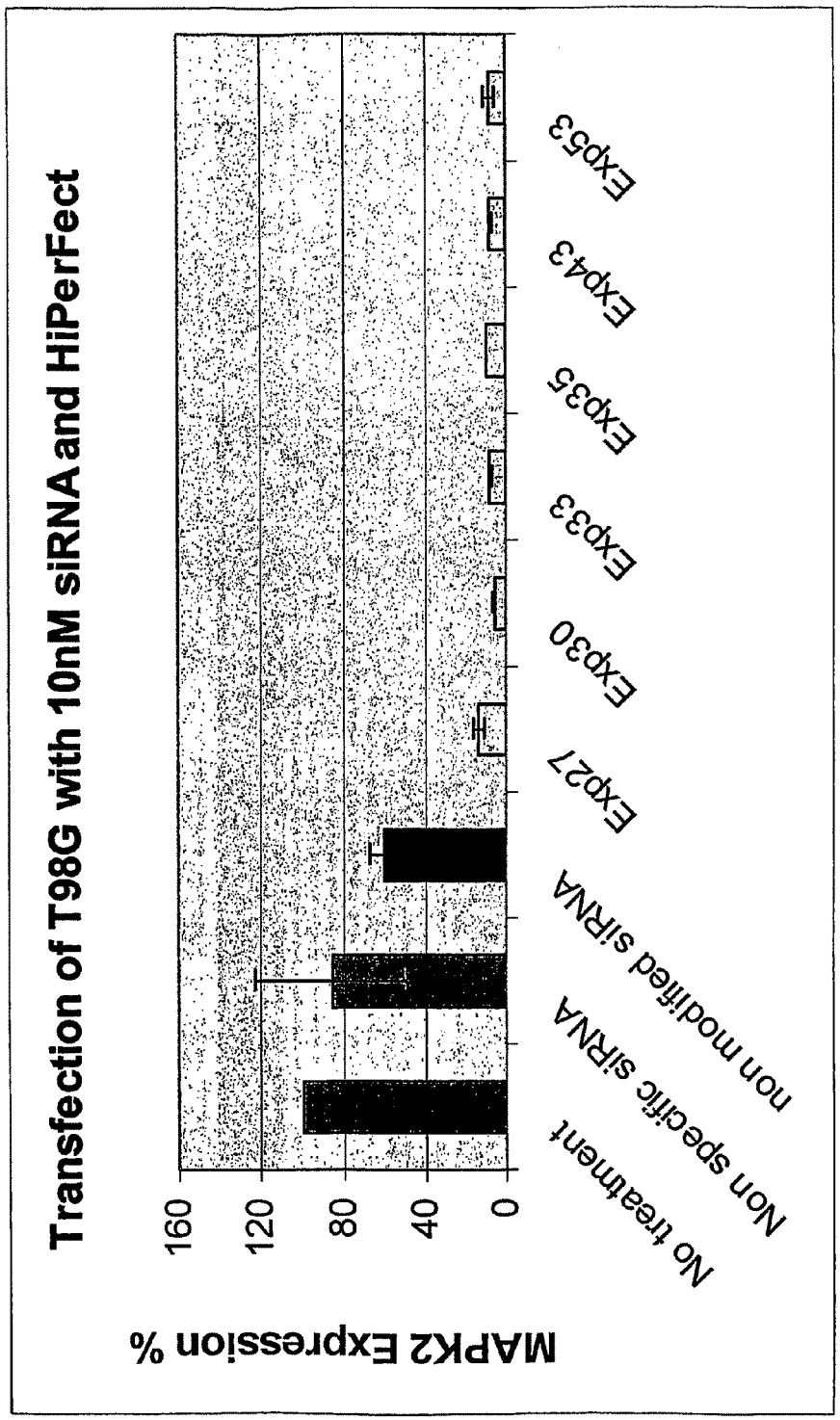

In addition, the gene silencing efficiency (potency/sensitivity) of the siRNA according to the present invention has been investigated. Different cell lines were transfected using RNAiFect or HiPerFect and different siRNA amounts. Very low amounts of siRNA were used to estimate the siRNA sensitivity. Specifically, the gene silencing efficiency of the best performing modified siRNAs (Exp. 27, 30, 33, 35, 43, and 53) has been tested further. FIG. 4 represents the MAPK2 expression in HeLaS3, MCF7, and T98G cells 48 h after transfection with different concentrations of modified and non modified siRNAs using RNAiFect or HiPerFect. The amount of siRNA, which was sufficient to induce silencing, and which was used for the transfections was estimated for each of the cell lines HeLaS3, MCF7, and T98G.

In FIG. 4, the "no treatment" bar represents untreated cells. "Non specific siRNA" and "non modified siRNA" represent control transfections with nonspecific siRNA and non modified siRNA, respectively. Exp. 27, Exp. 30, Exp. 33, Exp. 35, Exp. 43, and Exp. 53 represent the remaining MAPK2 expression in cells transfected with different modified MAPK2-siRNAs. The modified siRNA shown on these graphs (Exp. 27, 30, 33, 35, 43, and 53) are those, which have shown the best performance in terms of gene silencing and stability against nucleases. From the results shown in FIG. 4 it can be concluded that the chosen modified siRNAs (Exp. 27, 30, 33, 35, 43, and 53) perform better than non modified, regardless of transfection reagent or cell line. Again it can be seen that the difference in performance between modified and non modified siRNA is getting greater at very low siRNA concentrations. Modified siRNA induce high silencing levels even with concentrations in the pmolar range.

This is also evident from the test results shown in FIG. 3. This FIG. 3 refers to HeLaS3 cells transfected with MAPK2-siRNA using the HiPerFect transfection support system. As can be seen from FIG. 5, the modified siRNA according to the present invention (Exp. 27, Exp. 30, Exp. 33, Exp. 35, Exp. 43, and Exp. 53) are very effective in an amount of 100 pM only compared to a respective amount of unmodified MAPK2 specific siRNA. E.g., Exp. 30 and Exp. 43 were more than 10 times more effective than the respective non-modified siRNA.

Figure 5:
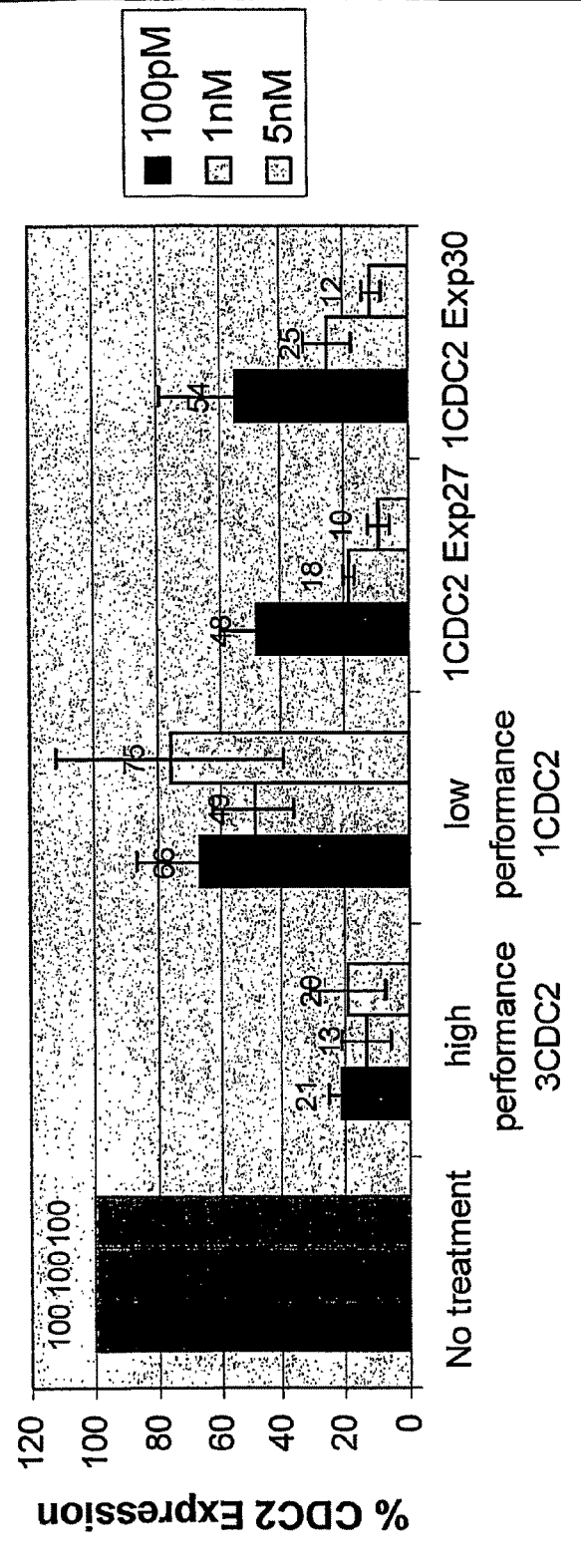
FIG. 5 shows the gene silencing efficiency of low performance siRNA compared to modified siRNA according to the present invention (Examples 27 and 30) at different concentrations (100 pM, 1 nM, 5 nM)

FIG. 5 shows that an siRNA modified according to the present invention can change a non-potent siRNA into a potent one at reasonable concentrations between 100 pM and 5 nM. The gene expression can be down-regulated with the modified siRNAs according to the present invention to about 10% of the value obtained with non-treated siRNAs (10% for 5 nM of the siRNA modified according to Example 27 and 12% for 5 nM of the siRNA modified according to Example 30).

As a next step, the gene silencing efficiency of the inventive siRNA has been tested in view of the siRNA longevity. The duration of the silencing effects of the best performing modified siRNAs (Exp. 27, 30, 33, 35, 43, and 53) were tested in HeLaS3 and T98G cells. HeLaS3 cells were transfected with RNAiFect and 100 nM MAPK2-siRNA and HiPerFect and 10 nM MAPK2-siRNA, respectively. MAPK2-down-regulation was measured 2 and 6 days after transfection. The modified siRNAs, which were used to induce long term silencing, are compared to non-modified siRNA. The results are shown in FIG. 6. As can easily be seen from these results, siRNAs modified in accordance with the present invention perform better in terms of efficiency and longevity independent of the transfection system used.

Furthermore, the gene silencing efficiency of the inventive siRNAs have been tested using different targets. FIG. 7 represents gene silencing of Lamin A/C and CDC2 in HeLaS3 cells. LaminA/C- and CDC2-siRNA were modified using the best performing modifications (Exp. 27, Exp. 30). Again "No treatment" bars represent untreated, normal growing cells. "Non specific" and "non modified" represent control transfections with nonspecific siRNA and non modified siRNA, respectively. Exp. 27 and Exp. 30 represent the remaining Lamin/AC or CDC2 expression in cells, which were transfected with the corresponding modified siRNA. The conclusion that can be drawn from the results in FIG. 7 is that the modifications used improved the gene silencing performance of active siRNAs and slightly enhanced the siRNA efficiency of moderate active siRNAs. Mutated-negative control siRNA still remains inactive, a false activity due to modifications is excluded.

Furthermore, the stability of the siRNA according to the present invention in cell culture medium has been tested. For this purpose, the stability in 10% Fetal Calf Serum (FCS) has been determined by HPLC. In the following Table 3, the amount of siRNA remaining after t=4 h, 24 h, 48 h, and 72 h in percent is given (t=0 h is 100%).

TABLE 3

| Example | 4 h | 24 h | 48 h | 72 h |
| --- | --- | --- | --- | --- |
| Exp. 26 | 95 | 90 | | |
| Exp. 27 | 95 | 90 | | |
| Exp. 28 | 90 | 70 | | |
| Exp. 34 | 95 | 90 | | |

TABLE 3-continued

| Example | 4 h | 24 h | 48 h | 72 h |
|---------|-----|------|------|------|
| Exp. 35 | 70  |      |      |      |
| Exp. 36 | 70  |      |      |      |
| Exp. 42 | 70  |      |      |      |
| Exp. 58 | 100 | 95   | 90   | 85   |
| Exp. 59 | 95  | 90   | 65   | 60   |
| Exp. 60 | 95  | 90   | 65   | 60   |
| Exp. 61 | 100 | 95   | 80   | 75   |
| Exp. 63 | 95  | 55   | 35   |      |
| Exp. 64 | 100 | 95   | 80   | 75   |
| Exp. 66 | 95  | 55   | 65   |      |
| Exp. 69 | 90  | 55   | 35   |      |
| Exp. 72 | 95  | 55   | 35   |      |
| Exp. 73 | 100 | 98   | 90   | 90   |
| Exp. 74 | 100 | 98   | 98   | 97   |

From the results shown in Table 3 above as well as the data given in FIGS. 8 and 9, it can be seen that the modifications of the siRNA used dramatically enhance the siRNA stability in cell culture media (containing 10% serum). FIG. 8 shows an HPLC analysis of traces of the modified siRNA (Exp. 58) in cell culture medium with 10% serum after 4 h, 24 h, 36 h, 48 h, and 72 h (=3 d). From FIG. 9, the stability of siRNA in cell culture medium before and after complexing with transfection reagent is shown (modified according to Exp. 28; transfection reagent RNAifect®, trademark of the QIAGEN GmbH, Hilden, Germany; "w/" with transfection agent, "w/o" without transfection agent). Complexing with transfection reagents slightly prevents siRNA degradation, but still a high an unacceptable amount of unmodified siRNA is cleaved by serum nucleases (FIG. 10, unmodified MAPK2 w/RNAifect). The modifications according to the present invention assure almost full length siRNAs even after three days incubation in cell culture media (see FIGS. 8 and 9), thereby preventing off-target effects due to shortened (and therefore more unspecific) siRNA.

Finally, the stability of the siRNAs according to the present invention in 100% human serum has been tested. Specifically, siRNAs with different sequences were tested for their stability in pure human serum. Examples of siRNAs with modifications according to Exp. 30, Exp. 27, Exp. 84, Exp. 90 and Exp. 94 were compared with non modified siRNA. The results are shown in FIG. 10. It can be seen from the FIG. 10 that the stability of siRNA is strongly depended on the sequence of the tested siRNA. A defined cleavage has been obtained after incubation in 100% human serum. This cleavage has been dramatically slowed down due to the chemical modifications according to the present invention. After 24 h of incubation, full length modified siRNA is still present, while non-modified siRNA is being completely degraded within minutes.

Screening of Additional Modified siRNAs

Additional chemical modifications were tested for their effects in the performance of the siRNA in terms of siRNA potency, longevity and stability. The sequences and modifications are listed in the following table.

Additional Tested Modifications
siRNA Duplexes (Top Row of Each Paragraph: Sense-Strand, Followed by Antisense Strands)
Legend: dA, dC, dG, dT, dU: 2'-deoxy-modified nucleotides
mA, mC, mG, mT, ml): 2"-methoxy-modified nucleotides
$U^{3'\wedge 5'}$ U 3' to 5' formacetal linkage
$U^{2'\wedge 5'}$ U: 2' to 5' formacetal linkage
Ac2, Cc2, Gc2, Tc2, Uc2: 2'-acetal-modified nucleotides
Ac2n, Cc2n, Gc2n, Tc2n, Uc2n: 2'-acetal-amine-modified nucleotides

| overhang | core sequence (SEQ ID NOS 131-194, respectively, in order of appearance) | | | | | | | | | | | | | | | | | overhang | strand name | siRNA duplex name |
|---|---|---|---|---|---|---|---|---|---|---|---|---|---|---|---|---|---|---|---|---|
| 5'-<br>mA mA | U | G | G | U | G | A | C | U | C | C | A | A | A | G | C | dT | dC dT mG | $U^{2'\wedge 5'}U$ -3' | J51-S | (MAPK2) |
| 3'-<br>$U^{2'\wedge 5'}U$ | A | C | G | A | C | U | G | A | G | G | U | U | U | C | G | A | G | A dC -5' | J50-AS | exp 96 |
| 5'-<br>Ac2 Ac2 | U | G | C | U | G | A | C | U | C | C | A | A | A | G | C | Uc2 | Cc2 Uc2 Gc2 | $U^{3'\wedge 5'}U$ -3' | J52-AS | |
| 3'-<br>$U^{3'\wedge 5'}U$ | A | C | G | A | C | U | G | A | G | G | U | U | U | C | G | A | G | A C -5' | J8-AS | exp 97 |
| 3'-<br>$U^{3'\wedge 5'}U$ | A | C | G | A | C | U | G | A | G | G | U | U | U | C | G | A | G | A dC -5' | J23-AS | exp 101 |
| 3'-<br>mU Uc2 | A | C | G | A | C | U | G | A | G | G | U | U | U | C | G | A | G | A dC -5' | J63-AS | exp 107 |
| 3'-<br>Uc2 Uc2 | A | C | G | A | C | U | G | A | G | G | U | U | U | C | G | A | G | A dC -5' | J64-AS | exp 108 |
| 3'-<br>$U^{2'\wedge 5'}U$ | A | C | G | A | C | U | G | A | G | G | U | U | U | C | G | A | G | A dC -5' | J50-AS | exp 113 |
| 5'-<br>Ac2 Ac2 | U | G | C | U | G | A | C | U | C | C | A | A | A | G | C | Uc2 | Cc2 Uc2 Gc2 | $U^{2'\wedge 5'}U$ -3' | J53-S | |
| 3'-<br>$U^{2'\wedge 5'}U$ | A | C | G | A | C | U | G | A | G | G | U | U | U | C | G | A | G | A C -5' | J7-AS | exp 98 |
| 3'-<br>$U^{2'\wedge 5'}U$ | A | C | G | A | C | U | G | A | G | G | U | U | U | G | G | A | G | A dC -5' | J50-AS | exp 102 |
| 3'-<br>mU Uc2 | A | C | G | A | C | U | G | A | G | G | U | U | U | C | G | A | G | A dC -5' | J63-AS | exp 109 |

-continued

| overhang | core sequence (SEQ ID NOS 131-194, respectively, in order of appearance) | overhang | strand name | siRNA duplex name |
|---|---|---|---|---|
| 3'- Uc2 Uc2 | A C G A C U G A G G U U U C G A G A dC | -5' | J64-AS | exp 110 |
| 5'- Dc2 Dc2 | U G C U G A C U C C A A A G C Uc2 Cc2 Uc2 Gc2 U$^{3'\wedge 5'}$U | -3' | J54-S | |
| 3'- U$^{3'\wedge 5'}$U | A C G A C U G A G G U U U C G A G A C | -5' | J8-AS | exp 99 |
| 3'- U$^{3'\wedge 5'}$U | A C G A C U G A G G U U U C G A G A dC | -5' | J23-AS | exp 103 |
| 3'- U$^{2'\wedge 5'}$U | A C G A C U G A G G U U U C G A G A dC | -5' | J50-A5 | exp 114 |
| 5'- Dc2 Dc2 | U G C U G A C U C C A A A G C Uc2 Cc2 Uc2 Gc2 U$^{2'\wedge 5'}$U | -3' | J55-S | |
| 3'- U$^{2'\wedge 5'}$U | A C G A C U G A G G U U U C G A G A C | -5' | J7-AS | exp 100 |
| 3'- U$^{2'\wedge 5'}$U | A C G A C U G A G G U U U C G A G A dC | -5' | J50-AS | exp 104 |
| 3'- mU Uc2 | A C G A C U G A G G U U U C G A G A dC | -5' | J63-AS | exp 111 |
| 3'- Uc2 Uc2 | A C G A C U G A G G U U U C G A G A dC | -5' | J64-AS | exp 112 |
| 5'- | dT G C U G A C U C C A A A G C U C U G U$^{2'\wedge 5'}$U | -3' | J75-S | |
| 3'- U$^{2'\wedge 5'}$U | Ac2 Cc2 Gc2 Ac2 C U G A G G U U U C G A G A C Ac2 Ac2 | -5' | J70-AS | exp 102 neg |
| 5'- | dT G C U G A C U C C A A A G C U C U G U$^{2'\wedge 5'}$U | -3' | J75-S | |
| 3'- U$^{2'\wedge 5'}$U | Ac2 Cc2 Gc2 Ac2 C U G A G G U U U C G A G A C Dc2 Dc2 | -5' | J71-AS | exp 104 neg |
| 5'- Ac2 Ac2 | U G C U G A C U C C A A A Gc2 Cc2 Uc2 Cc2 Uc2 Gc2 U$^{2'\wedge 5'}$U | -3' | J53-S + 2c2 | |
| 3'- U$^{2'\wedge 5'}$U | A C G A C U G A G G U U U C G A G A dC | -5' | J50-AS | exp 115 |
| 5'- Ac2 Ac2 | U G C U G A C U C C A Ac2 Ac2 Gc2 Cc2 Uc2 Cc2 Uc2 Gc2 U$^{2'\wedge 5'}$U | -3' | J53-S + 4c2 | |
| 3'- U$^{2'\wedge 5'}$U | A C G A C U G A G G U U U C G A G A dC | -5' | J50-AS | exp 116 |
| 5'- Ac2 Ac2 | U G C U G A C U C C A A A G C Uc2 Cc2 Uc2 Gc2n U$^{2'\wedge 5'}$U | -3' | J88-S | |
| 3'- U$^{2'\wedge 5'}$U | A C G A C U G A G G U U U C G A G A dC | -5' | J50-AS | exp 117 |
| 5'- Ac2 Ac2 | U G C U G A C U C C A A A G C Uc2 Cc2 Uc2 Gc2n U$^{2'\wedge 5'}$U | -3' | J89-S | |
| 3'- U$^{2'\wedge 5'}$U | A C G A C U G A G G U U U C G A G A dC | -5' | J50-AS | exp 118 |
| 5'- Ac2n Ac2 | U G C U G A C U C C A A A G C Uc2 Cc2 Uc2 Gc2 U$^{2'\wedge 5'}$U | -3' | J90-S | |
| 3'- U$^{2'\wedge 5'}$U | A C G A C U G A G G U U U C G A G A dC | -5' | J50-AS | exp 119 |
| 5'- Ac2 Ac2 | U G C U G A C U C C A A A G C Uc2 Cc2 Uc2 Gc2 U$^{2'\wedge 5'}$U | -3' | J53-S | |

| overhang | core sequence (SEQ ID NOS 131-194, respectively, in order of appearance) | | | | | | | | | | | | | | | | overhang | strand name | siRNA duplex name |
|---|---|---|---|---|---|---|---|---|---|---|---|---|---|---|---|---|---|---|---|
| 3'-U$^{2'\wedge5'}$U | A | C | G | A | C | U | G | A | G | G | U | U | U | C | G | A | G | A Cc2n | -5' | J91-AS | exp 120 |
| 5'-Ac2 Ac2 | U | G | C | U | G | A | C | U | C | C | A | A | A | G | C | Uc2 Cc2 Uc2 Gc2 U$^{2'\wedge5'}$U | -3' | J53-S | |
| 3'-U$^{2'\wedge5'}$U | Ac2n | C | G | A | C | U | G | A | G | G | U | U | U | C | G | A | G | A dC | -5' | J91-AS | exp 121 |
| 5'-Ac2 Ac2 | C | U | G | G | A | C | U | U | C | C | A | G | A | A | G | Ac2 Ac2 Cc2 Ac2 U$^{3'\wedge5'}$U | -3' | J58-S | (Lamin) |
| 3'-U$^{3'\wedge5'}$U | G | A | C | C | U | G | A | A | G | G | U | C | U | U | C | U | U | G dU | -5' | J46-AS | Lamin (Lamin) exp 101 |
| 5'-Ac2 Ac2 | C | U | G | G | A | C | U | U | C | C | A | G | A | A | G | Ac2 Ac2 Cc2 Ac2 U$^{2'\wedge5'}$U | -3' | J65-S | |
| 3'-U$^{2'\wedge5'}$U | G | A | C | C | U | G | A | A | G | G | U | C | U | U | C | U | U | G dU | -5' | J72-AS | Lamin exp 102 |
| 5'-Dc2 Dc2 | C | U | G | G | A | C | U | U | C | C | A | G | A | A | G | Ac2 Ac2 Cc2 Ac2 U$^{3'\wedge5'}$U | -3' | J59-S | |
| 3'-U$^{3'\wedge5'}$U | G | A | C | C | U | G | A | A | G | G | U | C | U | U | C | U | U | G dU | -5' | J48-AS | Lamin (Lamin) exp 103 |
| 5'-Dc2 Dc2 | C | U | G | G | A | C | U | U | C | C | A | G | A | A | G | Ac2 Ac2 Cc2 Ac2 U$^{2'\wedge5'}$U | -3' | J66-S | |
| 3'-U$^{2'\wedge5'}$U | G | A | C | C | U | G | A | A | G | G | U | C | U | U | C | U | U | G dU | -5' | J72-AS | Lamin exp 104 |
| 5'-Ac2 Ac2 | C | U | G | G | A | C | U | U | C | C | A | G | A | Ac2 | Gc2 | Ac2 Ac2 Cc2 Ac2 U$^{2'\wedge5'}$U | -3' | J65-S + 2c2 | |
| 3'-U$^{2'\wedge5'}$U | G | A | C | C | U | G | A | A | G | G | U | C | U | U | C | U | U | G dU | -5' | J72-AS | Lamin exp 115 |
| 5'-Ac2 Ac2 | C | U | G | G | A | C | U | U | C | C | A | Gc2 | Ac2 | Ac2 | Gc2 | Ac2 Ac2 Cc2 Ac2 U$^{2'\wedge5'}$U | -3' | J65-S + 4c2 | |
| 3'-U$^{2'\wedge5'}$U | G | A | C | C | U | G | A | A | G | G | U | C | U | U | C | U | U | G dU | -5' | J72-AS | Lamin exp 116 |
| 5'-Ac2 Ac2 | U | G | G | C | A | C | U | G | A | A | U | C | A | U | C | Cc2 Ac2 Uc2 Ac2 U$^{3'\wedge5'}$U | -3' | J60-S | (1CDC2) |
| 3'-U$^{3'\wedge5'}$U | A | C | C | G | U | G | A | C | U | U | A | G | U | A | G | G | U | A dU | -5' | J46-AS | 1CDC2 (1CDC2) exp 101 |
| 5'-Ac2 Ac2 | U | G | G | C | A | C | U | G | A | A | U | C | A | U | C | Cc2 Ac2 Uc2 Ac2 U$^{2'\wedge5'}$U | -3' | J67-S | |
| 3'-U$^{2'\wedge5'}$U | A | C | C | G | U | G | A | C | U | U | A | G | U | A | G | G | U | A dU | -5' | J74-AS | 1CDC2 exp 102 |
| 5'-Dc2 Dc2 | U | G | G | C | A | C | U | G | A | A | U | C | A | U | C | Cc2 Ac2 Uc2 Ac2 U$^{3'\wedge5'}$U | -3' | J61-S | |
| 3'-U$^{3'\wedge5'}$U | A | C | C | G | U | G | A | C | U | U | A | G | U | A | G | G | U | A dU | -5' | J46-AS | 1CDC2 (1CDC2) exp 103 |
| 5'-Dc2 Dc2 | U | G | G | C | A | C | U | G | A | A | U | C | A | U | C | Cc2 Ac2 Uc2 Ac2 U$^{2'\wedge5'}$U | -3' | J68-S | |
| 3'-U$^{2'\wedge5'}$U | A | C | C | G | U | G | A | C | U | U | A | G | U | A | G | G | U | A dU | -5' | J74-AS | 1CDC2 exp 104 |
| 5'-Uc2 Gc2 | G | G | U | C | A | G | C | U | C | G | U | U | A | C | Uc2 Cc2 Ac2 Ac2 U$^{3'\wedge5'}$U | -3' | J62-S | (3CDC2) |
| 3'-A$^{3'\wedge5'}$U | C | C | C | A | G | U | C | G | A | G | C | A | A | U | G | A | G | U dU | -5' | J46-AS | 3CDC2 (3CDC2) exp 101 |

-continued

| overhang | core sequence (SEQ ID NOS 131-194, respectively, in order of appearance) | | | | | | | | | | | | | overhang | strand name | siRNA duplex name |
|---|---|---|---|---|---|---|---|---|---|---|---|---|---|---|---|---|
| 5'-Uc2 Gc2 | G | G | G | U | C | A | G | C | U | C | G | U | U | A C Uc2 Cc2 Ac2 Ac2 | $U^{2'\wedge 5'}U$ -3' | J69-S | |
| 3'-$A^{2'\wedge 5'}C$ | C | C | C | A | G | U | C | G | A | G | C | A | A | U G A G U dU | -5' | J73-AS | 3CDC2 exp 102 |

Screening of Modified siRNAs (Exp 96-121)
Silencing Efficiency:Potency

The silencing efficiency of the siRNA was tested by transfecting cells with the siRNAs and quantifying the expression of the specific silenced targets by quantitative RT-PCR as describe in material and methods.

FIG. 11 represents the MAPK2 (ERK2) expression in HeLaS3.

The No treatment bar represents untreated cells. GFP and ERK2 represent control transfections with nonspecific siRNA and non modified siRNA respectively. Exp 96-121 represent the MAPK2 rest expression in cells transfected with different modified MAPK2-siRNAs (see table 1). The cells were tested also for cytotoxicity. None of the tested siRNAs was found to be cytotoxic (data not shown).

Conclusion

The additional tested chemically modified siRNAs perform better than non modified siRNAs. Silencing of higher degree is obtained at very low concentrations of siRNA compared non modified siRNA.

If the modification design, that was used for the sense strand is applied to modify the antisense strand this leads to inactivation of the siRNA (e.g. Exp102neg, Exp104neg and Exp120).

Thus the choice of the given design can be used to inactivate the sense strand. It is known that the sense strand may lead to sequence specific off target effects. Inactivation of the sense strand by the given modifications may lead to elimination of sequence specific off target effects.

Silencing Efficiency: siRNA Longevity

The duration of the silencing effects of the modified siRNAs was tested in HeLaS3 cells (FIG. 12). HeLaS3 cells were transfected with HiPerFect and 250 µM MAPK2-siRNA. MAPK2-downregulation was measured 1, 4 and 6 days after transfection. The modified siRNAs (Exp96-114), which were used to induce long term silencing, are compared to non modified siRNA indicated by (ERK2 250 pM). No treatment and GFP represent controls of untreated cells and cells treated with non specific siRNA respectively.

Conclusion:

Modified siRNAs Exp 27, Exp 97-98, Exp 101-104, Exp111 and Exp 114 induce a more efficient and prolonged silencing compared to non modified siRNA.

Silencing Efficiency Using Different Targets in Different Cells

FIG. 13 represent silencing of Lamin A/C in HeLaS3 and MCF7 cells. LaminA/C siRNA was modified using the best performing modifications.

Again No treatment bars represent Lamin expression in untreated, normal growing cells and GFP non specific in cells treated with control non specific siRNA.

Lamin non modified represent control transfections with non modified siRNA and Lamin Exp27-104 represent the Lamin/AC rest expression in cells, which were transfected with the corresponding modified siRNA.

Conclusion

Chemical Modifications Enhance the Performance of the Lamin siRNA in HelaS3 and MCF7 Cells FIG. 14 represents silencing of CDC2 in HeLaS3 and MCF7 cells. 3CDC2 siRNA was modified using the best performing modifications.

No treatment bar represents CDC2 expression in untreated, normal growing cells and GFP non specific in cells treated with control non specific siRNA.

3CDC2 non modified represent control transfections with non modified siRNA and 3CDC2 Exp27-102 represent the CDC2 rest expression in cells, which were transfected with the corresponding modified siRNA.

Conclusion

Chemical modification further enhance the performance of the already very good performing 3CDC2 siRNA in HelaS3 and MCF7 cells.

MCF7 cells were transfected with 5 nM of different siRNAs against CDC2 (FIG. 15). 3CDC2 siRNA is a high active siRNA against CDC2 and 1CDC2 indicates a siRNA of low potency. The No treatment and GFP bar represent CDC2 expression in untreated, normal growing cells and in cells treated with control non specific siRNA respectively. 3CDC2 represents the control transfection for high efficient silencing with non modified siRNA, and 1CDC2 the expression of CDC2 in cells transfected with the non modified siRNA of low potency. 1CDC2 Exp102-101 represent the CDC2 rest expression in cells, which were transfected with the corresponding modified siRNA.

Conclusion

Chemical modifications improved the performance of a less active siRNA.

Silencing Efficiency: siRNA Longevity Using siRNA Against Different Targets

HeLaS3 cells were transfected with 250 pM chemically modified or non modified siRNA against the MAPK2 target. The silencing analysis took place 1, 4 and 6 days after transfection (FIG. 16).

"MAPK2 250 pM non modified" represents the MAPK2 rest expression in HeLaS3 cells, that were treated with the non modified siRNA. Exp101-104 represent the MAPK2 rest-expression in cells treated with the corresponding modified siRNAs.

HeLaS3 cells were transfected with 250 pM chemically modified or non modified Lamin-siRNA. The Silencing analysis took place similar to the MAPK2 target 1, 4 and 6 days after Transfection (FIG. 16). Lamin 250 pM non modified represent the Lamin rest expression in HeLaS3 cells, that were treated with the non modified siRNA. Exp 101-104 represent the Lamin rest-expression in cells treated with the corresponding modified siRNAs.

Conclusion

Chemical modifications prolong the duration of silencing in transfected cells, avoiding in this way repeated transfections, which affects the normal cell growth and the significance (accuracy) of the silencing experiment.

siRNA Stability

Modified siRNAs were incubated in inactivated human serum in order to test the stability against nucleases activity.

Stability analysis was performed for each modified siRNA separately. For this purpose siRNA was incubated in human serum and at several time points an aliquots was collected and analyzed by PAGE.

All siRNAs, that were chemically modified according the design of Exp27 show very similar stability in human serum and culture medium.

FIG. 17 (A,B,C) represent some examples of modified siRNA and their extended stability in human serum.

Modified siRNAs are indicated by the name of the siRNA and the abbreviation Exp with the number of the corresponding modification.

Conclusion

The stability of the siRNA in serum is strongly sequence-depended, but in general unmodified siRNA is getting degraded very fast. Chemical modifications stabilize both stable and less stable siRNAs in presence of serum nucleases. More stable siRNA could be stabilized for over 24 h, while non modified siRNA is being degraded within 15 minutes to 1 hour. The stability of unstable siRNAs could be prolonged for several hours as well, while the corresponding non modified ones were cleaved within the very first minutes of incubation.

The invention claimed is:

1. A double-stranded siRNA molecule comprising a sense strand and an antisense strand which is essentially complementary to the sense strand, each of the sense and the antisense strands comprising a core of at least 17 nucleotides (nt), the siRNA further comprising at least one overhang comprising one or more overhang residues at the 5' and/or 3' end of the sense and/or antisense strand, wherein at least one of the one or more overhang residues is chemically modified and comprises (a) a nucleotide modified at the 2'-position by a —O—CH$_2$—O—(CH$_2$)$_2$—OH group; or (b) a nucleotide comprising in the 3'-position a —CH$_2$—O—(CH$_2$)$_7$—CH$_3$ group.

2. The siRNA molecule according to claim 1, wherein the core of the sense and the antisense strands each comprises between 17 and 23 nt.

3. The siRNA according to claim 1, wherein the 5' end of the antisense strand and/or the 5' end of the sense strand has no overhang.

4. The siRNA according to claim 1, wherein the 3' end of the antisense strand and/or the 3' end of the sense strand has an overhang.

5. The siRNA according to claim 4, wherein the 3' end of the antisense stand has an overhang, the overhang residue or overhang residues comprising at least one modification selected from (a) to (b).

6. The siRNA molecule according to claim 1, wherein at least one of the nucleotides of the core of the sense strand and/or the antisense strand comprises a modification (a).

7. The siRNA molecule according to claim 1, wherein the overhang of the sense strand and/or antisense strand comprises two modified nucleosides selected independently from the group consisting of (a) and (b).

8. The siRNA molecule according to claim 6, wherein the core nucleotide comprising the modification (a) is a nucleotide having a chemical structure according to formula VI

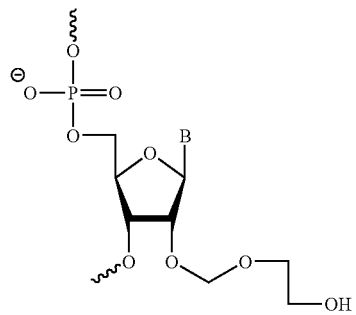

FORMULA VI wherein B is a nucleobase or derivative thereof selected from the group consisting of adenine, cytosine, thymine, guanine, and uracil.

9. The siRNA molecule according to claim 8, wherein for the modification (a) the nucleobase is adenine, cytosine, guanine or uracil.

10. A double-stranded siRNA molecule comprising a sense strand and an antisense strand which is essentially complementary to the sense strand, each of the sense and the antisense strands comprising a core of at least 17 nucleotides (nt), the siRNA further comprising at least one overhang comprising one or more overhang residues at the 5' and/or 3' end of the sense and/or antisense strand, wherein the overhang residues comprise at least two modified residues selected independently from each other from the group consisting of:

(a) two nucleosides linked by a 3' to 5' or 2' to 5' formacetal linkage;

(b) a nucleotide modified at the 2'-position by a —O—CH$_2$—O—(CH$_2$)$_2$OH group; and (c) a nucleotide comprising in the 3'-position a —CH$_2$—O—(CH$_2$)$_7$—CH$_3$ group, wherein at least one of the nucleotides of the core of the sense strand and/or the antisense strand comprises a modification (b).

11. The siRNA molecule according to claim 10, wherein the core nucleotide comprising the modification (b) is a nucleotide having a chemical structure according to formula VI FORMULA VI
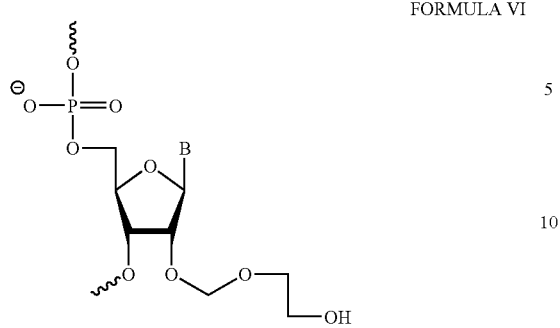
wherein B is a nucleobase or derivative thereof selected from the group consisting of adenine, cytosine, thymine, guanine, and uracil.
12. The siRNA molecule according to claim 11, wherein for the modification (b) the nucleobase is adenine, cytosine, guanine or uracil.
* * * * *